United States Patent [19]
Leturcq et al.

[11] Patent Number: 5,820,858
[45] Date of Patent: Oct. 13, 1998

[54] METHODS AND COMPOSITIONS FOR INHIBITING CD14 MEDIATED CELL ACTIVATION

[75] Inventors: Didier J. Leturcq, San Diego; Ann M. Moriarty, Poway; Richard J. Ulevitch, Del Mar; Peter S. Tobias; John C. Mathison, both of San Diego, all of Calif.

[73] Assignee: The Scripps Research Institute, La Jolla, Calif.

[21] Appl. No.: 373,297

[22] PCT Filed: May 27, 1994

[86] PCT No.: PCT/US94/05898

§ 371 Date: Jan. 23, 1995

§ 102(e) Date: Jan. 23, 1995

[87] PCT Pub. No.: WO94/28025

PCT Pub. Date: Dec. 8, 1994

Related U.S. Application Data

[63] Continuation-in-part of Ser. No. 70,160, May 28, 1993, abandoned.

[51] Int. Cl.[6] ...................... A61K 39/395; G01N 33/567; C07K 16/00; C07H 21/04
[52] U.S. Cl. ..................................... 424/133.1; 424/141.1; 424/144.1; 424/153.1; 435/7.21; 435/7.9; 435/7.93; 435/69.6; 435/252.33; 435/320.1; 435/326; 435/328; 435/332; 435/334; 435/343; 435/348; 435/352; 435/363; 530/388.22; 530/387.3; 536/23.53
[58] Field of Search ..................................... 435/326, 334, 435/7.21, 7.9, 7.93, 69.6, 320.1, 328, 332, 343, 348, 352, 363, 252.33; 530/388.22, 387.3; 424/133.1, 141.1, 144.1, 153.1; 536/23.53

[56] References Cited

FOREIGN PATENT DOCUMENTS 8601533  3/1986  WIPO .
9007861  7/1990  WIPO .

OTHER PUBLICATIONS

Tanaka et al Microbiol. Immunol. 29: 959–972 1985.
Goding, "Monoclonal Antibodies: Principles & Practice" Academic Press 1986, pp. 46–47 (Chap 2) and 125–133 (Chap 4).
Steward et al. "Antibody Affinity: Thermodynamic Aspects & Biological Significance" CRC Press, 1983 p. 102.
Casali et al Science 234: 476–479, 1986.
Morrison, Science 229: 1202–1207, 1985.
Better, et al., "Expression of Engineered Antibodies and Antibody Fragments in Microorganisms", Methods in Enzymology, vol. 178, 1989, pp. 476–496.
Putlitz, et al., "Antibody Production inn Baculovirus–Infected Insect Cells", Biotechnology, vol. 8, 1990, pp. 651–654.
Pugin, et al., "Lipopolysaccharide Activation of human Endothelial and Epithelial Cells ins Mediated by Lipopolysaccharide–Binding Protein and Soluble DC14", Proceedings of the National Academy of Sciences USA, vol. 90, Apr. 1993, pp. 2744–2748.
Martin, et al., "Lipopolysaccharide Binding Protein Enhances the Responsiveness of Alveolar Macrophages to Bacterial Lipopolysaccharide. Implications of Cytokine Production in Normal and Injured Lungs", The Journal of Clinical Investigation, vol. 90, Dec. 1992, pp. 2209–2219.
Van Voorhis, et al., "Specific Antimononuclear Phagocyte Nonclonal Antibodies", Journal of Experimental Medicine, vol. 158, Jul. 1983, pp. 126–145.
Gallay, et al., "Competition Between LPS–Binding Protein (LBP) and Anti–LPS Antibody in LPS–Induced TNF Secretion of Human Monocytes (MO)", Experientia, vol. 48, 1992, p. A66, Abstract No. 384.
Kozbor, et al., "The Production of Monoclonal Antibodies from Human Lymphocytes", Immunology Today, vol. 4, No. 3, 1983, pp. 72–79.

*Primary Examiner*—Anthony C. Caputa
*Assistant Examiner*—Mark Navarro
*Attorney, Agent, or Firm*—Fish & Richardson P.C.

[57] ABSTRACT

This invention provides monoclonal antibodies that bind to the cell surface CD14 receptor and soluble CD14 receptor. The antibodies are useful for the detection of the presence of cell surface and soluble CD14 in a sample. Chimeric and CDR grafted antibodies generated from the above monoclonal antibodies are further provided. Pharmaceutical compositions containing the above biological compositions are provided. These are useful to treat and prevent LPS-associated disorders, such as sepsis.

59 Claims, 28 Drawing Sheets

```
   +1 ATGGAGCGCG CGTCCTGCTT GTTGCTGCTG CTGCTGCCGC TGGTGCACGT
  +51 CTCTGCGACC ACGCCAGAAC CTTGTGAGCT GGACGATGAA GATTTCCGCT
 +101 GCGTCTGCAA CTTCTCCGAA CCTCAGCCCG ACTGGTCCGA AGCCTTCCAG
 +151 TGTGTGTCTG CAGTAGAGGT GGAGATCCAT GCCGGCGGTC TCAACCTAGA
 +201 GCCGTTTCTA AAGCGCGTCG ATGCGGACCG CGACCCGCGG CAGTATGCTG
 +251 ACACGGTCAA GGCTCTCCGC GTGCGGCGGC TCACAGTGGG AGCCGCACAG
 +301 GTTCCTGCTC AGCTACTGGT AGGCGCCCTG CGTGTGCTAG CGTACTCCCG
 +351 CCTCAAGGAA CTGACGCTCG AGGACCTAAA GATAACCGGC ACCATGCCTC
 +401 CGCTGCCTCT GGAAGCCACA GGACTTGCAC TTTCCAGCTT GCGCCTACGC
 +451 AACGTGTCGT GGGCGACAGG GCGTTCTTGG CTCGCCGAGC TGCAGCAGTG
 +501 GCTCAAGCCA GGCCTCAAGG TACTGAGCAT TGCCCAAGCA CACTCGCCTG
 +551 CCTTTTCCTG CGAACAGGTT CGCGCCTTCC CGGCCCTTAC CAGCCTAGAC
 +601 CTGTCTGACA ATCCTGGACT GGGCGAACGC GGACTGATGG CGGCTCTCTG
 +651 TCCCCACAAG TTCCCGGCCA TCCAGAATCT AGCGCTGCGC AACACAGGAA
 +701 TGGAGACGCC CACAGGCGTG TGCGCCGCAC TGGCGGCGGC AGGTGTGCAG
 +751 CCCCACAGCC TAGACCTCAG CCACAACTCG CTGCGCGCCA CCGTAAACCC
 +801 TAGCGCTCCG AGATGCATGT GGTCCAGCGC CCTGAACTCC CTCAATCTGT
 +851 CGTTCGCTGG GCTGGAACAG GTGCCTAAAG GACTGCCAGC CAAGCTCAGA
 +901 GTGCTCGATC TCAGCTGCAA CAGACTGAAC AGGGCGCCGC AGCCTGACGA
 +951 GCTGCCCGAG GTGGATAACC TGACACTGGA CGGGAATCCC TTCCTGGTCC
+1001 CTGGAACTGC CCTCCCCCAC GAGGGCTCAA TGAACTCCGG CGTGGTCCCA
+1051 GCCTGTGCAC GTTCGACCCT GTCGGTGGGG GTGTCGGGAA CCCTGGTGCT
+1101 GCTCCAAGGG GCCCGGGGCT TTGCCTAA
```

FIG. I

```
5' CCC CCC CTC GAG CTT CAG CAG TCA GGA CCT TCT CAG TCT CTG TCC CTC ACC TGC ACT GTC
   pro pro leu glu leu gln gln ser gly pro ser gln ser leu ser leu thr cys thr val
            4        Fr.1

ACT GGC TAC TCA ATC ACC AGT GAT TCT GCC TGG AAC TGG ATC CGG CAG TTT CCA GGA AAC AGA CTG GAG TGG
thr gly tyr ser ile thr ser asp ser ala trp asn trp ile arg gln phe pro gly asn arg leu glu trp
        31              CDR                    35B  Fr.2

ATG GGC TAC ATA AGC TAC AGT GGT AGC ACT AGC TAC AAC CCA TCT CTC AAA AGT CGA ATC TCT ATC
met gly tyr ile ser tyr ser gly ser thr ser tyr asn pro ser leu lys ser arg ile ser ile
    50                      CDR2                                65  Fr.3

ACT CGA GAC ACA TCC AAG AAC CAG TTC TTC CTG CAG TTG AAT TCG GTG ACT GAG GAC ACA GCC ACA TAT TAC
thr arg asp thr ser lys asn gln phe phe leu gln leu asn ser val thr glu asp thr ala thr tyr tyr TGT GTA AGA GGG CTC CGG TTT GCT TAC TGG GGC CAA GGG ACT CTG GTC TCT GTC TCT GCA GCA AAA ACA ACC
cys val arg gly leu arg phe ala tyr trp gly gln gly thr leu val ser val ser ala ala lys thr thr
        95          CDR3            102  Fr.4                        113 CH-1

CCC CCT TCT GTC TAT CCA CTG CCC CCT GGA TCT GCT GCC CAA ACT AAC TCC ATG GTG ACC CTG GGA TGC CTG GTC
pro pro ser val tyr pro leu pro pro gly ser ala ala gln thr asn ser met val thr leu gly cys leu val AAG GCC TAT TTC CCT GAG CCA GTG ACA GTG ACC TGG AAC TCT GGA TCC CTG TCC AGC GGT GTG CAC ACC TTC CCA
lys ala tyr phe pro glu pro val thr val thr trp asn ser gly ser leu ser ser gly val his thr phe pro GCT GTC CTG CAG TCT GAC CTC TAC ACT CTG AGC AGC TCA GTG ACT GTC CCC TCC AGC ACC TGG CCC AGC GAG ACC
ala val leu gln ser asp leu tyr thr leu ser ser ser val thr val pro ser ser thr trp pro ser glu thr GTC ACC TGC AAC GTT GCC CAC CCG GCC AGC AGC ACC AAG GTG GAC AAG AAG GTG GAC AAG GTG GAC AAG ATT 3'
val thr cys asn val ala his pro ala ser ser thr lys val asp lys lys val asp lys val asp lys ile
                                                    223

```
                        FR.1                                                              24  CDR1
5'  ATG ACA CAG TCT CCA TCT TTG GCT GTG TCT CTA GGG CAG AGG GCC CCA TAT CCT TGC AGA GCC AGT GAA
    met thr gln ser pro ser leu ala val ser leu gly gln arg ala pro ile ser cys arg ala ser glu
        5

34
    AGT GTT GAT AGT TAT GTC AAT AGT TTT CTC CAC TGG TAC CAG CAG AAA CCA GGA CAG CCA CCC AAA CTC
    ser val asp ser tyr val asn ser phe leu his trp tyr gln gln lys pro gly gln pro pro lys leu 50  CDR2                          56                          Fr.3
    CTC ATC TAT CGT GCA TCC AAC CTA CAA TCT GGG ATC CCT GCC AGG TTC AGT GGC AGT GGG TCT AGG ACA GAC
    leu ile tyr arg ala ser asn leu gln ser gly ile pro ala arg phe ser gly ser gly ser arg thr asp 89  CDR3
    TTC ACC CTC ACC ATT AAT CCT GTG GAG GCT GAT GAT GTT GCA ACC TAT TAC TGT CAG CAA AGT AAT GAG GAT
    phe thr leu thr ile asn pro val glu ala asp asp val ala thr tyr tyr cys gln gln ser asn glu asp 97  Fr.4                                    107 CH-1
    CCG ACG TCG GGA GGG GGC ACC AAG CTG GAA ATA AAA CGG GCT GAT GCT GCA CCA ACT GTA TCC ATC TTC CCC
    pro thr ser gly gly gly thr lys leu glu ile lys arg ala asp ala ala pro thr val ser ile phe pro CCA TCC AGT GAG CAG TTA ACA TCT GGA GGT GCC TCA GTC GTG TGC TTC TTG AAC AAC TTC TAC CCC AAA GAC ATC
    pro ser ser glu gln leu thr ser gly gly ala ser val val cys phe leu asn asn phe tyr pro lys asp ile AAT GTC AAG TGG AAG ATT GAT GGC AGT GAT CGA CGA AAT GGC GTC CTG AAC AGT TGG ACT GAT CAG GAC AGC AAA
    asn val lys trp lys ile asp gly ser asp arg arg asn gly val leu asn ser trp thr asp gln asp ser lys GAC AGC ACC TAC AGC ATG AGC AGC ACC CTC ACG TTG ACC AAG GAC GAG TAT GAA CGA CAT AAC AGC TAT ACC TGT
    asp ser thr tyr ser met ser ser thr leu thr leu thr lys asp glu tyr glu arg his asn ser tyr thr cys 214
    GAG GCC ACT CAC AAG ACA TCA ACT TCA CCC ATT GTC AAG AGC TTC AAC AGG AAT GAG TGT 3'
    glu ala thr his lys thr ser thr ser pro ile val lys ser phe asn arg asn glu cys
```

```
         Fr.1                                                                                    CDR1
5'  met  thr  gln  thr  pro  ser  leu  ser  ala  ser  leu  gly  asp  arg  val  thr  ile  ser  cys  arg
    ATG  ACC  CAG  ACT  CCA  TCC  CTG  TCT  GCC  TCT  CTG  GGA  GAC  AGA  GTC  ACC  ATC  AGT  TGC  AGG 35
    ala  ser  gln  asp  ile  lys  asn  tyr  leu  asn  trp  tyr  gln  gln
    GCA  AGT  CAG  GAC  ATT  AAG  AAT  TAT  TTA  AAC  TGG  TAT  CAG  CAG
                                                            Fr.2
    CDR2
    lys  val  leu  ile  tyr  tyr  thr  ser  arg  leu  his  ser  gly  val  pro
    AAA  GTC  CTA  ATC  TAC  TAC  ACA  TCA  AGA  TTA  CAC  TCA  GGA  GTC  CCA 57
    gly  ser  gly  thr  asp  tyr  ser  leu  thr  ile  ser  asn  leu  glu  gln  glu
    GGG  TCT  GGA  ACA  GAT  TAT  TCT  CTC  ACC  ATC  AGC  AAC  CTG  GAG  CAA  GAA
                                                                            Fr.3

83
    CDR3
    gln  arg  gly  asp  thr  leu  pro  trp  thr  phe  gly  gly  gly  thr  lys  leu  glu
    CAA  CGG  GGT  GAT  ACG  CTT  CCG  TGG  ACG  TTC  GGT  GGA  GGC  ACC  AAG  CTG  GAA
                                                            Fr.4

113
    ala  ala  pro  thr  val  ser  ile  phe  pro  pro  ser  ser  glu  gln  leu  thr  ser  gly  gly  ala  ser  val  val
    GCT  GCA  CCA  ACT  GTA  TCC  ATC  TTC  CCA  CCA  TCC  AGT  GAG  CAG  TTA  ACA  TCT  GGA  GGT  GCC  TCA  GTC  GTG
                                                                                                          CH-1

134
    cys  phe  leu  asn  asn  phe  tyr  pro  lys  asp  ile  asn  val  lys  trp  lys  ile  asp  gly  ser  glu  arg
    TGC  TTC  TTG  AAC  AAC  TTC  TAC  CCC  AAA  GAT  ATC  AAT  GTC  AAG  TGG  AAG  ATT  GAT  GGC  AGT  GAA  CGA gln  asn  gly  val  leu  asn  ser  trp  thr  asp  gln  asp  ser  lys  asp  ser  thr  tyr  ser  met  ser  ser
    CAA  AAT  GGC  GTC  CTG  AAC  AGT  TGG  ACT  GAT  CAG  GAC  AGC  AAA  GAC  AGC  ACC  TAC  AGC  ATG  AGC  AGC
                                                                                            175 thr  leu  thr  leu  thr  lys  asp  glu  tyr  glu  arg  his  asn  ser  tyr  thr  cys  glu  ala  thr  his
    ACC  CTC  ACG  TTG  ACC  AAG  GAC  GAG  TAT  GAA  CGA  CAT  AAC  AGC  TAT  ACC  TGT  GAG  GCC  ACT  CAC 214
    lys  ser  thr  ser  pro  ile  val  lys  ser  phe  asn  arg  asn  glu  cys  3'
    AAG  ACA  TCA  CCC  ATT  GTC  AAG  AGC  TTC  AAC  AGG  AAT  GAG  TGT
```

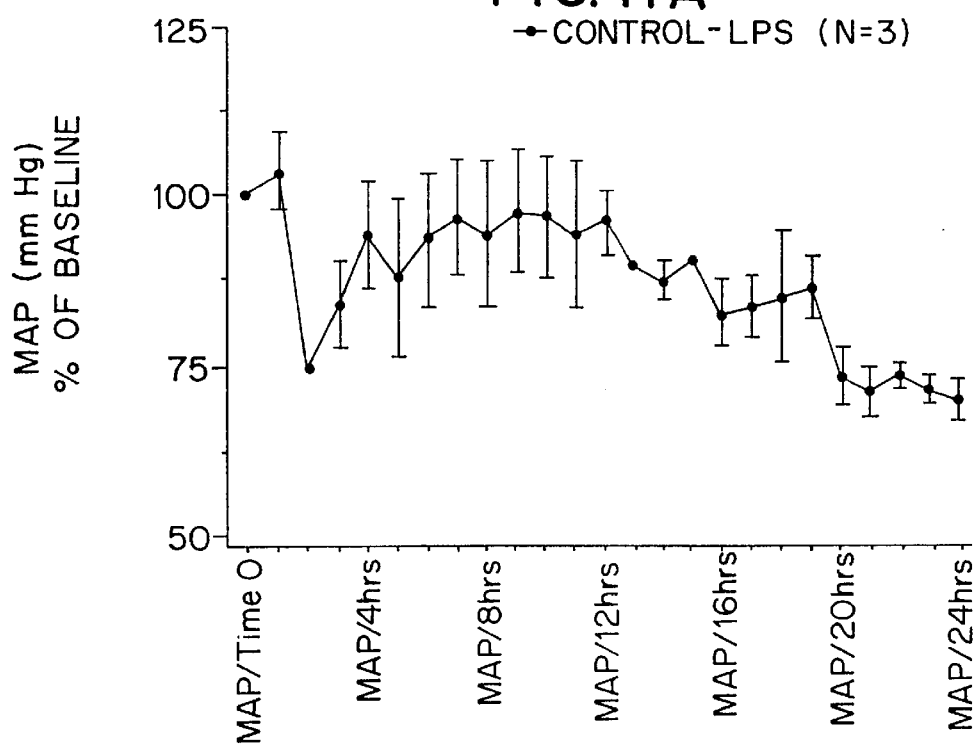
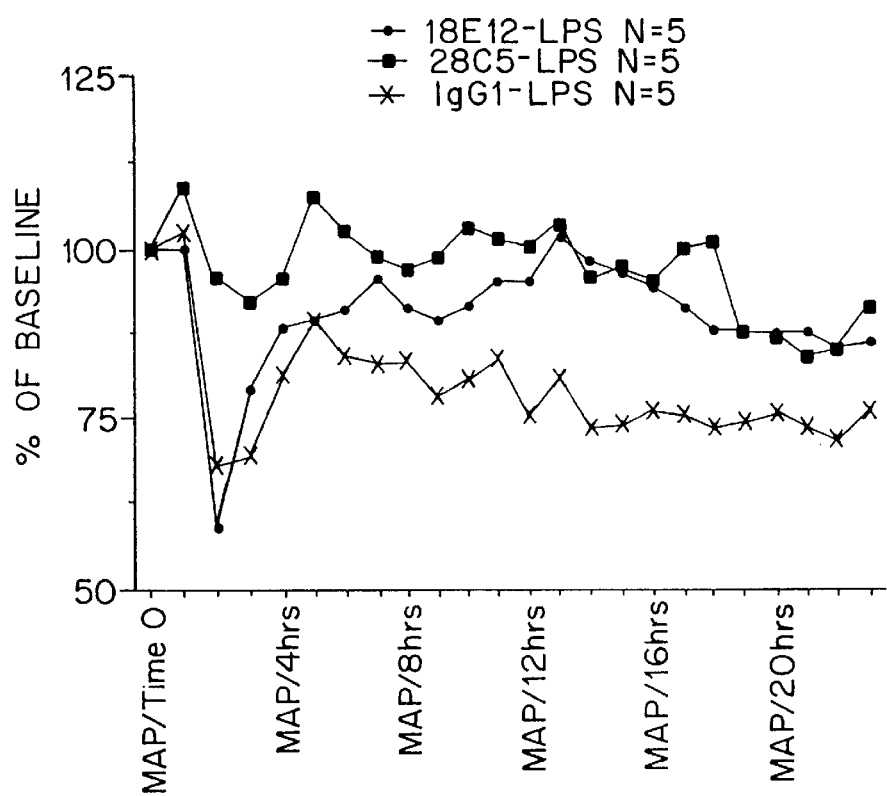

LIGHT CHAINS

```
              Fr.1                      CDR1                    Fr.2
3C10L   QSPASLAVSLGQRATISC    RASESVDSFGNSFMH    WYQQKAGQPPKSSIY
28C5L   QSPASLAVSLGQRATISC    RASESVDSYVNSFLH    WYQQKPGQPPKLLIY
23G4L   QSPASLAVSLGQRATISC    RASESVDSYGKSFMH    WYQQEPGQSPKLLIY

18E12   QTPSSLSASLGDRVTISC    RASQDIKNYLN        WYQQPGGTVKVLIY

CDR2              Fr.3                              CDR3        Fr.4
3C10L   RAANLES   GIPARFSGSGSRTDFTLTINPVEADDVATYFC    QQSYEDPWT    FGGGTKLGNQ
28C5L   RASNLQS   GIPARFSGSGSRTDFTLTINPVEADDVATYYC    QQSNEDPTT    FGGGTKLEIK
23G4L   VASKLES   GVPARFSGSGSRTDFTLTIDPVEADDAATYYC    QQMNEDPYT    FGGGTMLEIK

18E12   YTSRLHS   GVPSRFSGSGSGTDYSLTISNLEQEDFATYFC    QRGDTLPWT    FGGGTKLEIK

CH-1
3C10L   RADAAPTVSIFPPSSEQLTSGGASVVCFLNNFYPKDINVKWKIDGSERQNGVLNSWTDQDSKD
28C5L   RADAAPLVSIFPPSSEQLTSGGASVVCFLNNFYPKDINVKWKIDVSERHNGVLNSWTDQDSKD

18E12L  RADAAPTVSIFPPSSEQLTSGGASVVCFLNNFYPKDINVKWKIDGSERQNGVLNSWTDQDSKD

CH-1
3C10L   STYSMSSTKDEYERHNSYTCEATRKTLTLTSTSPIVKSFNRNEC
28C5L   STYSMSSTLTLTKDEYERHNSYTCEATHKTSTSPIVKSFNRNEC

18E12L  STYSMSSTLTLTKDEYERENSYTCEATHKTSTSPIVKSFNRNEC
```

FIG. 29

HEAVY CHAINS

|  | FR.1 | CDR1 | FR.3 | CDR2 |
|---|---|---|---|---|
| 3C10H | LVKPGGSLKLSCVASGFTFS | SYAMS | WVRQTPEKRLEWVA | SISSGGTTYYPDNVKG |
| 28C5H | LQQSGPGLVKPSQSLSLTCTVTGYSIT | SDSAWN | WIRQFPGNRLEWMG | YISYSGSTSYNPSLKS |
| 18E12H | LESGPGLVAPSQSLSITCTVSGFSLT | NYDIS | WIRQPPGKGLEWLG | VIWTSGGTNYNSAFMS |

|  | FR.3 | CDR3 | FR.4 |
|---|---|---|---|
| 3C10H | RFTISRDNARNILYLQMSSLRSEDTAMYYCAR | GYYDYHY | WGQGTTLTVSS |
| 28C5H | RISITRDTSKNQFFLQLNSVTTEDTATYYCVR | GLRFAY | WGQGTLVTVSA |
| 18E12H | RLSITKDNSESQVFLKMNGLQTDDTGIYYCVR | GDGNFYLYNFDY | WGQGTTLTVSS |

|  | CH-1 |
|---|---|
| 3C10H | AKTTPPSVYPLAPGCGDTTGSSVTLGCLVKGYFPESVTVTWNSGSLSSSVHTFPALLQSGLYTMSSSVTVPSS |
| 28C5H | AKTTPPSVYPLPPGSAAQTNSMVTLGCLVKGYFPEPVTVTWNSGSLSSGVHTFPAVLQSDLYTLSSSVTVPSS |
| 18E12H | AKTTPPSVYPLAPGSAAQTNSMVTLGCLVKGYFPEPVTVTWNSGSLSSGVHTFPAVLQSDLYTLSSSVTVPSS |

| 3C10H | TWPSQTVTCSVAHPASSTTVDKKLEPSGPISTINPCTSSRA |
|---|---|
| 28C5H | TWPSETVTCNVAHPASSTKVDKKI |
| 18E12H | TWPSETVTCNVAHPASSTKVDKKI |

FIG. 30

METHODS AND COMPOSITIONS FOR INHIBITING CD14 MEDIATED CELL ACTIVATION

This application is a continuation of the national phase of PCT/US94/05898, filed May 27, 1994, and a continuation in part of Ser. No. 07/070,160, filed May 28, 1993, now abandoned.

This invention was made with government support under Contract Nos. GM37696, GM28485, AI15136 by the NIH. The government has certain rights in the invention.

BACKGROUND OF THE INVENTION

1. Field of the Invention

The present invention relates to methods and compositions for inhibiting CD14 mediated cell activation. More particularly, the present invention relates to molecules that bind the CD14 monocyte antigen at a site which inhibits CD14 mediated cell activation.

2. Description of the Related Art

The correct functioning of a cell depends partly on its ability to communicate with its environment; external stimuli often interact with membrane receptors which, in turn, induce second messengers that ultimately affect transcription factors. The latter then activate or repress the expression of certain genes resulting in a specific pattern of proteins in a given cell.

The transcription factor NF-κB (nuclear factor-κB) is induced by a variety of stimuli to contact its DNA-binding motif and regulate a set of genes encoding immunoreceptors, cytokines, and viral proteins. Included among the various factors which can activate NF-κB is lipopolysaccharide (LPS). LPS, in turn, is intimately involved in the induction of the sepsis syndrome, including septic shock, systemic inflammatory response syndrome, and multiorgan failure.

Sepsis is a morbid condition induced by a toxin, the introduction or accumulation of which is most commonly caused by infection or trauma. The initial symptoms of sepsis typically include chills, profuse sweat, irregularly remittent fever, prostration and the like, followed by persistent fever, hypotension leading to shock, neutropenia, leukopenia, disseminated intravascular coagulation, acute respiratory distress syndrome and multiple organ failure.

Lipopolysaccharide, or endotoxin, is a toxic component found in the outer membrane of all gram-negative microorganisms (e.g., *Escherichia coli, Klebsiella pneumonia, Pseudomonas aeruginosa*). It has been determined that LPS is a potent and pleiotropic stimulus for immune cells, both in vitro and in vivo (Morrison, D. C. & J. L. Ryan, *Annu. Rev. Med.,* 38:417, 1987; Bone, R. C., *Ann. Intern. Med.,* 115:457, 1991). Compelling evidence supports the toxic role of LPS in that all of the pathophysiological effects noted in humans during gram-negative sepsis can be completely duplicated with purified LPS. The mechanism by which this toxic component activates responsive cells is complex and not fully understood. The host response to gram-negative bacterial infection is dependent upon effector cell recognition of these bacteria and/or LPS and involves serum proteins and cell membrane receptors. While the clearance of bacteria and LPS is via endocytosis and phagocytosis by reticuloendothial cells, concomitant activation of the host immune response by LPS results in secretion of cytokines by activated macrophages which can trigger the exaggerated host responses that occur during gram-negative bacterial infection.

The discovery by Tobias, et al. (*J. Exp. Med.,* 164:777, 1986) of a serum protein, identified as LPS binding protein (LBP), that exhibits high affinity binding to LPS ($K_d \approx 10^{-9}$ $M^{-1}$), helped to define the fate of LPS once released in vivo. It was demonstrated that this novel protein, with a molecular weight of 60 kD, which is synthesized in the liver is an acute phase serum protein reaching levels of 200 μg/ml in humans. The formation of high affinity LPS/LBP complexes is followed by recognition by macrophages with subsequent release of TNF-α and other macrophage secretory products (Schumann, R. R., et al., *Science,* 249:1429, 1990). Additional studies on the effects of LPS complexed with LPB led to the discovery of its specific receptor on the surface of monocytes and macrophages; CD14 (Wright, S. D., et al., *Science,* 249:1431, 1990). Further analysis with mAbs specific for CD14 revealed that the domain to which one anti-CD14 mAb (3C10; VanVoorhis, W. C., et al., *J. Exp. Med.,* 158:126, 1983) bound was part of, or in close proximity to, the LPS/LBP binding site on CD14. Monoclonal antibody 3C10, by nature of its ability to block LPS/LBP binding to CD14, was capable of inhibiting TNF-α release in a human whole blood assay, after stimulation with LPS. It is suggested by this discovery that the blocking of a single protein determinant (the ligand binding site on CD14) is sufficient, even in the presence of all other cells, proteins and factors contained in human whole blood, to inhibit TNF-α release (known to be a key mediator in septic shock) and other macrophage secretory products in response to LPS.

In spite of the advances which have been made in understanding the nature of CD14 mediated cell activation disorders, such as sepsis, considerable need remains for compositions which can be used to inhibit such activation and to diagnose these disorders. The present invention provides such compositions.

SUMMARY OF THE INVENTION

This invention provides hybridoma cell lines producing monoclonal antibodies, the monoclonal antibodies being capable of inhibiting CD14 mediated cell activation. Monoclonal antibodies produced by these cell lines also are provided. These monoclonal antibodies are broadly useful in inhibiting NF-κB activation by a ligand which binds to CD14 and would otherwise be capable of inducing NF-κB activation. Biologically active fragments of the monoclonal antibodies are provided. The antibodies and fragments are useful for the detection of the presence of cell surface-associated and soluble CD14 in a sample. Chimeric and CDR grafted antibodies generated from the above monoclonal antibodies are further provided.

Pharmaceutical compositions containing the above biological compositions are provided. These are useful to treat and prevent LPS-associated disorders, such as sepsis.

BRIEF DESCRIPTION OF THE FIGURES

FIG. 1 is the nucleic acid sequence for the human soluble CD14 receptor (SEQ ID NO:9).

FIG. 2 is the nucleic acid and amino acid sequence of the 28C5 heavy chain (SEQ ID NOS:1 and 2, respectively).

FIG. 3 is the nucleic acid and amino acid sequence of the 28C5 light chain (SEQ ID NOS:3 and 4, respectively).

FIG. 4 is the nucleic acid and amino acid sequence of the 18E12 heavy chain (SEQ ID NOS:5 and 6, respectively).

FIG. 5 is the nucleic acid and amino acid sequence of the 18E12 light chain (SEQ ID NOS:7 and 8, respectively).

FIGS. 17A–B show the mean arterial pressure of monkeys challenged with LPS and treated with 18E12 (●), 28C5 (■) or IgG1 (x).

FIG. 29 shows the amino acid sequence of the light chains of monoclonal antibodies 3C10, 28C5, 23G4 and 18E12.

FIG. 30 shows the amino acid sequence of the heavy chains of monoclonal antibodies 3C10, 28C5, and 18E12.

DETAILED DESCRIPTION OF THE INVENTION

Figure 6B:
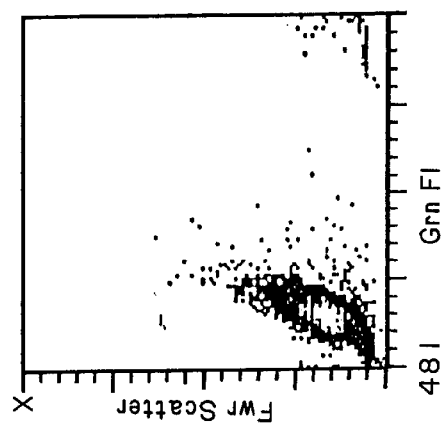
FIGS. 6A–D are FACS analysis of control THP-1 cells only.
Figure 6D:
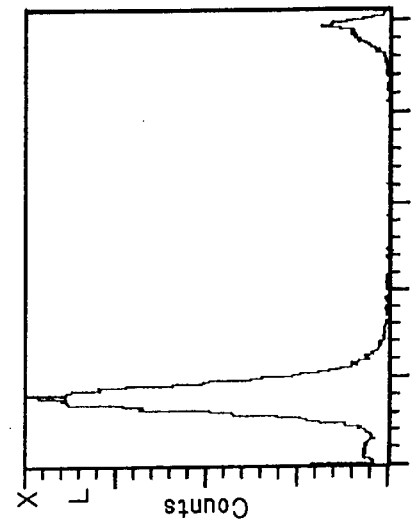
Figure 6A:
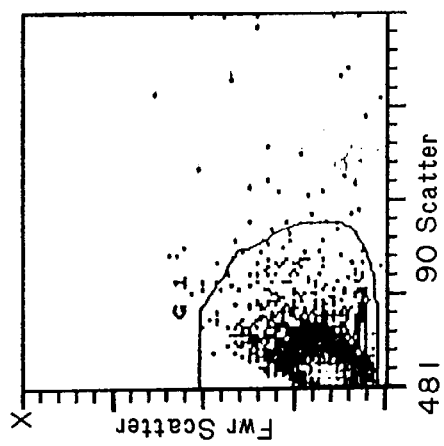
Figure 6C:
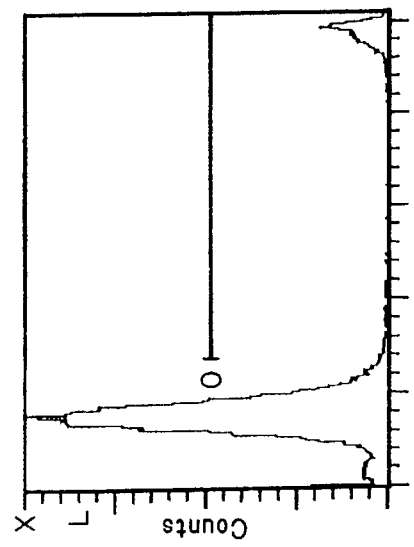
Figure 7B:
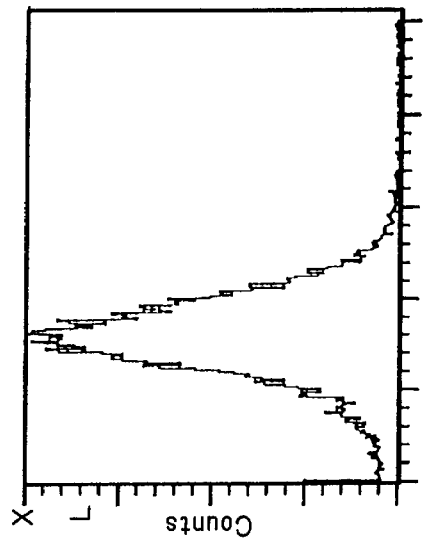
FIGS. 7A–D are FACS analysis of control THP-1 cells and FITC conjugate only.
Figure 7D:
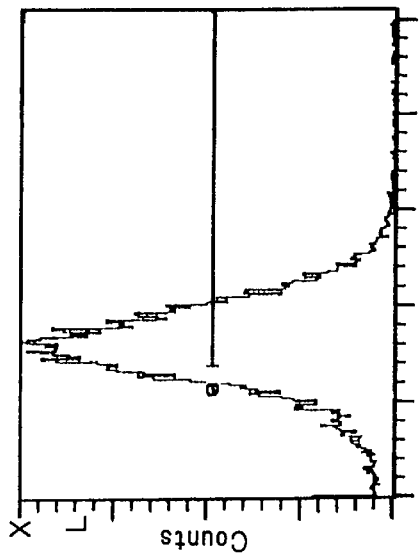
Figure 7A:
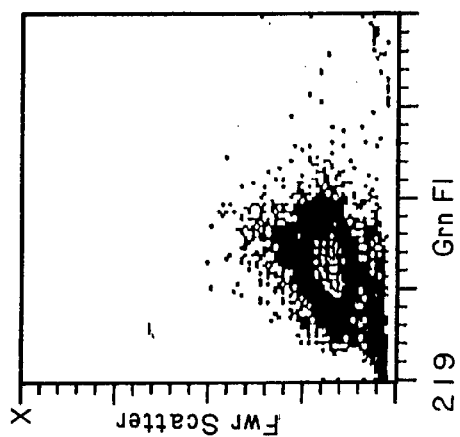
Figure 7C:
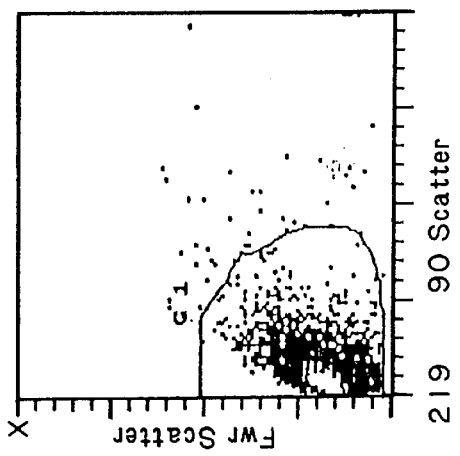
Figure 8B:
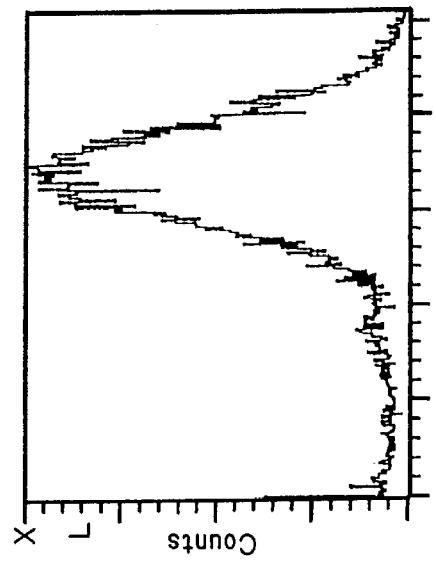
FIGS. 8A–D are FACS analysis of positive control THP-1 and MY4 antibody.
Figure 8D:
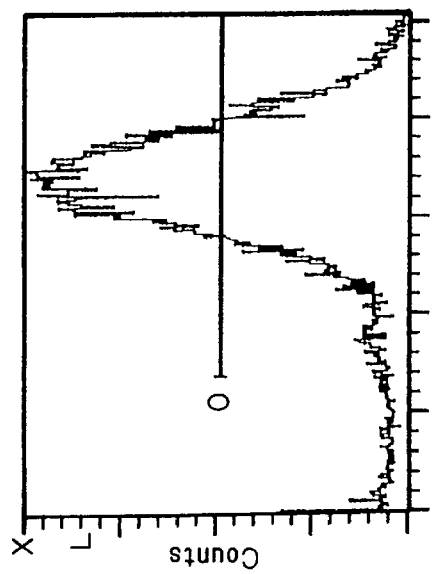
Figure 8A:
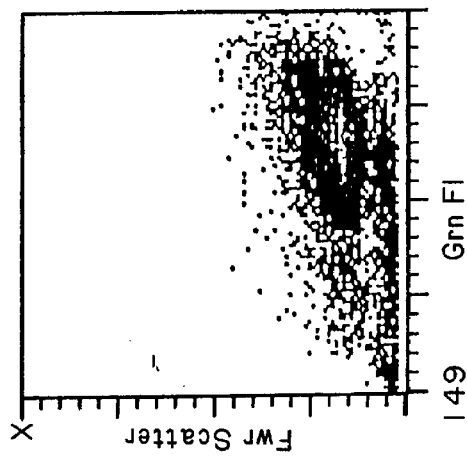
Figure 8C:
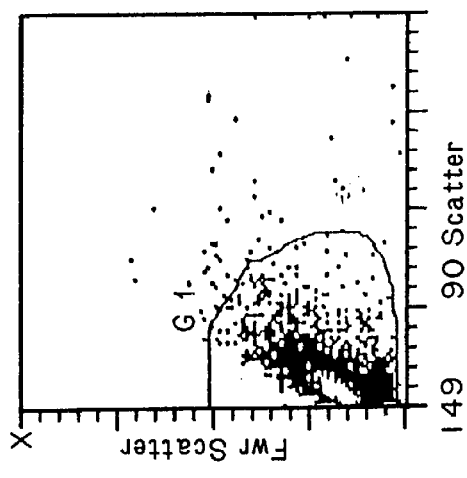
Figure 9A:
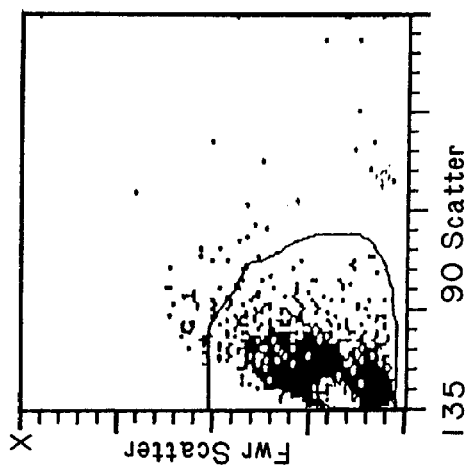
FIGS. 9A–D are is FACS analysis of 28C5 antibody.
Figure 9B:
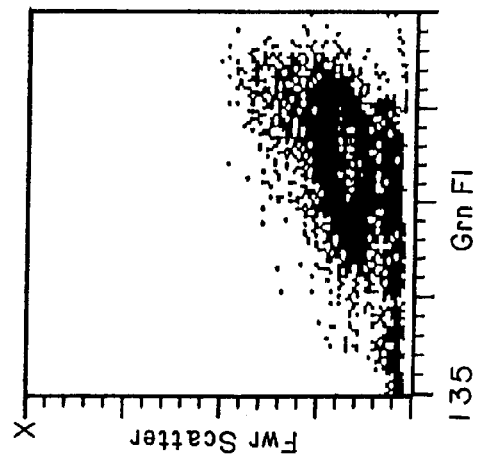
Figure 9C:
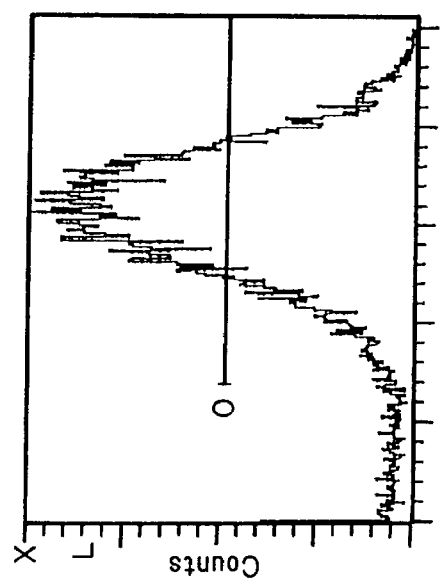
Figure 9D:
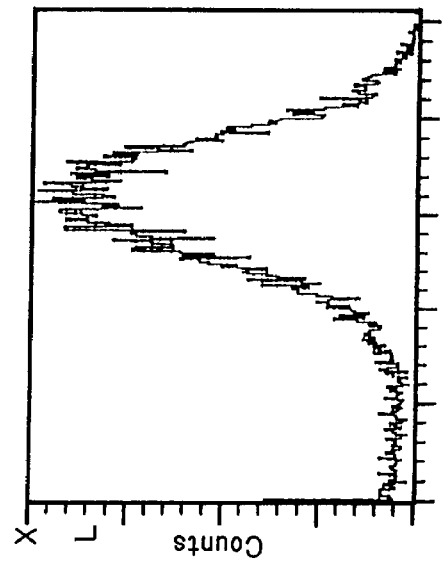
Figure 10A:
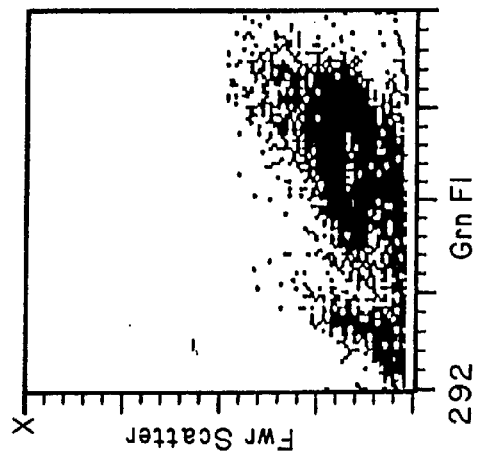
FIGS. 10A–D are FACS analysis of 18E12 antibody.
Figure 10B:
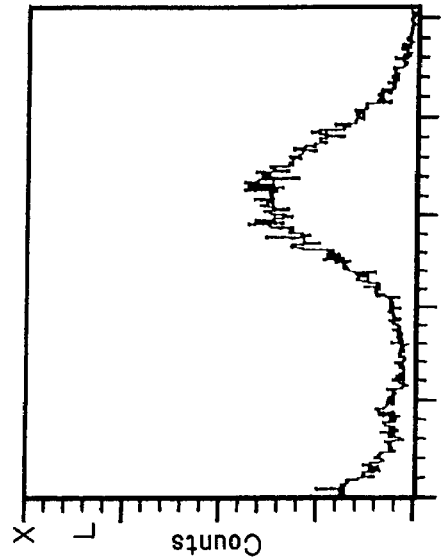
Figure 10C:
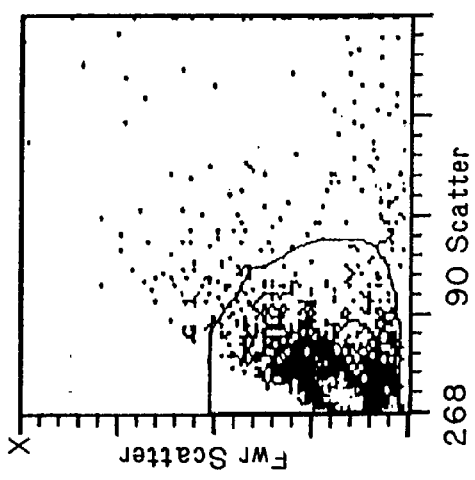
Figure 10D:
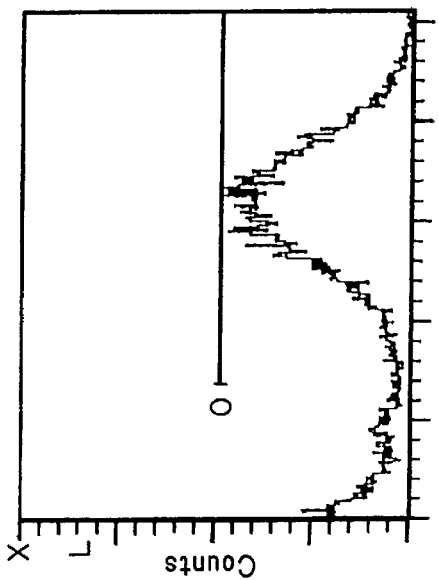

A full length polypeptide for a human soluble CD14 ("sCD14") is provided by the disclosure. As used herein, "CD14" means the cell surface receptor that has been identified as the binding site for LPS when the LPS is present as an LPS:LBP complex. The CD14 cell surface receptor is a glycerophosphatidylinositol (GPI)-linked protein present on the surface of mature monocytes, neutrophils, and macrophages. Native CD14 also is spontaneously released from the surface of mature monocytes and macrophages in a soluble form. Native sCD14 lacks the GPI anchor and is present in serum. The biological origin and function of sCD14 have not yet been fully defined (Bazil, Europ. J. Immunol., 16:1583–1589, 1986).

As used herein, "soluble" is defined as not associated in the cell surface. "Soluble CD14" is a non-cell-associated CD14 molecule further characterized as specifically binding LPS:LBP complexes and/or LPS alone. "Recombinant human sCD14" includes both a full-length amino acid soluble human CD14 protein encoded by the nucleic acid sequence in FIG. 1 (SEQ ID NO:9) and its truncated version. For the purposes of identification only, the full-length protein is designated 523 and the truncated version is designated 847. This human sCD14 is useful as an immunogen for the generation of polyclonal and monoclonal antibodies and to detect the presence of LPS in a patient sample. When used as an immunogen, 523 provided advantages over prior art CD14 immunogens, e.g., 523 provided a higher number of CD14-specific positive clones, it eliminated the number of non-specific responses to other immunogenic proteins which would be present in whole cell extracts, and it decreased the number of screening attempts needed to obtain the antibodies of interest. This full length human sCD14 polypeptide has the nucleic acid sequence as shown in FIG. 1, SEQ ID NO:9. Using this sequence, one of skill in the art can produce polypeptide of like sequence by chemical synthesis or recombinantly. The truncated version ("847") has eight (8) amino acids from the carboxyl end of the sequence deleted.

Minor modifications of sCD14 primary amino acid sequence may result in proteins which have substantially equivalent function compared to the sCD14 protein described herein. Such modifications may be deliberate, as by site-directed mutagenesis, or may be spontaneous. All proteins produced by these modifications are included herein as long as sCD14 function exists.

Modifications of sCD14 primary amino acid sequence also include conservative variations. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

The invention provides a nucleic acid molecule encoding the human soluble CD14 polypeptide as shown in FIG. 1 (SEQ ID NO:9). The invention also encompasses nucleic acids molecules which differ from that of the nucleic acid molecule shown in FIG. 1, but which produce the same phenotypic or immunogenic effect when the nucleic acid molecule is expressed. This invention encompasses nucleic acid molecules characterized by changes in non-coding regions that do not alter the phenotype of the polypeptide produced therefrom when compared to the nucleic acid molecule described hereinabove. Therefore, it is understood that all polynucleotides encoding all or a portion of sCD14 are also included herein, so long as they exhibit a function of sCD14, such as the ability to induce or bind antibody. Such polynucleotides include both naturally occurring and intentionally manipulated, for example, mutagenized polynucleotides. These polynucleotides include DNA and RNA sequences which encode the protein.

This invention further encompasses nucleic acid molecules which hybridize to the nucleic acid molecule of the subject invention. As used herein, the term "nucleic acid" encompasses RNA as well as single and double stranded DNA and cDNA.

Using the sequence provided in FIG. 1 and methods well known to those of skill in the art (as exemplified in Sambrook, et al., *Molecular Cloning: A Laboratory Manual*, Cold Spring Harbor Laboratory, New York (1989), incorporated throughout by reference), human sCD14 can be recombinantly produced and isolated. Expression vectors containing this sequence, as well as host cells containing the vectors, are also provided by this invention. As used herein, the term "vector" or "expression vector" refers to sequences of heterologous nucleic acids which are capable of being expressed in selected host cells through operational association with other sequences capable of effecting their expression, such as promoter and enhancer sequences. For the purpose of illustration only, these expression vectors can be bacterial plasmids, bacterial phages, animal viruses, baculoviruses or cosmids. Procaryotic host cells such as *E. coli* can be used for recombinantly producing these polypeptides when the vector is a bacterial plasmid or a bacterial phage. Eucaryotic host cells can be, but are not limited to mammalian host cells, e.g., Chinese Hamster Ovary Cells (CHO) or insect cells for baculoviral expression.

A method of recombinantly producing the human sCD14 is provided by this invention. This method requires growing the host cells described above under suitable conditions such that the sCD14 nucleic acid molecule is transcribed and translated. Upon expression, the recombinant sCD14 can be isolated from the cell culture by use of an affinity column composed of commercially available CD14 monoclonal antibody.

This invention also provides polyclonal antibodies and monoclonal antibodies, specifically reactive with cell surface CD14 receptor and soluble CD14. The antibodies of the invention inhibit CD14 mediated cell activation by a ligand otherwise capable of binding to the CD14 receptor and activating the cell, for example, to induce NF-κB activation or produce and release a cytokine. Monoclonal antibodies provided herein are capable of inhibiting CD14 mediated cell activation by the ligand even when the ligand has bound to CD14. The monoclonal antibodies may allow at least about 50% ligand binding to occur between the ligand and CD14, although these antibodies can allow at least about 80% binding of ligand to CD14 to occur and still be capable of inhibiting CD14 mediated cell activation.

As used herein, a "antibody or polyclonal antibody" means a protein that is produced in response to immunization with an antigen or through recombinant cloning techniques. The term "monoclonal antibody" means an immunoglobulin derived from a single clone of cells. All monoclonal antibodies derived from the clone are chemically and structurally identical, and specific for a single antigenic determinant.

Laboratory methods for producing polyclonal antibodies and monoclonal antibodies are known in the art (see, Harlow and Lane, *Antibodies: A Laboratory Manual*, Cold Spring Harbor Laboratory, New York (1988), incorporated herein by reference). The monoclonal antibodies of this invention can be biologically produced by introducing full length human recombinant polypeptide for soluble CD14 into an animal, e.g., a mouse or a rabbit. The antibody producing cells in the animal are isolated and fused with myeloma cells or heteromyeloma cells to produce hybrid cells or hybridomas. Accordingly, the hybridoma cells producing the monoclonal antibodies of this invention also are provided. Monoclonal antibodies produced in this manner include, but are not limited to the monoclonal antibodies designated 18E12, 28C5, 23G4, 5G3, 4F2, 13A7, 10B7, and 26F3. The hybridoma cell lines 18E12, 28C5 and 23G4 have been deposited with the American Type Culture Collection (ATCC) 12301 Parklawn Drive, Rockville, Md. 20852, U.S.A., under the provisions of the Budapest Treaty on the International Deposit of Microorganisms for the Purposes of Patent Procedure. 18E12 and 28C5 were deposited on May 27, 1993 and were accorded ATCC accession numbers HB11363 and HB11364, respectively. 23G4 was deposited on May 25, 1994 and was accorded ATCC accession number HB11637. These deposits were made under the provisions of the Budapest Treaty on the International Recognition of the Deposit of Microorganisms for the Purpose of Patent Procedure and the Regulations thereunder (Budapest Treaty). This assures maintenance of viable cultures for 30 years from the date of deposit. The organisms will be made available by ATCC under the terms of the Budapest Treaty which assures permanent and unrestricted availability of the progeny of the culture to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. §122 and the Commissioner's rules pursuant thereto (including 37 C.F.R. §1.14 with particular reference to 886 OG 638).

The assignee of the present application has agreed that if the culture deposit should die or be lost or destroyed when cultivated under suitable conditions, it will be promptly replaced on notification with a viable specimen of the same culture. Availability of a deposited strain is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the cell lines deposited, since the deposited embodiment is intended as a single illustration of one aspect of the invention and any cell lines that are functionally equivalent are within the scope of this invention. The deposit of material does not constitute an admission that the written description herein contained is inadequate to enable the practice of any aspect of the invention, including the best mode thereof, nor is it to be construed as limiting the scope of the claims to the specific illustration that it represents.

Thus, using the unique full length recombinant protein for soluble CD14 and the well known methods, one of skill in the art can produce and screen the hybridoma cells and antibodies of this invention.

The monoclonal antibodies of this invention can be characterized as being able to specifically react with cell surface CD14 receptor and soluble CD14 and inhibit CD14 mediated cell activation. Methods of determining binding specificities are outlined below. In one embodiment, the monoclonal antibodies are further characterized as having a binding affinity for CD14 greater than the affinity of anti-CD14 antibody 3C10 (available from the American Type Culture Collection). One such monoclonal antibody is the monoclonal antibody designated 28C5. Scatchard analysis of 28C5 binding to dihydroxyvitamin D3 induced THP1 cells gave an affinity of $3\times10^{-9}M^{-1}$. Monoclonal antibody 28C5 and 23G4, and antibodies of like specificity and affinity, are further characterized as being able to inhibit activation and also inhibit CD14 binding of the ligand which induces NF-κB activation. In addition, all of the monoclonal antibodies of the invention can be characterized by their ability to inhibit cytokine release from CD14+ cells when such cells are contacted with the inducing ligand. As used herein, a cytokine shall include, but is not limited to TNF-α, IL-1, IL-6, and IL-8.

In an alternative embodiment, the monoclonal antibody 18E12 and monoclonal antibodies of like specificity are further characterized as having the ability to inhibit CD14 mediated cell activation, but do not significantly inhibit CD14 binding (i.e., these antibodies allow CD14 binding) with the ligand which is otherwise capable of inducing CD14 mediated cell activation. Monoclonal antibodies with the specificity of 18E12 will allow from at least about 50% to at least about 80% binding to occur between the ligand and CD14.

The preferred monoclonal antibodies described herein, 18E12 and 23G4, bind to both human and baboon CD14, whereas, 28C5 does not bind baboon CD14.

Although LBP is the predominant serum protein involved in presentation of LPS to CD14, other serum proteins may also bind to LPS under appropriate conditions and facilitate LPS-CD14 interactions (Wright, S. D., et al., *J. Expt. Med.*, 176:719–727, 1992). Regardless of whether LBP or other proteins predominate under physiologic conditions the effects of the monoclonal antibodies 18E12, 23G4 or 28C5 are the same since these antibodies prevent the effects of LPS on NF-κB or cytokine production in the presence plasma (or serum).

This invention also provides biological active fragments of the polyclonal and monoclonal antibodies described above. These "antibody fragments" retain some ability to selectively bind with its antigen or receptor. Such antibody fragments can include, but are not limited to:

(1) Fab, the fragment which contains a monovalent antigen-binding fragment of an antibody molecule produced by digestion with the enzyme papain to yield an intact light chain and a portion of one heavy chain;

(2) Fab', the fragment of an antibody molecule obtained by treating with pepsin, followed by reduction, to yield an intact light chain and a portion of the heavy chain; two Fab' fragments are obtained per antibody molecule;

(3) (Fab')$_2$, the fragment of the antibody that is obtained by treating with the enzyme pepsin without subsequent reduction; F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art, see for example, Harlow and Lane, supra.

Additional examples of "biologically active fragment" include antibody fragments specifically including the CDRs of the antibodies as defined below. These CDR regions are identified in FIGS. 2 through 5 and 29–30, (SEQ ID NOS:1 through 8 and SEQ ID NOS:22–24). CDRs of these antibodies are useful to generate CDR grafted antibodies as described below. Additional examples of "biologically active fragments" include fragments specifically including the framework regions of the antibodies also identified in FIGS. 2 through 5 and 29–30, (SEQ ID NOS:1 through 8 and SEQ ID NOS:22–24). The framework regions of the antibodies are useful as primers for PCR amplification of the CDRs.

Also encompassed by this invention are proteins or polypeptides that have been recombinantly produced, biochemically synthesized, chemically synthesized or chemically modified, that retain the ability to bind CD14 cell surface receptor and soluble CD14 as well as inhibit CD14 mediated cell activation by binding of activating ligand to CD14+ cells, of the corresponding native polyclonal or monoclonal antibody. The ability to bind with an antigen or receptor is determined by antigen-binding assays known in the art such as antibody capture assays (see, for example, Harlow and Lane, supra).

Any of the above described antibodies or biologically active antibody fragments can be used to generate CDR grafted and chimeric antibodies.

"CDR" or "complementarity determining region" or "hypervariable region" is defined as the amino acid sequences on the light and heavy chains of an antibody which form the three-dimensional loop structure that contributes to the formation of the antigen binding site.

As used herein, the term "CDR grafted" antibody refers to an antibody having an amino acid sequence in which at least parts of one or more CDR sequences in the light and/or variable domain have been replaced by analogous parts of CDR sequences from an antibody having a different binding specificity for a given antigen or receptor.

As used herein, the terms "light chain variable region" and "heavy chain variable region" refer to the regions or domains at the N-terminal portion of the light and heavy chains respectively which have a varied primary amino acid sequence for each antibody. The variable region of the antibody consists of the amino terminal domain of the light and heavy chains as they fold together to form a three-dimensional binding site for an antibody.

The analogous CDR sequences are said to be "grafted" onto the substrate or recipient antibody. The "donor" antibody is the antibody providing the CDR sequence, and the antibody receiving the substituted sequences is the "substrate" antibody. One of skill in the art can readily produce these CDR grafted antibodies using the teachings provided herein in combination with methods well known in the art (see Borrebaeck, C. A., *Antibody Engineering: A Practical Guide*, W. H. Freeman and Company, New York, 1992, incorporated throughout by reference).

This invention further provides chimeric antibodies of the above described antibodies or biologically active fragments. As used herein, the term "chimeric antibody" refers to an antibody in which the variable regions of antibodies derived from one species are combined with the constant regions of antibodies derived from a different species. Chimeric antibodies are constructed by recombinant DNA technology, and are described in Shaw, et al., *J. Immun.*, 138:4534 (1987), Sun, L. K., et a/., *Proc. Natl. Acad. Sci. USA*, 84:214–218 (1987), for example.

Nucleic acid molecules encoding the antibodies, monoclonal antibodies, biologically active fragments, chimeric antibodies and CDR grafted antibodies described above also are provided by this invention. "Nucleic acid" is intended to include single and double stranded DNA, cDNA and RNA. These nucleic acid molecules can be operationally linked to promoter of RNA transcription. The invention also encompasses nucleic acids molecules which differ from that of the nucleic acid molecules described above, but which produce the same phenotypic effect. The invention encompasses nucleic acid molecules characterized by changes in non-coding regions that do not alter the phenotype of the polypeptide produced therefrom when compared to the nucleic acid molecule described hereinabove. This invention further encompasses nucleic acid molecules which hybridize to the nucleic acid molecule of the subject invention. As used herein, the term "nucleic acid" encompasses RNA as well as single and double stranded DNA and cDNA.

In one embodiment, these nucleic acid molecules are inserted into expression vectors as noted above. The expression vectors can be inserted into suitable host cells. When the cells are induced to grow under conditions favoring transcription and translation of the inserted nucleic acid sequence, a recombinant protein or polypeptide is produced which can then be isolated and used for diagnosis or therapy as described below. Methods of recombinantly producing polypeptides and proteins are generally known (see Sambrook, et al., supra and Kreigler, M., *Gene Transfer and Expression: A Laboratory Manual*, W. H. Freeman and Company, New York, 1990, each incorporated herein by reference).

Pharmaceutical compositions also are provided by this invention. These pharmaceutical compositions contain any of the above described polypeptides, fragments, antibodies, monoclonal antibodies, antibody fragments, chimeric antibodies or CDR grafted antibodies, each alone or in combination with each other, and a pharmaceutically acceptable carrier. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. These pharmaceutical compositions are useful for diagnostic or therapeutic purposes.

The monoclonal antibodies of the invention are suited for in vitro for use, for example, in immunoassays in which they can be utilized in liquid phase or bound to a solid phase carrier. In addition, the monoclonal antibodies in these immunoassays can be detectably labeled in various ways. Examples of types of immunoassays which can utilize monoclonal antibodies of the invention are competitive and non-competitive immunoassays in either a direct or indirect format. Examples of such immunoassays are the radioimmunoassay (RIA) and the sandwich (immunometric) assay. Detection of the antigens using the monoclonal antibodies of the invention can be done utilizing immunoassays which are run in either the forward, reverse, or simultaneous modes, including competition immunoassays and immunohistochemical assays on physiological samples. Those of skill in the art will know, or can readily discern, other immunoassay formats without undue experimentation.

The monoclonal antibodies of the invention can be bound to many different carriers and used to detect CD14. Examples of well-known carriers include glass, polystyrene, polypropylene, polyethylene, dextran, nylon, amyloses, natural and modified celluloses, polyacrylamides, agaroses, and magnetite. The nature of the carrier can be either soluble or insoluble for purposes of the invention. Those skilled in the art will know of other suitable carriers for binding monoclonal antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, and bioluminescent compounds. Those of ordinary skill in the art will know of other suitable labels for binding to the monoclonal antibodies of the invention, or will be able to ascertain such, using routine experimentation. Furthermore, the binding of these labels to the monoclonal antibodies of the invention can be done using standard techniques common to those of ordinary skill in the art.

Further provided herein is a method of blocking the binding of LPS/LBP complex to a CD14 receptor on the surface of a cell by contacting the cell with a monoclonal antibody capable of binding to the complex, e.g., a monoclonal antibody with the specificity and affinity of 28C5, or 23G4 or a biologically active fragment of the monoclonal antibody. Also disclosed is a method of inhibiting NF-κB activation of a cell expressing CD14 receptor in the presence of a ligand (such as LPS or LPS/LBP) which is capable of inducing NF-κB activation. This method provides contacting the cell with an antibody having the ability to specifically bind cell surface receptor CD14 and full length human soluble CD14 or a biologically active fragment of the antibody. Specific examples of such antibodies are the antibodies designated 28C5, 23G4 and 18E12.

Several therapeutic methods are provided herein which can be utilized in animals and humans. One therapeutic method is a means to treat or prevent disease associated with NF-κB activation, such as sepsis, by administering to a subject with the disease an effective amount of an antibody having the ability to specifically bind cell surface receptor CD14 and soluble CD14 or a biologically active fragment of the antibody. The above method is especially advantageous when a monoclonal antibody having the binding specificity of 18E12 is used. Because 18E12 and the like antibodies can inhibit NF-κB activation even after LPS has bound the CD14 receptor, such antibody can be used for the treatment of later stage sepsis. As used herein, later stage sepsis means the disease course after LPS has bound CD14 cell-associated receptor. Significantly, 18E12 and like antibodies are capable of allowing the cell to which the antibody has bound to continue to transport LPS or LPS/LBP complex into the cell. This property provides the added benefit of allowing the removal of LPS or LPS/LBP complex from the in vivo system thereby inhibiting the possible pathological interaction of LPS or LPS/LBP complex at some other in vivo site.

Alternatively, monoclonal antibodies 28C5 and 23G4 are preferred in the method of the invention where treatment is prophylactic or it is desirable to block LPS/LBP from binding to CD14, thereby inhibiting cytokine release and cell activation.

The invention provides a therapeutic method of ameliorating sepsis or one or more of the symptoms of sepsis comprising administering to a subject displaying symptoms of sepsis or at risk for developing sepsis, a therapeutically effective amount of a monoclonal antibody of the invention that binds to CD14 and inhibits cell activation. Such symptoms which may be ameliorated include those associated with a transient increase in the blood level of TNF, such as fever, hypotension, neutropenia, leukopenia, thrombocytopenia, disseminated intrvascular coagulation, adult respiratory distress syndrome, shock and multiple organ failure. Patients who require such treatment include those at risk for or those suffering from toxemia, such as endotoxemia resulting from a gram-negative bacterial infection, venom poisoning, or hepatic failure, for example. In addition, patients having a gram-positive bacterial, viral or fungal infection may display symptoms of sepsis and may benefit from such a therapeutic method as described herein. Those patients who are more particularly able to benefit from the method of the invention are those suffering from infection by *E. coli, Haemophilus influenza* B, *Neisseria meningitides*, staphylococci, or pneumococci. Patients at risk for sepsis include those suffering from burns, gunshot wounds, renal or hepatic failure.

The term "therapeutically effective amount" as used herein refers to the amount of monoclonal antibody which binds to CD14 and blocks signalling events such as cytokine release, used is of sufficient quantity to decrease the subject's response to LPS and decrease the symptoms of sepsis. The term "therapeutically effective" therefore includes that amount of antibody sufficient to prevent, and preferably reduce by at least 50%, and more preferably sufficient to reduce by 90%, a clinically significant increase in the plasma level of TNF, for example. The dosage ranges for the administration of the monoclonal antibody of the invention, for example 18E12, 28C5 and 23G4, are those large enough to produce the desired effect. Generally, the dosage will vary with the age, condition, sex, and extent of the infection with bacteria or other agent as described above, in the patient and can be determined by one skilled in the art. The dosage can be adjusted by the individual physician in the event of any contraindications. In any event, the effectiveness of treatment can be determined by monitoring the level of LPS and TNF in a patient. A decrease in serum LPS and TNF levels should correlate with recovery of the patient.

In addition, patients at risk for or exhibiting the symptoms of sepsis can be treated by the method as described above, further comprising administering, substantially simultaneously with the therapeutic administration of a monoclonal antibody of the invention, an inhibitor of TNF, an antibiotic, or both. For example, intervention in the role of TNF in sepsis, either directly or indirectly, such as by use of an anti-TNF antibody and/or a TNF antagonist, can prevent or ameliorate the symptoms of sepsis. Particularly preferred is the use of an anti-TNF antibody as an active ingredient, such as a monoclonal antibody with TNF specificity as described by Tracey, et al. (*Nature*, 330:662, 1987).

A patient who exhibits the symptoms of sepsis may be treated with an antibiotic in addition to the treatment with a truncated LBP or antibody of the invention. Typical antibiotics include an aminoglycoside, such as gentamycin or a beta-lactam such as penicillin, or cephalosporin. Therefore, a preferred therapeutic method of the invention includes administering a therapeutically effective amount of an antibody of the invention, substantially simultaneously with administration of a bactericidal amount of an antibiotic.

The term "bactericidal amount" as used herein refers to an amount sufficient to achieve a bacteria-killing blood concentration in the patient receiving the treatment. The bactericidal amount of antibiotic generally recognized as safe for administration to a human is well known in the art, and as is known in the art, varies with the specific antibiotic and the type of bacterial infection being treated.

Preferably, administration of a monoclonal antibody of the invention occurs within about 48 hours and preferably within about 2–8 hours, and most preferably, substantially concurrently with administration of the antibiotic.

For the purposes of this invention, a subject is an animal or a human patient and an effective amount is from about 0.25 mg/kg/body weight to about 50 mg/kg/body weight. In one embodiment, the effective amount is from about 0.5 mg/kg/body weight to about 10 mg/kg/body weight. When the subject is a human patient, the preferred amount is from about 0.5 mg/kg/body weight to about 8 mg/kg/body weight.

As is known to those of skill in the art, the above methods may be combined to enhance the therapeutic and prophylactic effects. Means of administering pharmaceutical compositions are well known to those of skill in the art and include, but are not limited to administration intravenously, orally, intraperitoneally, subcutaneously or by inhalation therapy.

The following examples are intended to illustrate but not limit the invention.

EXAMPLE 1

GENERATION OF SOLUBLE CD14 (sCD14) AND PRODUCTION OF MONOCLONAL ANTIBODIES

A. Cloning of sCD14

A copy of the human CD14 gene was obtained. The description of the cloning of this gene, from a human monocytic cell line (HL-60) (American Type Culture Collection, ATCC No. 240), is described in *Blood*, 73:284 (1989), incorporated herein by reference. The CD14 gene was excised from this expression vector and cloned into the mammalian expression vector pEE14 (Celltech). This vector has an inducible glutamine synthetase gene (GS) which was used to amplify the inserted DNA fragments containing the CD14 gene. A full-length DNA sequence of the gene was cloned into pEE14. Cells expressing soluble CD14 were identified as an ELISA assay by reactivity with commercially available anti-CD14 mAbs. One clone, identified as 523, was demonstrated to express both soluble CD14 and a membrane associated form which could be detected by FACS analysis. The soluble form of clone 523 was determined to be N-terminally processed at amino acid residue 20 of the predicted translated protein sequence. The sequence for this protein is set forth in FIG. 1. Amino acid residues 1–19 of the translated CD14 sequence was predicted to be a signal sequence (Gene Works, Intelligenetics). It was determined by C-teminal sequence analysis that the C-terminus was intact; no processing had occurred which was similar to that noted in the soluble CD14 isolated from human serum (Bazil, et al., *Eur. J. Immunol.*, 16:1583, 1986, incorporated herein by reference). The soluble CD14 isolated from urine of nephritic patients is lacking the eight most C-terminal amino acids (Bazil, *Mol. Immunol.*, 26:657, 1989). The clone 523 may have avoided the processing steps at the C-terminus as a consequence of its expression in CHO cells.

Purification of the soluble CD14 was accomplished by purifying the antigen on an affinity column composed of commercially available mAb 63D3 (obtainable from the American Type Culture Collection (ATCC No. HB 44)).

B. Generation of sCD14 Monoclonal Antibodies

Monoclonal antibodies to human soluble CD14 were generated by somatic cell fusion between spleen cells from BALB/c mice immunized with purified human recombinants CD14 described above, and the mouse myeloma cell line X63.Ag8.653. Monoclonal antibodies 28C5, 18E12, 26F3 and 23G4 are IgG1 mAb which were identified by screening against CD14 in an ELISA assay. Binding to native CD14 was confirmed by flow microfluoremetry on CD14$^+$ cells and immunoprecipitation of biosynthetically labeled CD14. Monoclonal antibodies 28C5, 23G4 and 18E12 recognize cell-associated and soluble CD14. Competition studies indicated that these mAb bound to three distinct CD14 epitopes (overlap between 28C5 and 23G4).

EXAMPLE 2

CHARACTERIZATION OF MONOCLONAL ANTIBODIES

A. FACS Analysis of CD14+ Positive Cells with anti-CD14 Monoclonal Antibodies

THP-1 cells (American Type Culture Collection, ATCC No. TIB 202) were induced with dihydroxyvitamin D3 for 48 hours and cells were then washed with DMEM (Dulbecco's modified Eagles medium with 4.5 g/L glucose, 90% fetal bovine serum, 10% followed by PBS with 1% BSA and 0.02% azide). One million cells/tube were reacted with first antibody (anti-CD14s supernatants) at 1:2 dilution for 45 minutes at 4° C. Cells are washed with PBS/BSA/azide. The second antibody was added (goat anti-mouse IgG, FITC-labeled (Cappel)) at a 1:250 dilution for 30 minutes at 4° C. Cells are washed 2× with same buffer. Pellets resuspended in 1 ml of buffer. Fluorescence intensity was measured by a Cytofluorograph (Ortho Instruments). The results are shown in FIGS. 6 through 10.

B. Determination of Binding Affinity of Anti-sCD14 Monoclonal Antibodies for Soluble CD14

Figure 11:
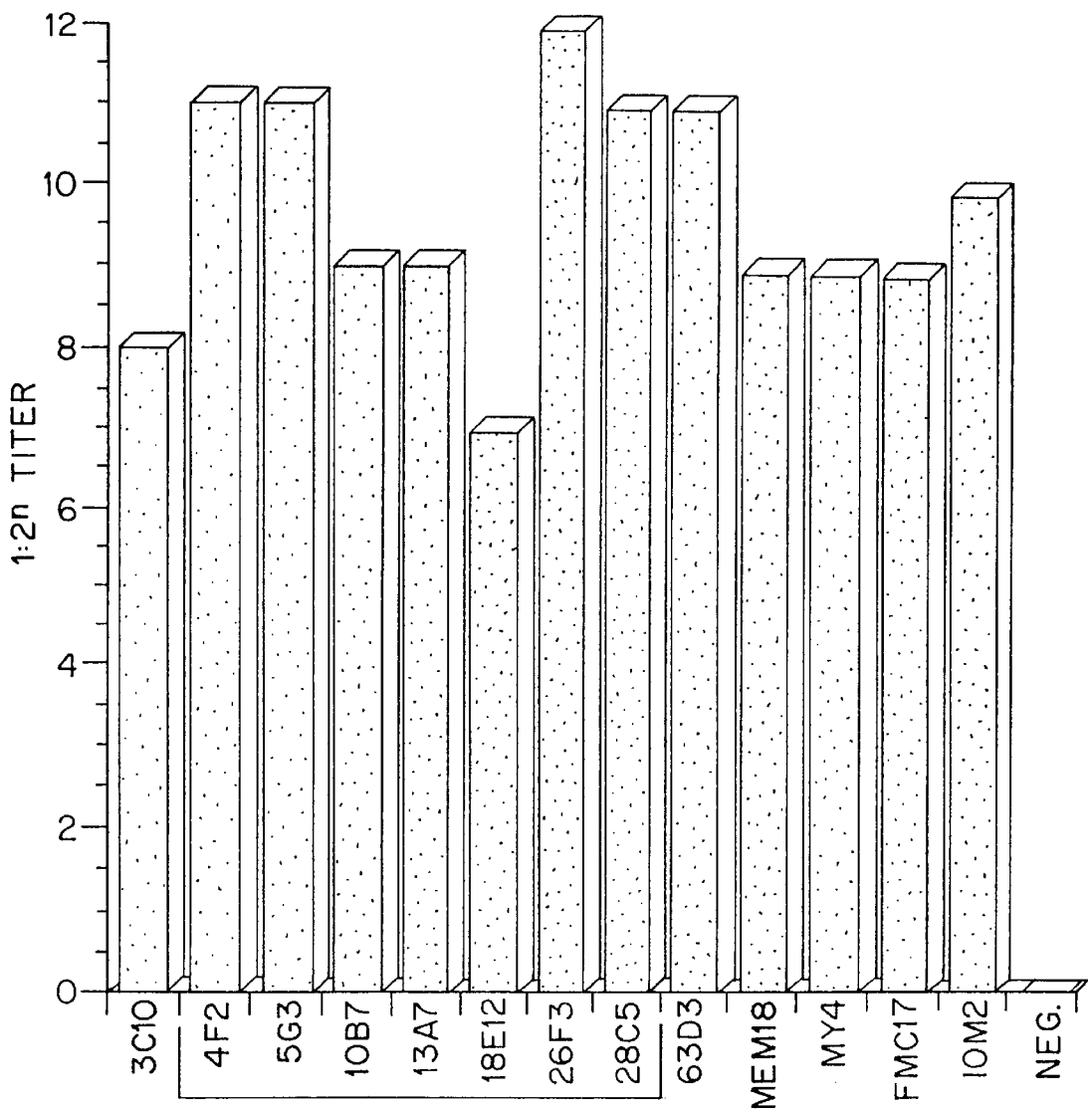
FIG. 11 shows the titers of various mAb to sCD14.

All anti-CD14 mAbs, and some commercially available anti-CD14s, were evaluated for antibody affinity to soluble CD14 antigen (FIG. 11). Antibody 3C10 had a titer of $1:2^8$ and 28CS a titer of $1:2^{11}$. This shows a eight-fold difference in titer of 28C5 as compared to 3C10. Relative affinities of the antibodies were determined at equivalent concentrations of purified antibody protein which were probed with a labeled goat anti-mouse conjugated antibody. Those antibodies with the highest affinity for sCD14, presented in this manner, are 4F2, 5G3, 26F3, 28C5, 23G4 and 63D3. Anti-CD14 mAbs 3C10 and 18E12 exhibited the lowest affinity for sCD14. Anti-CD14 28C5 had a much higher affinity as compared to 3C10. Soluble CD14 was coated onto microtiter plates and the anti-CD14 mAbs added in two-fold serial dilutions starting with 2 µg/ml. A goat anti-mouse HRP conjugated antibody is added and the plates incubated and washed. Substrate is then added and the $1:2^n$ titer is recorded. This is represented by the highest dilution of antibody giving at least 3× the $OD_{490\ nm}$ value of a negative control.

Figure 12:
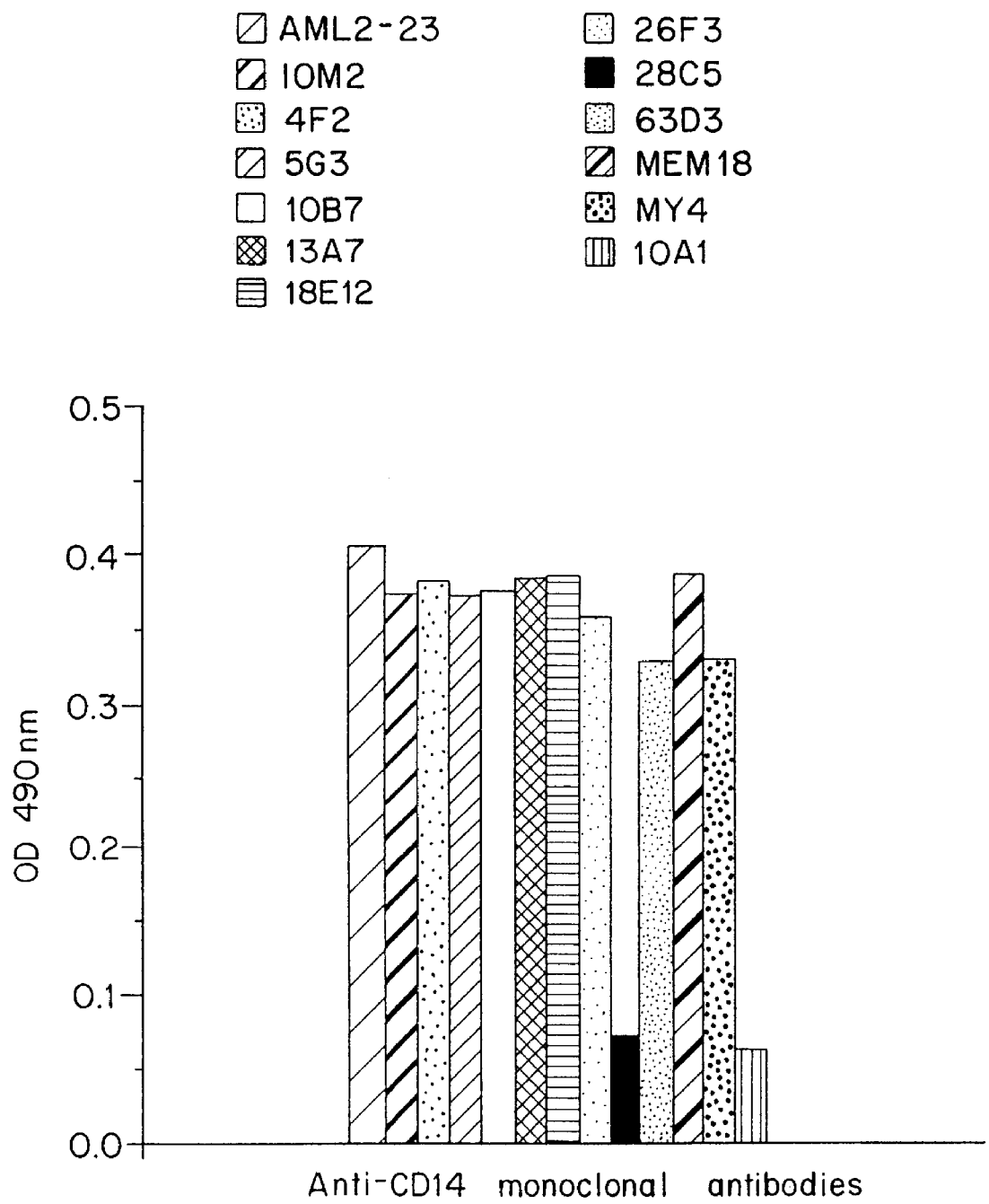
FIG. 12 shows the results of a competition assay between mAb 3C10 and a panel of anti-CD14 mAbs.

Competition studies between labeled 3C10 and a panel of anti-CD14 mAbs revealed that only antibodies 28C5 and 10A1 (an $I_gA$ mMab) were capable of competing with 3C10 for sCD14 on the coated microtiter plate (FIG. 12). Further competition assays were performed and confirmed that 18E12 did not compete with 28C5, 3C10, or 26F3.

Table 1 shows the results of a similar competition assay between 28C5, 23G4 and 18E12. The antibodies were coated on the solid phase in an ELISA assay with biotin labeled anti-CD14 mAbs (A,C).

TABLE 1

COMPETITION STUDIES BETWEEN DIFFERENT ANTI-CD14 MABS FOR CD14 RECOGNITION AND THE ABILITY OF THESE MABS TO BLOCK LPS/LBP BINDING TO CDI4

| Antibody | A<br>+18E12<br>% Inhibition | B<br>+28C5<br>% inhibition | C<br>+23G4<br>% inhibition | D<br>LPS Binding<br>% inhibition |
|---|---|---|---|---|
| 18E12 | 95.5 | 59.8 | 30.4 | 3.6 |
| 28C5 | 46.1 | 90.6 | 69.7 | 83.3 |
| 23G4 | 77.3 | 95.5 | 95.5 | 85.4 |

The ability of these anti-CD14 mAbs to block LPS/LBP binding to sCD14 was assessed using as similar ELISA format.

Figure 13:
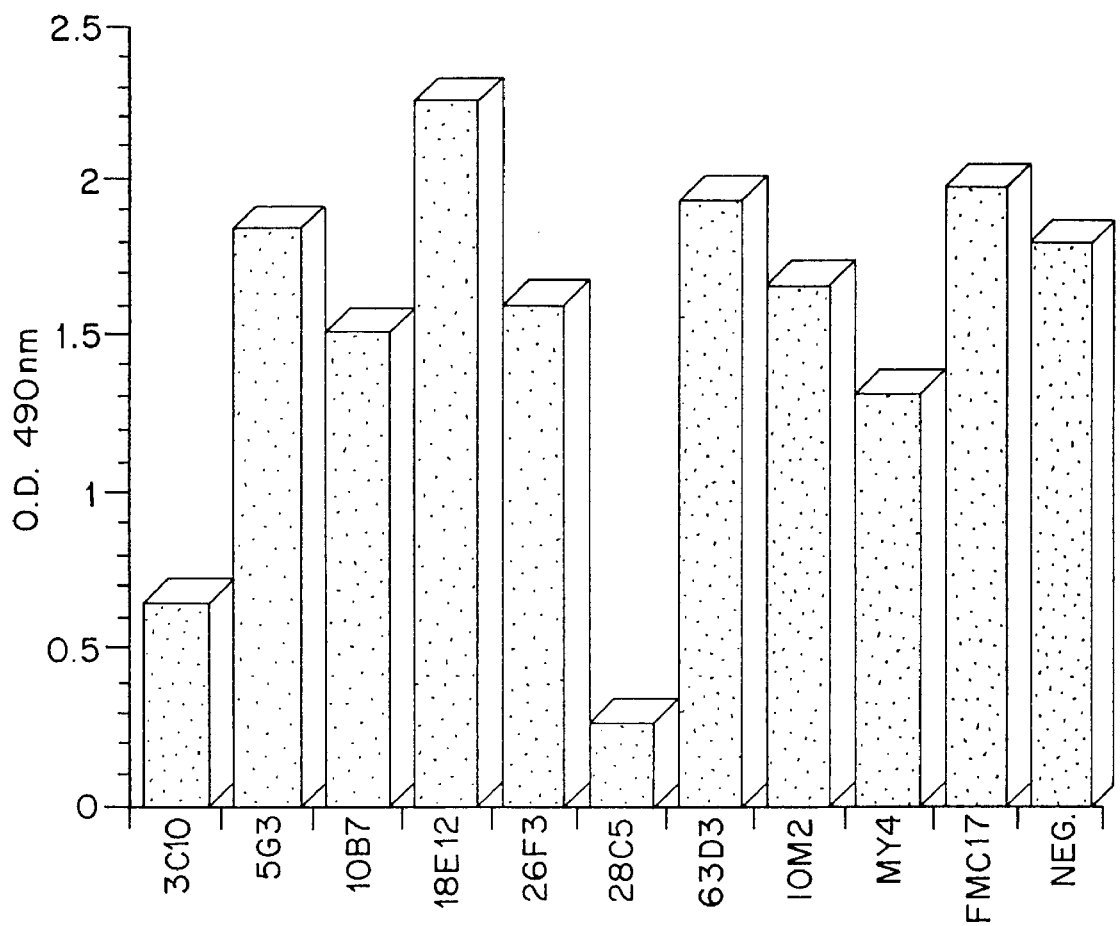
FIG. 13 shows the blocking of LPS/LBP binding to CD14 by anti-CD14 mAbs.

When the mAbs were evaluated for ability to inhibit LPS/LBP binding to sCD14, 28C5 was the most effective (FIG. 13). FIG. 13 represents the intensity of binding of LPB/biotinylated LPS complex to soluble CD14 immobilized on a solid phase, in the presence of 4 µg/ml of different anti-CD14 monoclonal antibodies. Anti-CD14 mAb 28C5 and 3C10 block this binding event. Anti-CD14 mAb is more efficient in its blocking as noted by the decreased OD value. Anti-CD14 mAb 18E12 does not exhibit any blocking effect.

Figure 14:
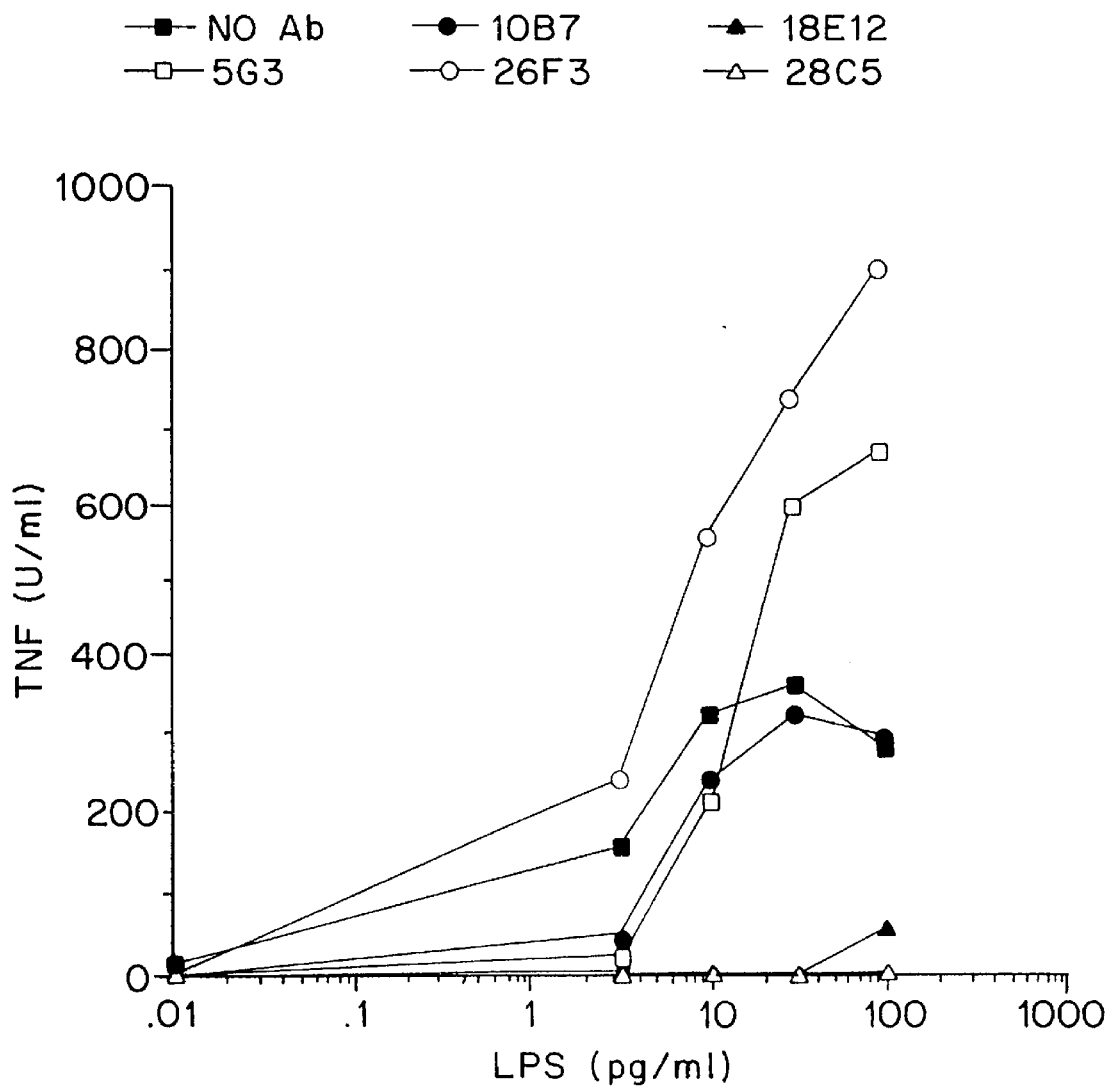
FIG. 14 shows the results of an evaluation of the ability of anti-CD14 mAbs to block cytokine release in HL-60 cells.
Figure 27:
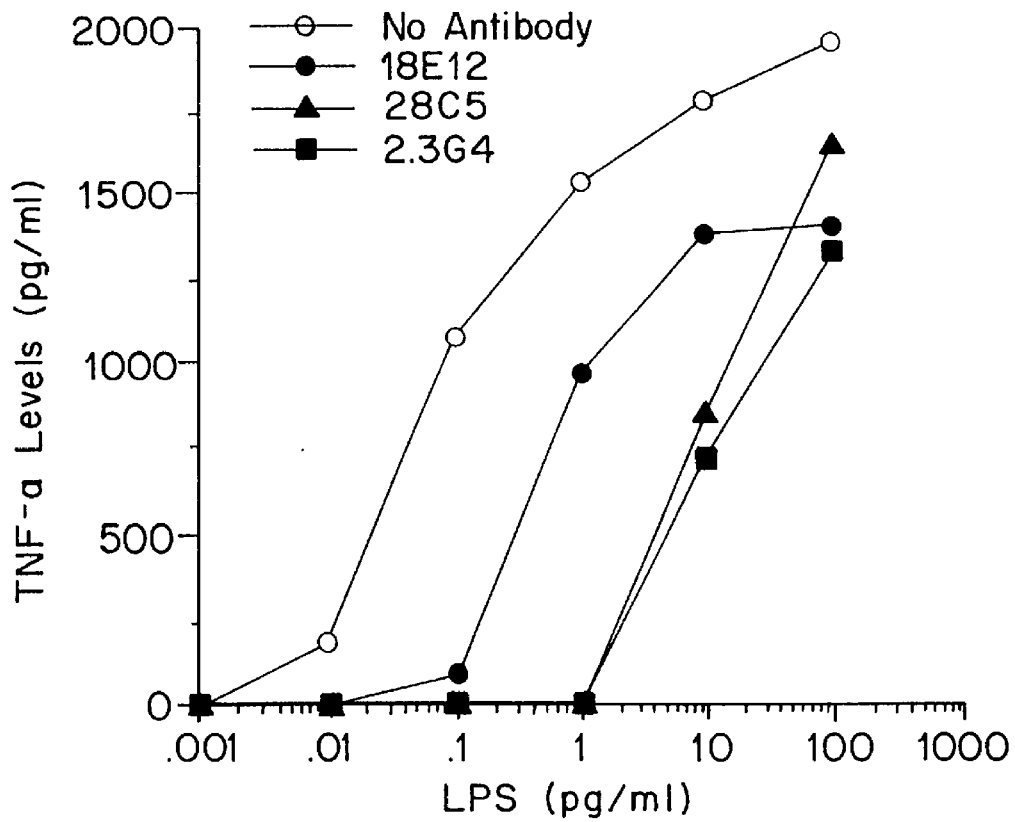
FIG. 27 shows inhibition of TNF release in human whole blood stimulated with LPS by treatment with 18E12 (●), 28C5 (▲) or 23G4 (■).
Figure 28:
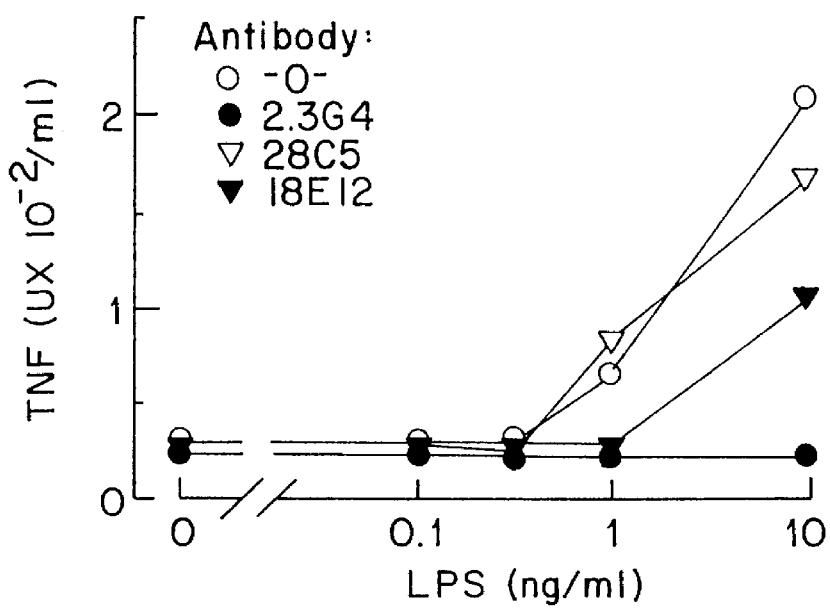
FIG. 28 shows the effect of anti-CD14 antibodies on LPS-induced TNF secretion in baboon blood. (23G4 (●), 28C5 (▽), and 18E12 (▼).

Evaluation of the anti-CD14 mAbs for the ability to block cytokine release in HL-60 cells in response to LPS stimulation, showed that 28C5 blocked TNF-α expression (FIG. 14). Inhibition of cytokine release was also observed when 28C5, 23G4, and 18E12 were added to whole blood ex vivo prior to addition of LPS. Surprisingly, 18E12 inhibited cytokine release even though it was previously demonstrated not to block LPS/LBP binding to CD14 (FIGS. 13 and 27). The effect of 23G4, 28C5 and 18E12 on LPS-induced TNF in baboon whole blood was also examined, ex vivo. The results in FIG. 28 show that 23G4 was most effective at inhibiting TNF secretion in LPS-induced baboon blood. These results show that 18E12 was specific for a domain on CD14 which did not prevent LPS/LBP binding, but is important to the signaling events involved in LPS stimulation of cells.

Although 28C5 and 23G4 share specificity in blocking binding of LPS:LBP to CD14, they do not share recognition of baboon CD14 (only 23G4 recognizes baboon), nor can 28C5 block TNFα release from baboon whole blood in response to LPS (FIG. 27).

The ability of the anti-CD14 mAbs, 28C5, 18E12 and 23G4 to block LPS/LBP binding to sCD14 was also assessed using a similar ELISA format as described for Table 1. The results also show that 23G4 and 28C5 compete for sCD14 binding (see Table 1).

C. Activation of Cytokine Release

HL-60 cells (obtained from the American Type Culture Collection, ATCC No. CCL-240 were plated at a concentration of 1.5×10⁵ cells per ml. The cells were induced toward the monocyte lineage for 3 to 4 days in RPMI 1640 containing 10% bovine serum, $10^{-7}M$ DHvD3 (Biomol Research Laboratories) and 50 µM indomethacin (Calbiochem). These differentiated cells were resuspended at 1×10⁶ cells/ml growth medium containing 50 µM indomethacin with or without 10% human type AB serum (Irvine Scientific) and then were added to flat bottom cluster dishes. Cells were activated by addition of different concentrations of LPS (E. coli serotype 01217:B8; Sigma) followed by a 4 to 5 hour incubation at 37° C. Cells in the culture plates were pelleted by low speed centrifugation (170×g for 10 minutes at room temperature) and the growth medium was removed for ELISA (ELISA kit for human TNF-α detection; Genzyme) of soluble cytokine levels.

D. Inhibition of LPS binding to Cellular CD14 by Anti-CD14 Monoclonal Antibodies To characterize the mechanism of interaction between cellular CD14 and LPS, stably transfected 70Z/3 cells containing the human CD14 expression vector described in Lee, et al., J. Exp. Med., 175:1697–1705, 1992, were prepared to form 70Z/3-hCD14 cells. Stably transfected cells expressing cell surface CD14 were confirmed using FACS analysis on cells stained with FITC conjugated anti-human CD14 Mab MY4 described earlier. Other transfected cell lines were also prepared expressing CD14 fusion proteins in which the membrane anchor from CD14 was removed and replaced with the membrane anchor from decay accelerating factor (DAF), designated 70Z/3-hCD14DAF, with the membrane anchor from human tissue factor, designated 70Z/3-hCD14TF, and with the membrane anchor from the murine class molecule, H2K², designated 70Z/3-hCD14CI.

Direct binding of LPS to cellular CD14 was characterized using FITC-labelled LPS (FITC-LPS). 70Z/3-CD14 cells were suspended in culture medium containing 10% FCS with or without 10 ug/ml Mab, and pre-incubated for 30 minutes at 37° C. Thereafter, FITC-Re595-LPS was added at 1 ng/ml and maintained for 15 minutes at 37° C. Immediately thereafter, an equal volume of ice-cold RPMI 1640 medium was added, and the admixture was maintained at 4° C. until FACS analysis. Cell-associated fluorescence was measured as described by Lee et al., supra, and measured fluorescence adjusted by subtracting fluorescence measured using non-transfected 70Z/3 cells.

Figure 15:
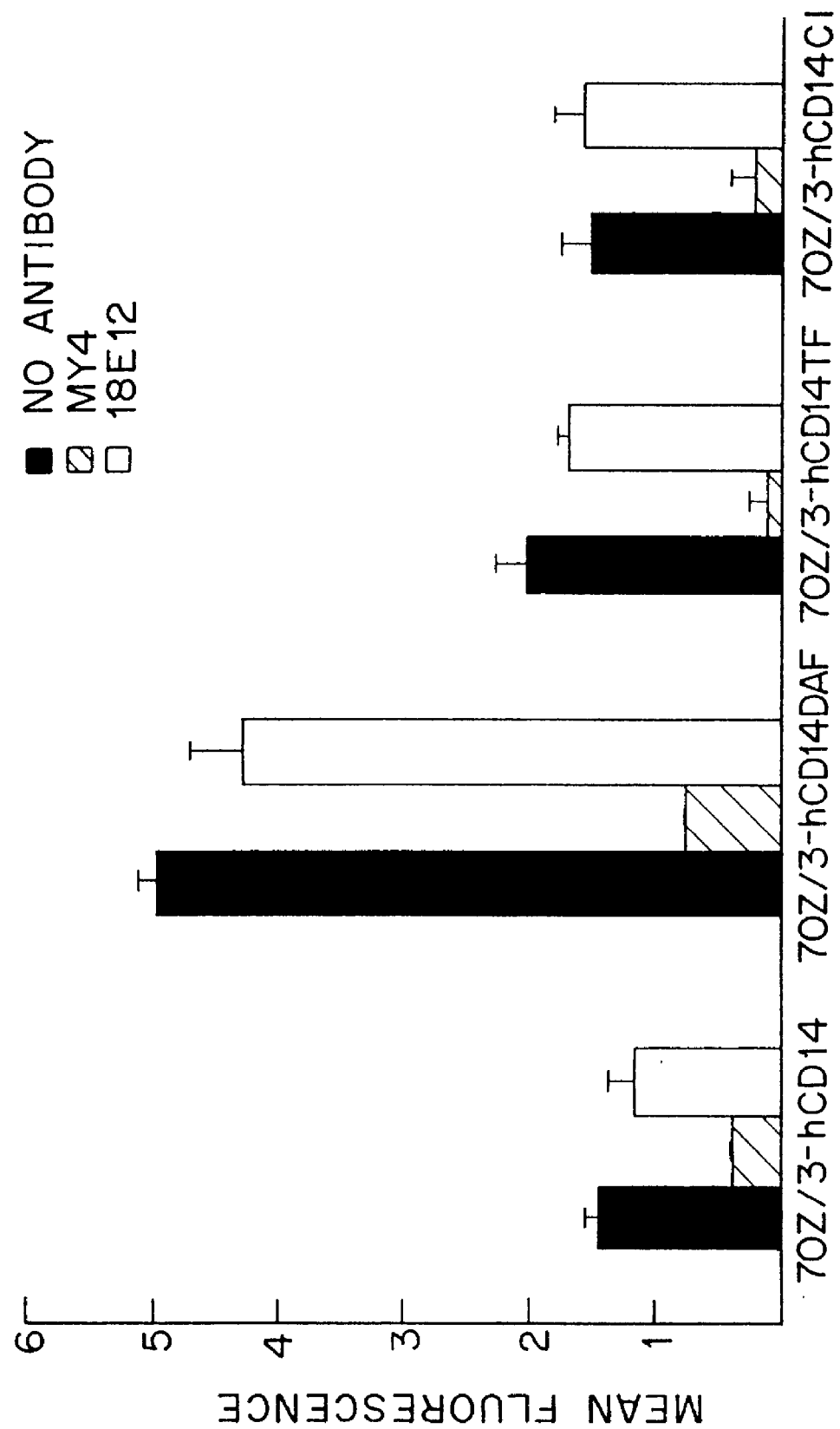
FIG. 15 shows effect of anti-CD14 mAbs to inhibit LPS binding to cellular CD14.

The bar-graph results are shown in FIG. 15, and indicate that for all transfected cell types that contain a cell-surface CD14 protein (wt or fusion protein), the anti-CD14 monoclonal antibody Mab MY4 (shaded bar) blocked LPS binding to cells, whereas Mab 18E12 (open bar) did not block LPS binding to cells. Binding of FITC-LPS in the presence of Mab 18E12 was similar to results obtained using no antibody (black bar). Mab MY4 is an antibody known to immunoreact with CD14, and by the data presented herein is shown to inhibit LPS binding to CD14 and to inhibit LPS-dependent, CD14-mediated cell activation. The differences in levels of FITC-LPS binding reflect the differences in levels of CD14 expression in the different transfected cell lines. Whereas the hCD14 transfected cells contain approximately 10,000 receptors per cell, the hCD14DAF transfected cells contain approximately 50,000 receptors per cell, and the hCD14Tf and hCD14CI transfected cells are estimated to each contain about 15,000–20,000 receptors per cell. The results are expressed as a mean ± standard deviation of three independent determinations.

E. Inhibition of LPS-Dependent, CD14-Mediated Activation of Cells using Anti-CD14 Monoclonal Antibodies Anti-CD14 monoclonal antibodies were characterized for their ability to inhibit CD14-mediated activation of cells by LPS. To that end, a CD14 transfected cell system was developed and demonstrated to be responsive to LPS-induced activation. Several transfected 70Z/3 cell lines were prepared as described in Example 3, and contain several membrane associated forms of CD14 as described earlier.

Figure 16:
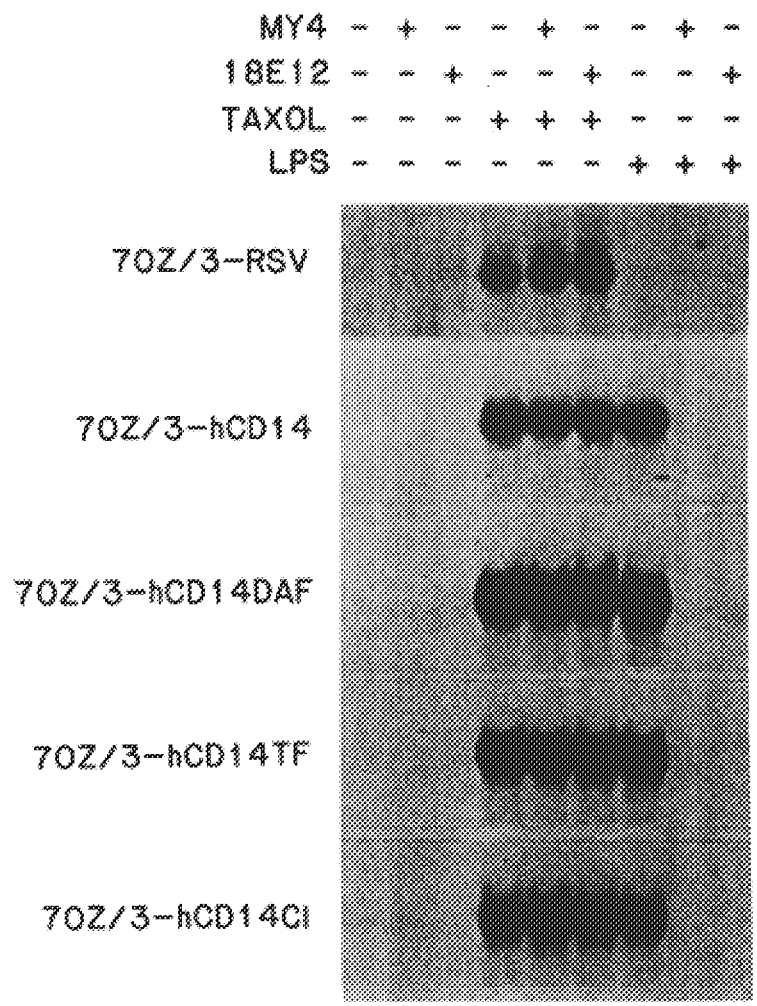
FIG. 16 shows effect of anti-CD14 mAbs on LPS-dependent, CD14-mediated activation of cells.

The transfected cells were cultured as described by Lee et al., supra, suspended in RPMI 1640 media containing 10% fetal calf serum (FCS; heat inactivated, 56° C. for 30 min.) and 10 ug/ml antibody (MY4 or 18E12) as indicated by a "+" in FIG. 16, and maintained for 30 min at 37° C. Thereafter, 100 uM taxol or LPS (1 ng/ml Re595 LPS) was added as indicated by a "+" in FIG. 16 and the cells were maintained for 15 min at 37° C. Thereafter, the cells were harvested and nuclear extracts was prepared to determine activation of NF-κB as described by Molitor et al., Proc. Natl. Acad. Sci. USA, 87:10028–10032 (1990). $P^{32}$-labelled NF-κB-specific oligonucleotides (5'-CAGAGGGGACTTTCCGAGA-3') in double-stranded form were used in a gel retardation assay to detect the presence of NF-κB on 4% non-denaturing polyacrylamide gels.

The results of the study are shown in FIG. 16, and indicate that LPS and taxol both induce NF-κB activation. As expected, LPS induced minimal NF-κB activation in control transfected cells lacking CD14 (70Z/3-RSV), and induced marked activation in cells expressing CD14. This shows that LPS-induced NF-κB activation is mediated by and requires CD14 on the cell surface. Furthermore, the results show that both MY4 and 18E12 inhibit LPS-induced NF-κB expression, but not taxol-induced NF-κB expression, indicating that the inhibitory effect of the antibodies is specific and dependent upon CD14.

These results with Mabs MY4 and 18E12 indicate that LPS binding to CD14 is not sufficient to induce cell activation and that additional interactions following LPS-CD14 binding are critical for cell activation. The results also indicate that inhibition of CD14-mediated activation of cells may occur at different levels, first by blocking the inducer (LPS) from binding to CD14, and second by blocking a subsequent step after inducer binds to CD14. The data also establish that the use of inhibitors of the second step will block CD14-mediated cell activation where the inducer is a molecule other than LPS.

F. Inhibition of LPS Uptake by $CD14^+$ Cells

In the progression of sepsis, LPS binds cell surface CD14, and is known to be taken up by those $CD14^+$ cells (Kitchens, et al., J. Exp. Med., 176:485–494, 1992; Pugin, et al., PNAS, 90:2744–2748, 1993). The difference between antibodies that block LPS binding to CD14, such as Mab 28C5, and antibodies that do not block binding to CD14, such as Mab 18E12, is significant in view of LPS uptake by $CD14^+$ cells. Therefore, the ability of anti-CD14 antibodies to inhibit LPS uptake was characterized.

To that end, FITC-LPS uptake on transfected 70Z/3-hCD14 cells was measured in the presence of various anti-CD14 antibodies. Fluorescence arising from the FITC-LPS was detected inside $CD14^+$ transfected cells when no antibody was utilized after the cells were maintained at 37° C. following exposure to FITC-LPS, confirming that LPS is taken up by cells under normal conditions. In the presence of Mab 28C5, uptake of LPS could be inhibited completely, whereas in the presence of Mab 18E12, uptake could only be reduced to about 65% of the amount of uptake observed under normal conditions. These results indicate that Mab 18E12 is particularly useful for inhibiting $CD14^+$ cell activation where it is desirable to allow LPS to enter the cells, because Mab 18E12 does not substantially prevent LPS uptake. Subsequent studies show that in the presence of Mab 23G4, uptake of LPS could be inhibited similar to that seen with Mab 28C5.

| CD14 Antigen Assay (ELISA) | |
|---|---|
| Coating: | 150 μl/well of anti-CD14 mAb 28C5 diluted at 1 μg/ml in bicarbonate buffer. Incubate overnight at 4° C. |
| Blocking: | Wash the plate 4× then add 150 μl/well of blocking buffer. Incubate 1 hr. at 37° C. |
| Samples: | Wash the plate 1× then add 125 μl/well of samples diluted in dilution buffer. Incubate 1 hr. at 37° C. |
| Conjugate: | Wash the plate 5× then add 0.100 ml/well of biotinylated anti-CD14 mAb 18E12 diluted at 1 μg/ml in dilution buffer. Incubate 1 hr. at 37° C. |
| Av-HRPO: | Wash the plate 5× then add 0.100 ml/well of preformed streptavidin/biotin/peroxidase complex. (Streptavidin/biotinylated/HRPO preparation (Zymed SABC kit): Mix 2 μl/ml of Streptavidin with 2 μl/ml of biotinylated-HRPO in washing buffer and incubate 30 minutes at 37° C. Before adding to the wells, dilute at 1:2 with dilution buffer.) Incubate 30 minutes at 37° C. |
| Substrate: | Wash the plate 5× then add 0.100 ml/well of Sigma OPD, leave the plate 30 minutes in the dark and stop the color development with 0.050 ml of 4N H2SO4. Read plate at 490 nm. |
| CD14 Standard: | 2-fold serial dilutions of clone 523 at 100 ng/ml. |
| Serum Dilutions: | Starting dilution 1:25–1:50. |
| Miscellaneous ELISA Reagents | |
| Blocking Buffer: | PBS + 10% w/v of nonfat dry milk (Carnation). |
| Washing Buffer: | PBS + 0.05% v/v of Tween 20. |
| Dilution Buffer: | Mix vol/vol blocking buffer and wash buffer, use to dilute samples, labelled antibody and the preformed complex. |

EXAMPLE 3

MONOCLONAL ANTIBODY CLONING

Messenger RNA was extracted from monoclonal antibody producing cell lines using the method of Chomczynkski and Sacchi, *Anal. Bio.,* 162:156–159 (1987), incorporated herein by reference. Reverse transcription was performed using murine specific 3" antibody primers (IgG1 or k) and the resulting cDNAs subjected to PCR (Supplier) according to the manufacturer's instructions, using a panel of murine specific 5' antibody primers described in Huse, et al., *Science,* 246:1275–1281 (1989), incorporated herein by reference. Heavy and light chain DNA fragments were gel purified and digested with appropriate enzymes. The 672 base pair heavy chain fragment was cloned into the Spe1/Xho1 site of pBluescript II KS$^+$ and sequenced using the automated ABI Model 373A DNA sequencer, according to the manufacturer's instructions. The 642 base pair light chain fragment was cloned into the Sst1/Xba of pBluescript II KS$^+$ and sequenced in a similar manner.

SEQ ID NO:1 and 2 are the nucleotide and deduced amino acid sequence of the 28C5 heavy chain and SEQ ID NO:3 and 4 are the nucleotide and deduced amino acid sequence of the 28C5 light chain. SEQ ID NO:5 and 6 are the the nucleotide and deduced amino acid sequence of the 18E12 heavy chain and SEQ ID NO:7 and 8 are the nucleotide and deduced amino acid sequence of the 18E12 light chain (FIGS. 2–5). FIG. 30 shows a comparison of the heavy chains of 3C10, 28C5 and 18E12. SEQ ID NO:25 and 26 are the nucleotide and deduced amino acid sequence of the 23G4 light chain (See FIG. 29). FIG. 29 shows the amino acid sequence of the light chains of monoclonal antibodies 3C10, 28C5, 23G4 and 18E12. FIG. 30 shows the amino acid sequence of the heavy chains of monoclonal antibodies 3C10, 28C5, and 18E12.

Note that although both 28C5 and 23G4 share the same specificity in that they block LPS:LBP binding to CD14, compete with each other for sCD14 binding and prevent TNFα release in human whole blood at similar concentrations (see FIG. 27), their light chains do not share the same nucleotide and amino acid sequence. (See Table 2).

Recombinant Expression of Nucleic Acids

The recombinant expression of nucleic acids of this invention are performed according to the following general strategy. PolyA$^+$ mRNA is isolated from the antibody-expressing hybridoma cells. cDNA synthesis and PCR amplification of the mRNA are performed by methods described above. From the CDNA sequence data obtained, the amino acid sequences of the polypeptides encoded by the DNA sequences are deduced by a computer software program, for example, MAPSEQ, commercially available from DNAStar (Madison, Wis.).

The expression products, assembled as an antibody fragment, are screened for binding affinity by methods known in the art such as ELISAs (Enzyme-Linked Immuno-Sorbent Assay) utilizing the hapten or antigen, or affinity columns (as described, for example, in Skerra and Pluckthun, *Science,* 240:1038–1041, 1988, incorporated herein by reference).

Several types of vectors are available and can be used to practice this invention, e.g., plasmid, DNA and RNA viral vectors, baculoviral vectors, and vectors for use in yeast. When the vector is a plasmid, it generally contains a variety of components including promoters, signal sequences, phenotypic selection genes, origin of replication sites, and other necessary components as are known to those of skill in the art.

Promoters most commonly used in prokaryotic vectors include the lac Z promoter system, the alkaline phosphatase pho A promoter, the bacteriophage λPL promoter (a temperature sensitive promoter), the tac promoter (a hybrid trp-lac promoter that is regulated by the lac repressor), the tryptophan promoter, and the bacteriophage T7 promoter.

Promoters used to practice this invention are the lac Z promoter and the pho A promoter. The lac Z promoter is regulated by the lac repressor protein lac i, and thus transcription of the polypeptide can be controlled by manipulation of the level of the lac repressor protein. By way of illustration, a phagemid containing the lac Z promoter is grown in a cell strain that contains a copy of the lac i repressor gene, a repressor for the lac Z promoter. Exemplary cell strains containing the lac i gene include JM 101 and XL1 -blue. In the alternative, the host cell can be cotransfected with a plasmid containing both the repressor lac i and the lac Z promoter. Occasionally both of the above techniques are used simultaneously, that is, phagmid particles containing the lac Z promoter are grown in cell strains containing the lac i gene and the cell strains are cotransfected with a plasmid containing both the lac Z and lac i genes. Normally when one wishes to express a gene, to the transfected host above, one would add an inducer such as isopropylthiogalactoside (IPTG), but this step can be omitted.

Another useful component of vectors used to practice this invention is a signal sequence. This sequence is typically located immediately 5' to the gene encoding the polypeptide, and thus will be transcribed at the amino terminus of the fusion protein. However, in certain cases, the signal sequence has been demonstrated to be located at positions other than 5' to the gene encoding the protein to be secreted. This sequence targets the protein to which it is attached across the inner membrane of the bacterial cell. The DNA encoding the signal sequence can be obtained as a restriction endonuclease fragment from any gene encoding a protein that has a signal sequence. Suitable prokaryotic signal sequences can be obtained from genes encoding, for example, LamB or OmpF (Wong, et al., *Gene,* 68:193, 1983, incorporated herein by reference), MalE, PhoA, OmpA and other genes. A preferred prokaryotic signal sequence for practicing this invention is the *E. coli* heat-stable enterotoxin II (STII) signal sequence as described by Chang, et al., *Gene,* 55:189, 1987, incorporated herein by reference.

Another useful component of the vectors used to practice this invention is a phenotypic selection gene. Typical phenotypic selection genes are those encoding proteins that confer antibiotic resistance upon the host cell. By way of illustration, the ampicillin resistance gene (amp), and the tetracycline resistance gene (tet) are readily employed for this purpose.

Construction of suitable vectors comprising the aforementioned components as well as the gene encoding the desired polypeptide are prepared using standard recombinant DNA procedures. References for recombinant methodology have been provided infra. Isolated DNA fragments to be combined to form the vector are cleaved, tailored, and ligated together in a specific order and orientation to generate the desired vector.

The DNA is cleaved using the appropriate restriction enzyme or enzymes in a suitable buffer. In general, about 0.2–1 μg of plasmid or DNA fragments is used with about 1–2 units of the appropriate restriction enzyme in about 20 μof buffer solution. Appropriate buffers, DNA concentrations, and incubation times and temperatures are specified by the manufacturers of the restriction enzymes. Generally, incubation times of about one or two hours at 37° C. are adequate, although several enzymes require higher temperatures. After incubation, the enzymes and other contaminants are removed by extraction of the digestion solution with a mixture of phenol and chloroform and the DNA is recovered from the aqueous fraction by precipitation with ethanol.

To ligate the DNA fragments together to form a functional vector, the ends of the DNA fragments must be compatible with each other. In some cases, the ends will be directly compatible after endonuclease digestion. However, it may be necessary to first convert the sticky ends commonly produced by endonuclease digestion to blunt ends to make them compatible for ligation. To blunt the ends, the DNA is treated in a suitable buffer for at least 15 minutes at 15° C. with 10 units of the Klenow fragment of DNA polymerase I (Klenow) in the presence of the four deoxynucleotide triphosphates. The DNA is then purified by phenol-chloroform extraction and ethanol precipitation.

The cleaved DNA fragments are size-separated and selected using DNA gel electrophoresis. The DNA is electrophoresed through either an agarose or a polyacrylamide matrix. The selection of the matrix will depend on the size of the DNA fragments to be separated. After electrophoresis, the DNA is extracted from the matrix by electroelution, or, if low-melting agarose is used as the matrix, by melting the agarose and extracting the DNA from it.

The DNA fragments that are to be ligated together (previously digested with the appropriate restriction enzymes such that the ends of each fragment to be ligated are compatible) are put in solution in about equimolar amounts. The solution will also contain ATP, ligase buffer and a ligase such as T4 DNA ligase at about 10 units per 0.5 mg of DNA. If the DNA fragment is to be ligated into a vector, the vector is at first linearized by cutting with the appropriate restriction endonuclease(s). The linearized vector can then be treated with alkaline phosphatase or calf intestinal phosphatase. The phosphatasing prevents self-ligation of the vector during the ligation step.

After ligation, the vector with the foreign gene now inserted is transformed into a suitable host cell. Suitable prokaryotic host cells include E. coli strain JM101, E. coli K12 strain 294 (ATCC number 31,446), E. coli strain W3110 (ATCC number 27,325), E. coli X1776 (ATCC number 31,537), E. coli XL-1 Blue (Stratagene), and E. coli B; however, many other strains of E. coli, such as HB101, NM522, NM538, NM539 and many other species and genera of prokaryotes can be used as well. In addition to the E. coli strains listed above, bacilli such as Bacillus subtillis, other enterobacteriaceae such as Salmonella typhimunium or Serratia marcesans and various Pseudomonas species can all be used as hosts.

Transformation of prokaryotic cells is readily accomplished using calcium chloride or other methods well known to those skilled in the art. Electroporation (Neumann, et al., EMBO J., 1:841 1982, incorporated herein by reference) also can be used to transform these cells. The transformed cells are selected by growth on an antibiotic, commonly tetracycline (tet) or ampicillin (amp), to which they are rendered resistant due to the presence of tet and/or amp resistance genes on the vector.

After selection of the transformed cells, these cells are grown in culture and the plasmid DNA (or other vector with the foreign gene inserted) is then isolated. Plasmid DNA can be isolated using methods known in the art. This purified plasmid DNA is then analyzed by restriction mapping and/or DNA sequencing.

Following procedures outlined above, mammalian cell lines such as myeloma (P3-653), hybridoma (SP2/0), Chinese Hamster Ovary (CHO), Green monkey kidney (COS1) and murine fibroblasts (L492) are suitable host cells for polypeptide expression. These "mammalian" vectors can include a promoter, an enhancer, a polyadenylation signal, signal sequences and genes encoding selectable markers such as geneticin (neomycin resistance), mycophenolic acid (xanthine guanine phosphoribosyl transferase) or histidinol (histidinol dehydrogenase).

Suitable promoters for use in mammalian host cells include, but are not limited to, Ig Kappa, Ig Gamma, cytomegalovirus (CMV) immediate early, Rous Sarcoma Virus (RSV), simian virus 40 (SV40) early, mouse mammary tumor (MMTV) virus and metallothionein. Suitable enhancers include, but are not limited to Ig Kappa, Ig Heavy, CMV early and SV40. Suitable polyadenylation sequences include Ig Kappa, Ig Gamma or SV40 large T antigen. Suitable signal sequences include Ig Kappa, Ig Heavy and human growth hormone (HGH).

When the vector is baculovirus, suitable promoters and enhancer sequences include, but are not limited to AcMNPV polyhedrin, AcMNPV ETL and AcMNPV p10 sequences. One particularly suitable polyadenylation signal is the polyhedrin AcMNPV. Ig Kappa, Ig Heavy and AMNPV are examples of suitable signal sequences. These vectors are useful in the following insect cell lines, among others: SF9, SF21 and High 5.

Alternatively, the polypeptides can be expressed in yeast strains such as PS23-6A, W301-18A, LL20, D234-3, INVSC1, INVSC2, YJJ337. Promoter and enhancer sequences such as gal 1 and pEFT-1 are useful. Vra-4 also provides a suitable enhancer sequence. Sequences useful as functional "origins of replication" include ars1 and 2μ circular plasmid.

TABLE 2

AMINO ACID SEQUENCE ANALYSIS OF ANTI-CD14 mAbs CDRs

| MAb | CDR1 | CDR2 | CDR3 |
|---|---|---|---|
| 3C10-Heavy | SYAMS | SISSGGTTYYPDNVKG | GYYDYHY |
|  | (SEQ ID NO: 10) | (SEQ ID NO: 11) | (SEQ ID NO: 12) |
| 28C5-Heavy | SDSAWN | YISYSGSTSYNPSLKS | GLRFAY |
|  | (SEQ ID NO: 13) | (SEQ ID NO: 14) | (SEQ ID NO: 15) |
| % homology | 17% | 38% | 14% |
| 3C10-Light | RASESVDSFGNSFMH | RAANLES | QQSYEDPWT |
|  | (SEQ ID NO: 16) | (SEQ ID NO: 17) | (SEQ ID NO: 18) |
| 28C5-Light | RASESVDSYVNSFLH | RASNLQS | QQSNEDPYT |
|  | (SEQ ID NO: 19) | (SEQ ID NO: 20) | (SEQ ID NO: 21) |
| 23G4-Light | RASESVDSYGKSFMH | VASKLES | QQNNEDPYT |
|  | (SEQ ID NO: 22) | (SEQ ID NO: 23) | (SEQ ID NO: 24) |
| % homology | 80% | 71% | 67% |

EXAMPLE 4

IN VIVO TREATMENT WITH CD14 ANTIBODIES

The pretreatment of rabbits with IFN-γ for three days followed by an injection of LPS produces a sepsis state in rabbits (G. J. Jurkovich, et al., *J. Surg. Res.*, 51:197–203, 1991). A similar protocol was followed in the in vivo experiments described herein. 5 μg/kg of IFN-γ (specific activity: $2.5 \times 10^8$ units/mg; 5 μg=$1.25 \times 10^6$ units/kg) was injected daily for three consecutive days, then following establishment of baseline cardiac output and systemic pressure, an 8 hour infusion of LPS (3 mg/kg total dose or 375 μg/kg/hour×8 hours) was started. Subcutaneous injections of IFN-γ were given 3 days and on the 3rd day baseline data was collected for at least one hour prior to starting the infusion of LPS. These animals were maintained on ketamine throughout the experiment. The rabbit experiments suggested that these animals will become somnolent following the LPS infusion. The same established protocol was also utilized in two groups of monkeys. Animals were randomly assigned to either isotype matched control monoclonal antibodies (MAbs) or a CD14 blocking MAb with the person responsible for their care unaware of the treatment protocol. A dose of 5mg/kg/mAb (isotype or CD14specific) was given by bolus injection 30' prior to the start of the LPS infusion.

Animals were anesthetized with ketamine then arterial and venous catheters placed in the femoral artery and vein, respectively. The arterial catheter has a thermistor at its tip for determination of thermal dilution cardiac output. A second lumen on this catheter was used for arterial pressure measurement. The venous catheter was used to infuse drugs, maintenance fluids and for cold injection in the cardiac output measurements. Lactated Ringers (3 ml) was used for each cardiac output determination.

Blood pressure and cardiac output was recorded every 15 minutes throughout the baseline period and then every half hour for the remainder of the experiment. Blood was drawn (3 ml) every hour for determination of arterial $PO_2/PCO_2$, pH and protein. This same blood sample was used for determination of systemic white blood cell counts and differential counts. These animals were resuscitated with lactated Ringers' solution following the infusion of LPS. All animals were given an infusion of 4 mls/kg as a maintenance infusion and this was increased as necessary to maintain cardiac output to within 10% of baseline.

A total of six animals each were pretreated with either the IgG1 isotype control or 28C5, and five animals were pretreated with 18E12. All test animals were challenged with LPS 30 minutes after the infusion of antibody. Seventy-two hours prior to LPS infusion, monkeys were given 3 subcutaneous injections of human recombinant interferon gamma (125,000 U/Kg) at 24 hour intervals. To measure MAP levels in anesthetized animals, arterial and venous catheters were placed in the femoral artery and vein, respectively as described above.

Mean Arterial Pressure (MAP) of Monkeys Challenaed with LPS

The mean arterial pressure (MAP) results reveal that pretreatment with 28C5 prevented a significant drop in blood pressure, particularly at the 2 hour time point, common in the control group (FIG. 17). However, animals pretreated with 18E12 exhibited this drop in blood pressure at 2 hours, yet were able to recover to percents noted in the 28C5 pretreated animals. The function of 18E12 differs from that of 28C5 in that only signaling events are prevented, not inhibition of LPS binding; a key feature of 28C5 as well as 23G4. This difference in function may reflect the difference noted in the MAP response. Protection by 18E12 may involve late LPS-induced effects. This MAP profile by 18E12 suggests that even in the event of physiological responsiveness to LPS (presence of hypotension) this anti-CD14 mAb is capable of preventing the deleterious effects noted in the isotype control-treated animals.

Effect of IFN On CD14 Concentration

Figure 18A:
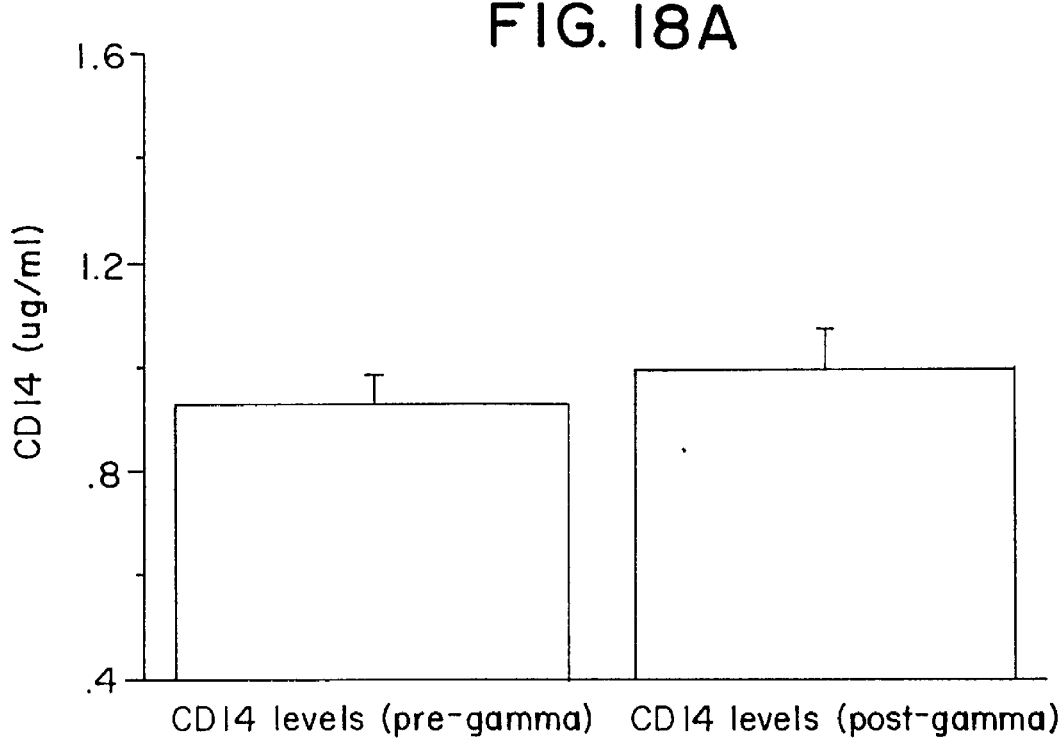
FIGS. 18A–B show pre and post human IFN-γ treatment CD14 levels and LBP levels in a monkey.
Figure 18B:
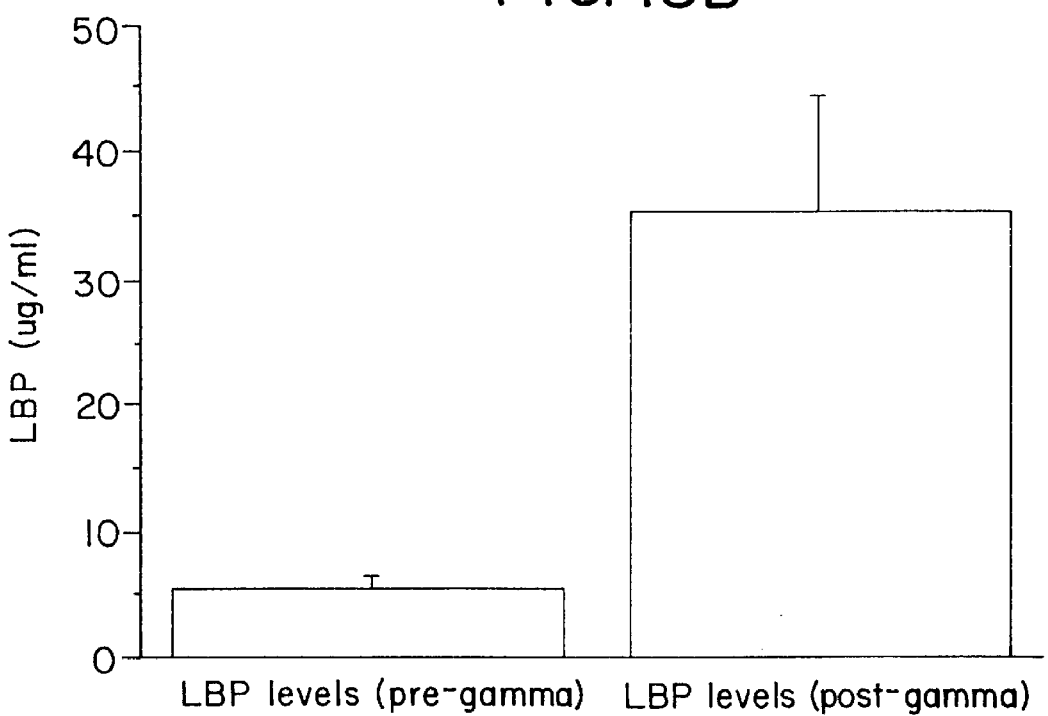

The pretreatment of animals with interferon-gamma for three consecutive days, 24 hours apart, had relatively little effect on the CD14 concentration (FIG. 18). However, the circulating levels of lipopolysaccharide binding protein (LBP) increased significantly (LBP was measured by ELISA in which two non-competing monoclonal antibodies were used to capture and probe test samples); to levels noted during gram-negative sepsis. It is proposed that the interferon-gamma induces an acute phase response and sensitizes the animals to doses of LPS which otherwise would not induce any physiological and/or biochemical changes in these animals.

Lavage/Plasma Ratio of BSA

Figure 19:
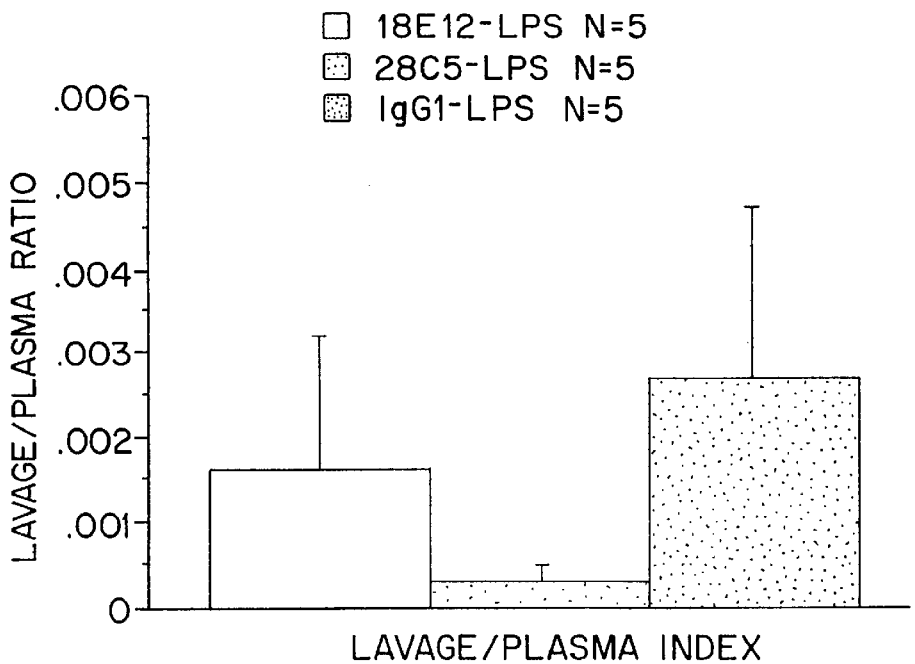
FIG. 19 shows the lavage/plasma ration of BSA in monkeys treated with 18E12, 28C5 or IgG1.

The Lavage/Plasma ratio of BSA is an indicator of lung damage and accesses the amount of BSA (injected one hour prior to the termination of the experiment) that permeates the lung tissue. The lung is one of the primary organs affected during endotoxemia. BSA levels were determined by an immunoassay utilizing a BSA specific monoclonal antibody. BSA monoclonal antibodies are widely available. In this instance, the animals pretreated with 28C5 were protected significantly from the lung damage that was evident in the control-treated group (FIG. 19). While 18E12-treated animals were not fully protected from the LPS effects, as a group they did better than the control animals.

Antibody Half-Life

Figure 20:
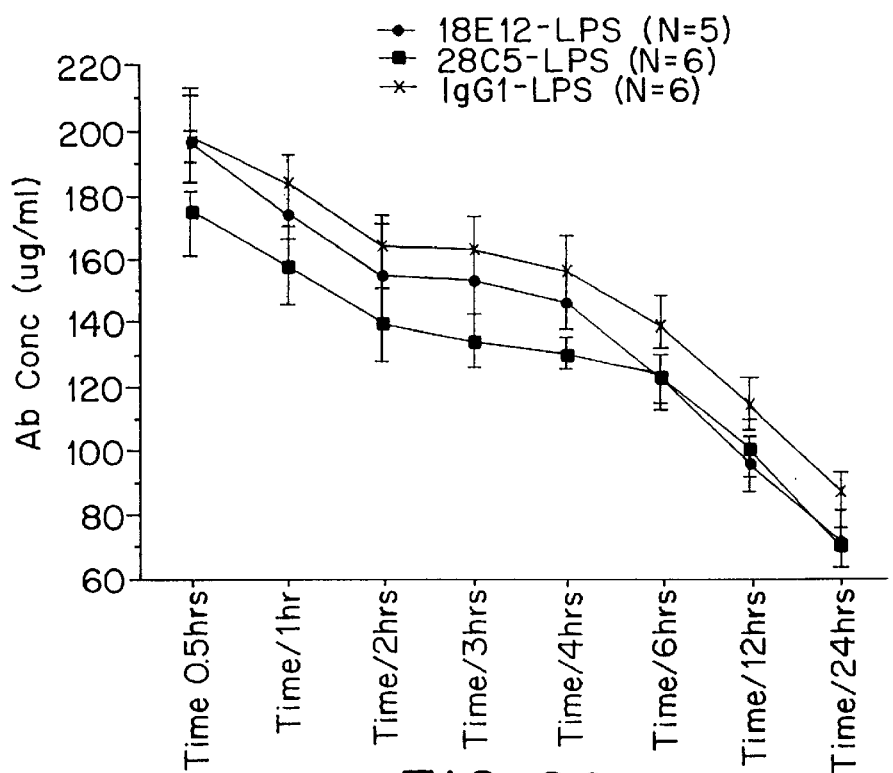
FIG. 20 shows the antibody half life of 18E12, 28C5 and IgG1 in monkeys.

A question arises as to the antibody half-life, or fate of the antibody due to its binding to both the soluble circulating form of CD14 and the membrane-associated CD14 present on monocytes and neutrophils. When compared to an isotype control antibody which does not recognize human antigens, the kinetics of clearance are similar for all three groups (FIG. 20).

CD14 Levels in Monkeys Treated With Antibody

Figure 21A:
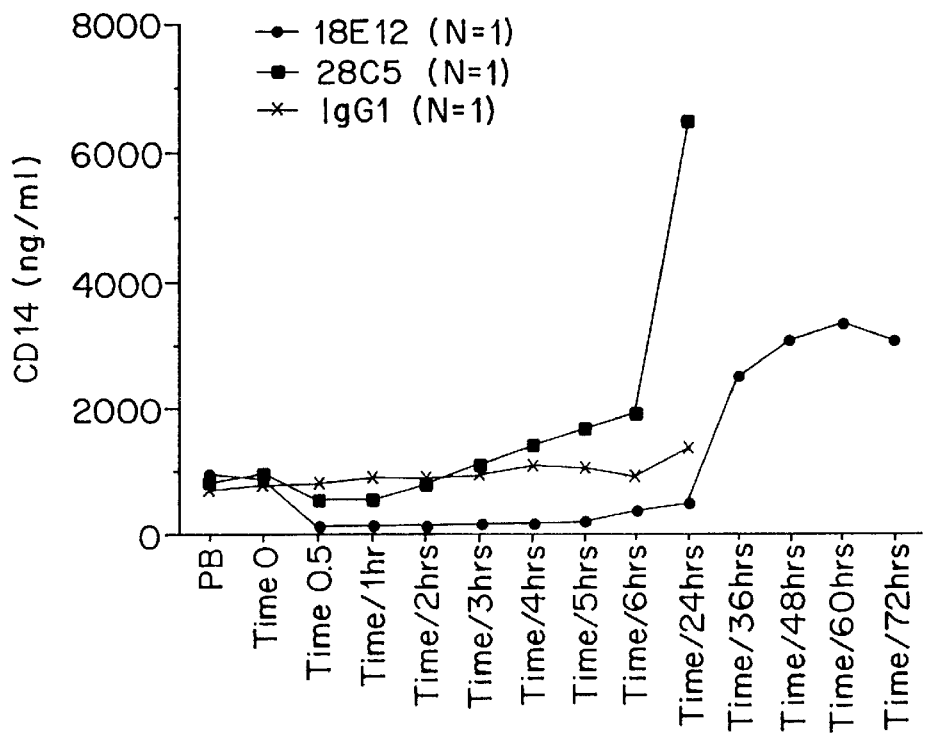
FIGS. 21A–B show CD14 levels in monkeys treated with antibody (18E12, 28C5 and IgG1) alone (top) or challenged with LPS after antibody treatment (bottom).
Figure 21B:
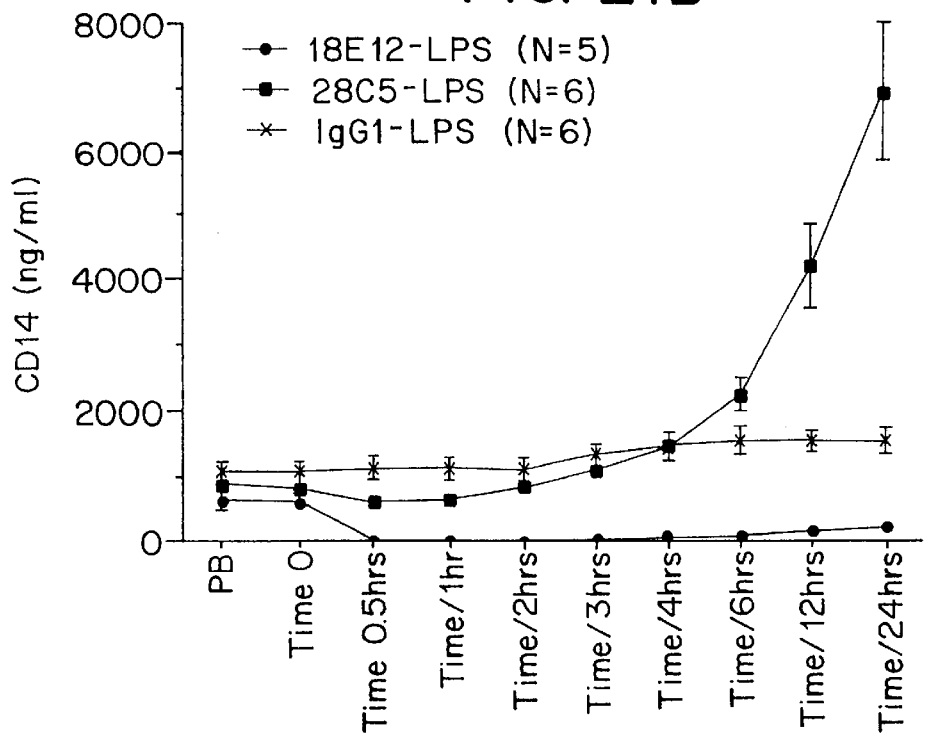

CD14 was measured by ELISA in which two non-competing monoclonal antibodies are used to capture and probe test samples. The CD14 levels in monkeys treated with antibody only (no LPS challenge) were significantly higher in the 28C5 versus the control-treated animals (FIG. 21). The reason for this rise is unknown although in vitro studies demonstrated that exposure of CD14-bearing cells to anti-CD14 mAb 28C5 resulted in higher sCD14 levels; perhaps the antibody enhances the shedding mechanism of this GPI-linked protein. The 18E12-treated animals showed an increase at 36 hours which began to drop at 60 hours. When antibody-treated animals are challenged with LPS, there is no additional rise in CD14 levels in the 28C5 group, over what is noted in the antibody-only animal, suggesting that this is clearly and antibody-induced effect.

LBP Levels

Figure 22A:
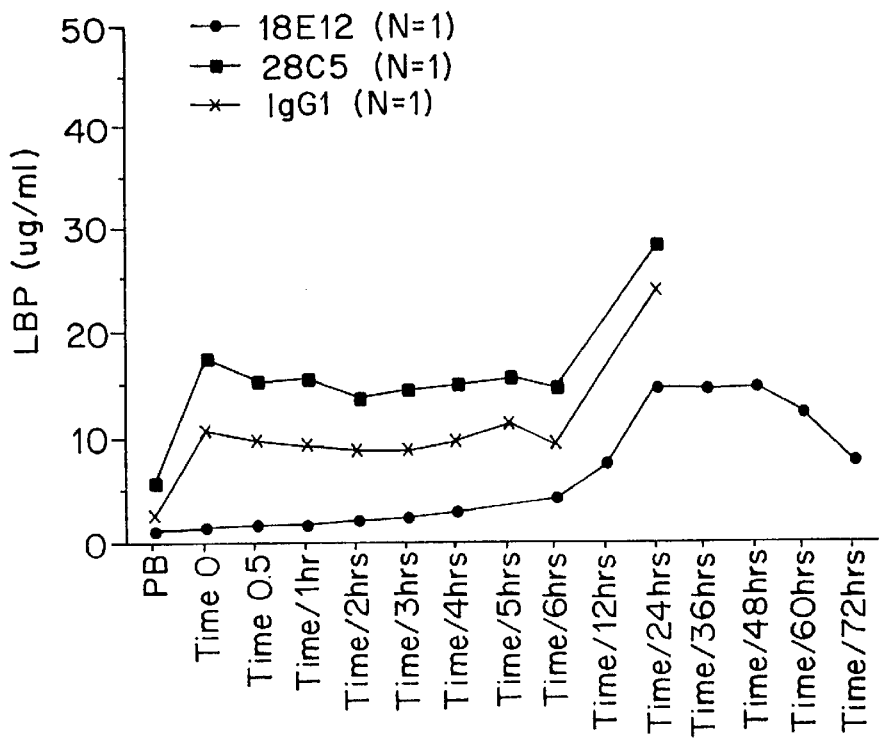
FIGS. 22A–B shows LBP levels in monkeys treated with antibody (18E12, 28C5 and IgG1) alone (top) or challenged with LPS after antibody treatment (bottom).
Figure 22B:
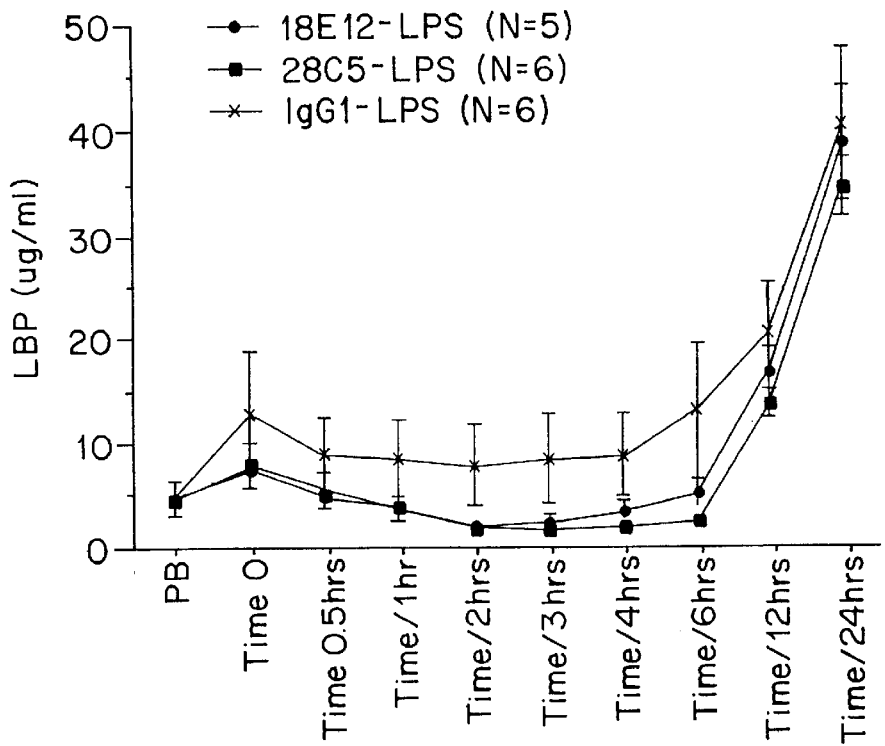

The LBP levels rise after interferon-gamma treatment, as was mentioned above. In the anti-CD14-treated, LPS challenged animals there is a slight lowering of detectable LBP levels versus control (FIG. 22). The reason for this is not known although it may represent clearance of the complexes if the targets are unavailable for binding or transfer of the LPS.

ALTGPT Levels

Enzyme transaminases ALT/GPT (considered the same enzyme) are indicators of liver function and as such were measured to determine if there was evidence of necrosis. In patients with septic shock, the onset of hepatic failure is an early event in the MSOF syndrome. Maximum levels In humans, depending upon the extent of damage, can reach 4000 U/ml. ALT/GPT levels were measured by following the manufacturer's recommendations in a test kit from Sigma Diagnostics.

Figure 23A:
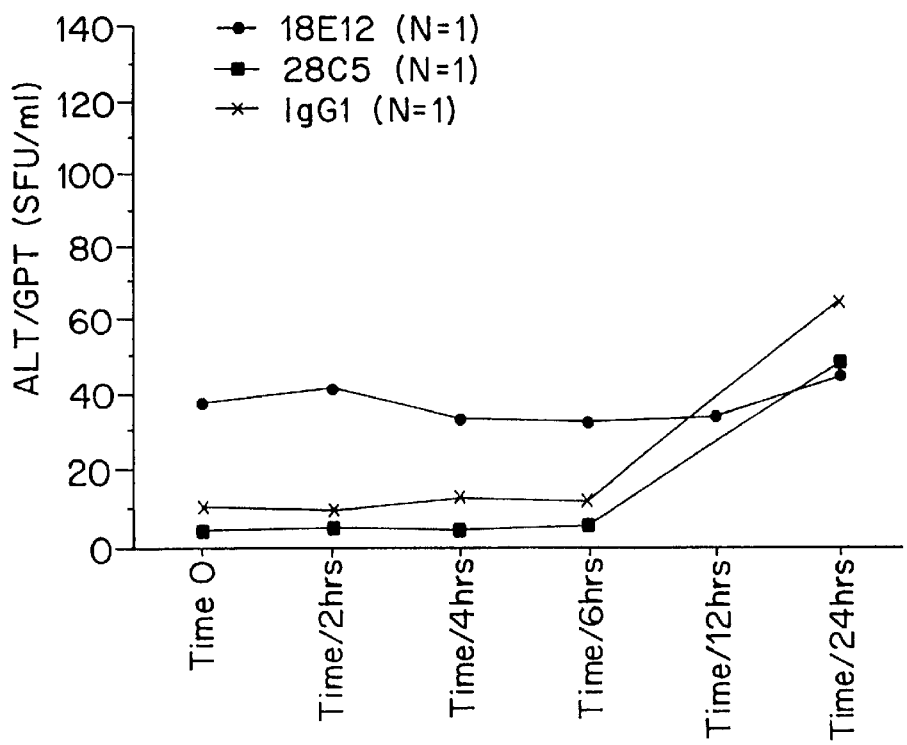
FIGS. 23A–B show ALT/GPT levels in monkeys treated with antibody (18E12, 28C5 and IgG1) alone (top) or challenged with LPS after antibody treatment (bottom).
Figure 23B:
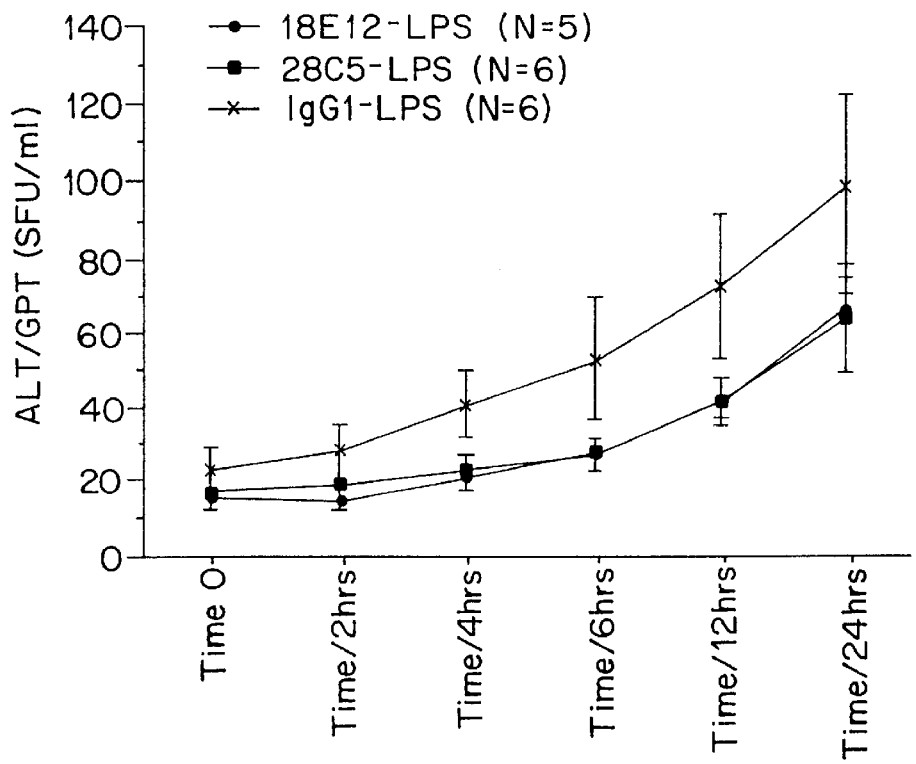

While none of the levels recorded here are in the range noted in an extreme human situation, there is a trend in the control group for elevated enzyme levels during the 24 hour time course of the experiment. Normal levels for ALT/GPT in monkeys treated with antibody only, ranged from a mean of 18 U/ml (T=0) to 52.2 U/ml (T=24), with the elevation at T=24 attributed to the anesthesia used throughout the study (ketamine). The two anti-CD14 treated groups followed a similar course; a mean of 16.5 U/ml at T=0 to 64.6 U/ml at T=24. The mean of the control group was 22.8 U/ml at T=0 to 98 U/ml at T=24. A twenty-four hour time course may not allow one to determine if the elevation in the control group of animals would continue (FIG. 23).

Soluble E-Selectin Levels

Figure 24A:
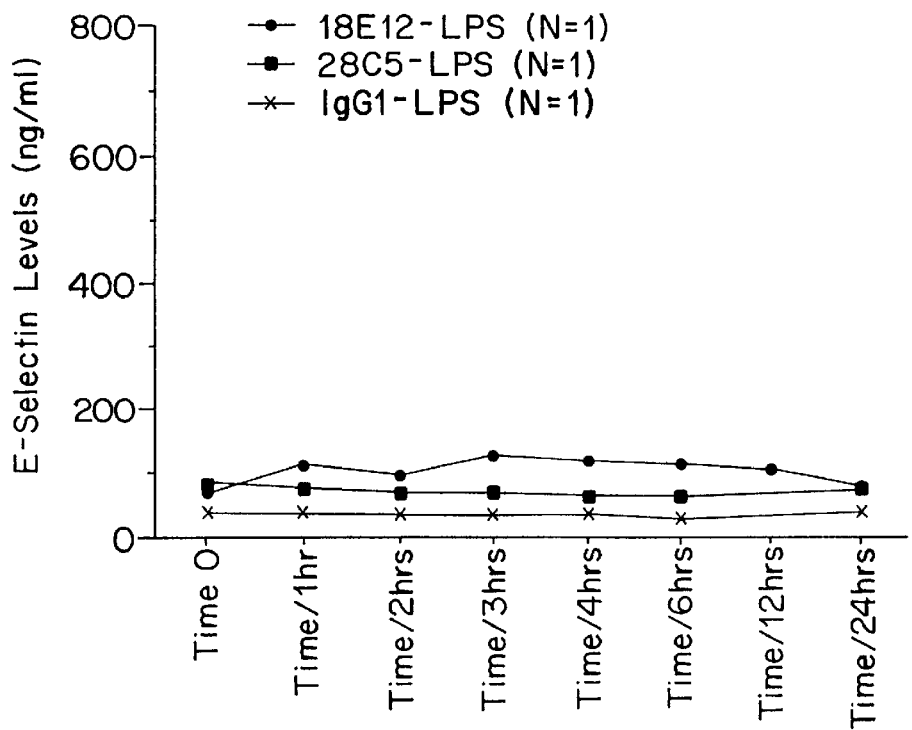
FIGS. 24A–B show E-selectin levels in monkeys treated with antibody (18E12, 28C5 and IgG1) alone (top) or challenged with LPS after antibody treatment (bottom).
Figure 24B:
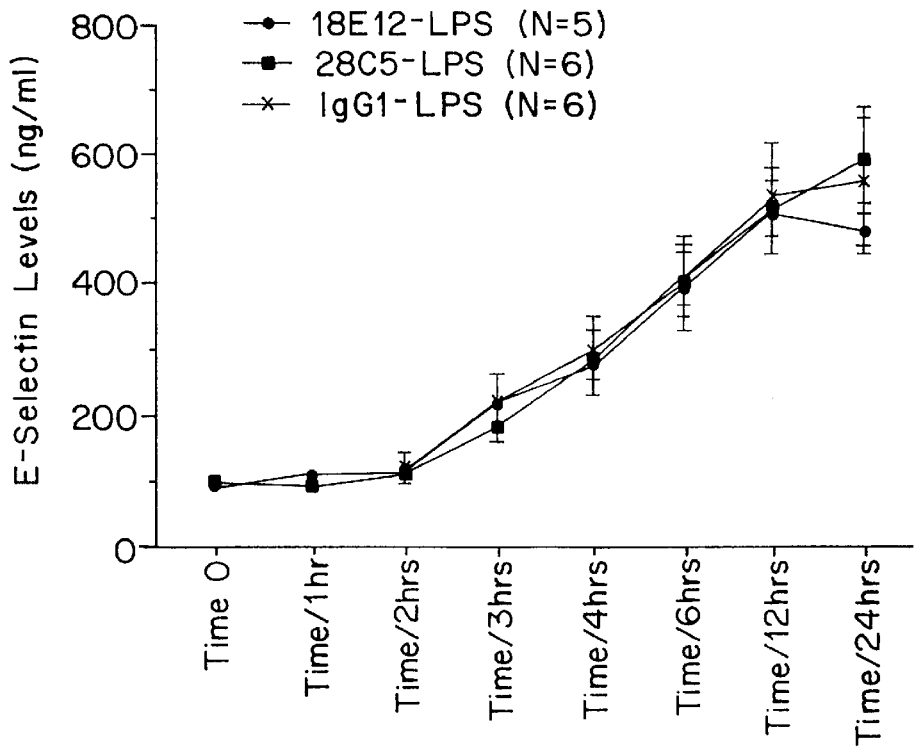

Soluble E-selectin levels were measured by Parameter ELISA kit (British Bio-technology Products, Ltd.) to determine if blocking the CD14 receptor would somehow prohibit release of soluble E-selectin from endothelial cells. E-selectin expression on the surface of endothelial cells is an indicator of activation of these cells and occurs as a consequence of TNF, IL-1 or LPS stimulation. Soluble E-selectin levels were elevated to similar levels, at 24 hours, in all groups (FIG. 24).

IL-1, IL-6, IL-8 and TNF Levels

Figure 25A:
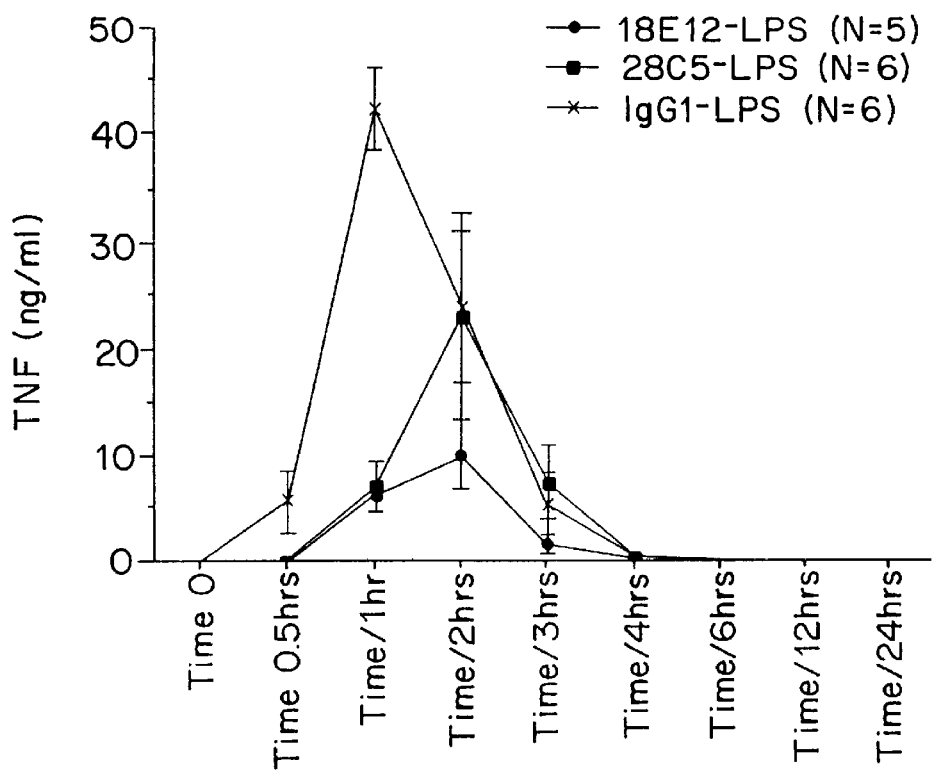
FIGS. 25A–B show TNF levels in monkeys treated with antibody (18E12, 28C5 and IgG1) and challenged with LPS (top) and IL-1 levels in monkeys treated with antibody (18E12, 28C5 and IgG1) and challenged with LPS after antibody treatment (bottom).
Figure 25B:
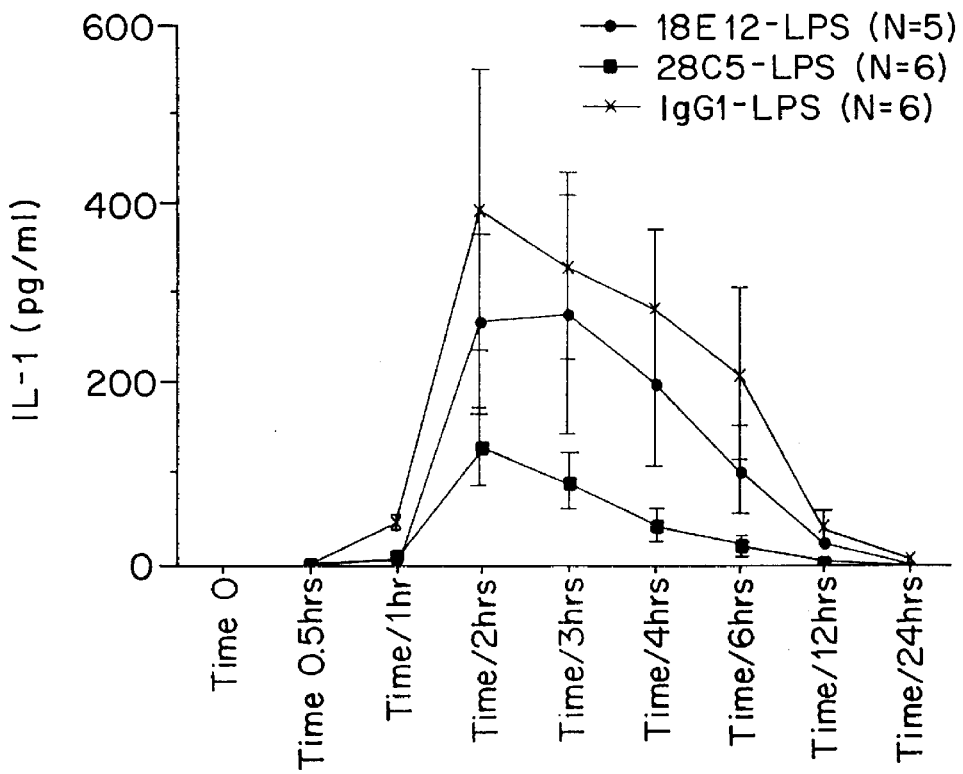

The cytokine response to LPS challenge was evaluated using Quantikine™ kits (R&D Systems), performed according to the manufacturer's specifications, in all groups of animals. The assay is an immunoassay with a solid phase ELISA format. The TNFα assay was a Biokine® enzyme immunoassay kit (T Cell Diagnostics) and was performed according to the manufacturer's specifications. It is known that TNFα and IL-1β are key mediators of the inflammatory response induced as a consequence of LPS stimulation. In the anti-CD14 treated groups, the TNFα and IL-1β responses were reduced versus the control treated group with 18E12 exhibiting the lowest level of expression of these inflammatory cytokines. Also, the peak TNF response was delayed by an hour in both anti-CD14 groups, the significance of this finding is not known at this time (FIG. 25).

Figure 26A:
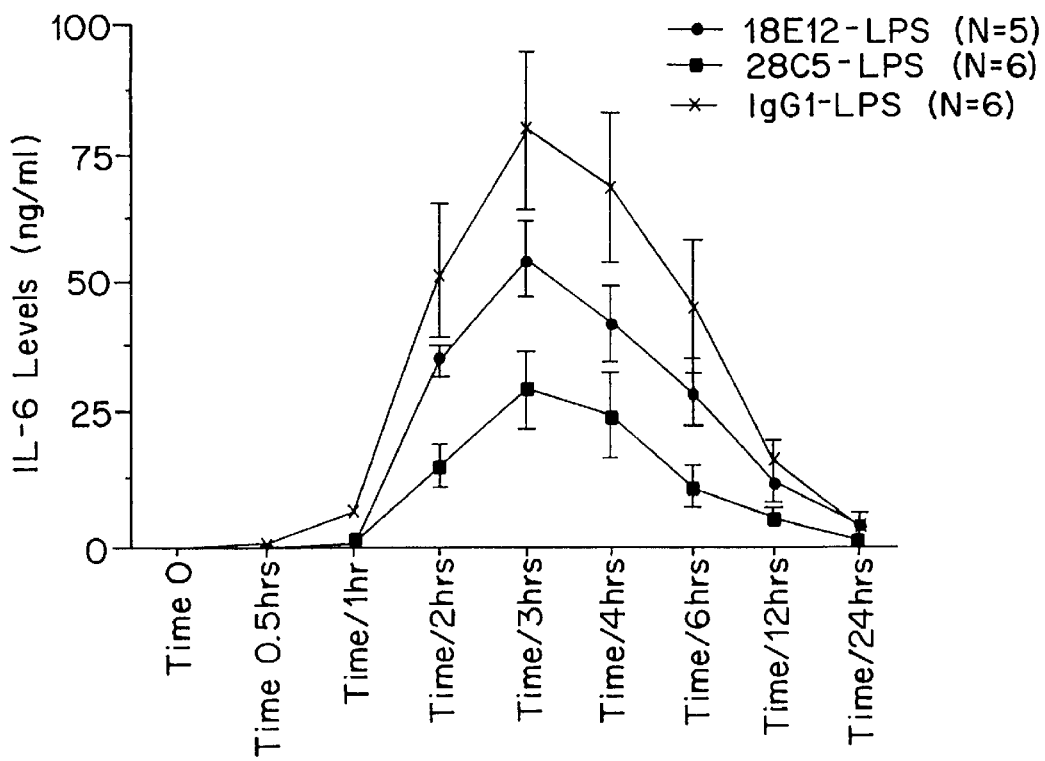
FIGS. 26A–B show IL-6 levels in monkeys treated with antibody (18E12, 28C5 and IgG1) and challenged with LPS (top) and IL-8 levels in monkeys treated with antibody (18E12, 28C5 and IgG1) and challenged with LPS after antibody treatment (bottom).
Figure 26B:
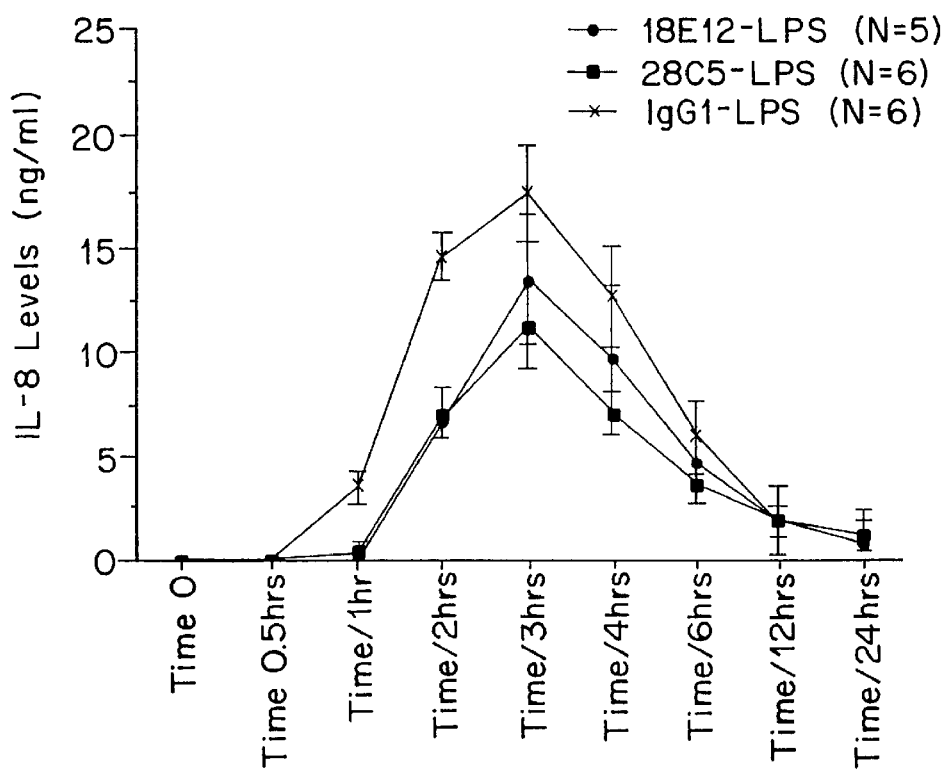

It is known that IL-1, IL-6 and IL-8 peak later than TNF in human septicemia, which is in line with the observations that release of IL-1, IL-6 and IL-8 is largely dependent on TNF generation. One cytokine which has been correlated with mortality in humans diagnosed with gram-negative sepsis is elevated IL-6 levels. IL-6 coordinates various aspects of the host defense against tissue injury. In the present model, 28C5 exhibited the lowest level of IL-6 in response to LPS. Animals pretreated with 18E12 also had lower levels than the control group, yet not as low as 28C5. The IL-8 response, while not significantly lower in the anti-CD14 groups, was reduced slightly (FIG. 26). IL-8 levels in baboon models were shown to be correlated with TNF levels; reduced TNF resulted in reduced IL-8 levels. IL-8 has chemoattractant and granulocyte activation properties. Relatively preserving the native IL-8 response, as noted in the anti-CD14 treated groups, may keep intact these important mediators of the host response to LPS.

SUMMARY OF SEQUENCES

SEQ ID NO: 1 is the nuleic acid and deduced amino acid sequence of the 28C5 heavy chain.

SEQ ID NO: 2 is the deduced amino acid sequence of the 28C5 heavy chain.

SEQ ID NO: 3 is the nucleic acid and deduced amino acid sequence of the 28C5 light chain.

SEQ ID NO: 4 is the deduced amino acid sequence of the 28C5 light chain.

SEQ ID NO: 5 is the nucleic acid and deduced amino acid sequence of the 18E12 heavy chain.

SEQ ID NO: 6 is the deduced amino acid sequence of the 18E12 heavy chain.

SEQ ID NO: 7 is the nucleic acid and deduced amino acid sequence of the 18E12 light chain.

SEQ ID NO: 8 is the deduced amino acid sequence of the 18E12 light chain.

SEQ ID NO: 9 shows the nucleic acid sequence which encodes the human soluble CD14 receptor.

SEQ ID NO: 10 is the amino acid sequence of CDR1 of 3C10 heavy chain.

SEQ ID NO: 11 is the amino acid sequence of CDR2 of 3C10 heavy chain.

SEQ ID NO: 12 is the amino acid sequence of CDR3 of 3C10 heavy chain.

SEQ ID NO: 13 is the amino acid sequence of CDR1 of 28C5 heavy chain.

SEQ ID NO: 14 is the amino acid sequence of CDR2 of 28C5 heavy chain.

SEQ ID NO: 15 is the amino acid sequence of CDR3 of 28C5 heavy chain.

SEQ ID NO: 16 is the amino acid sequence of CDR1 of 3C10 light chain.

SEQ ID NO: 17 is the amino acid sequence of CDR2 of 3C10 light chain.

SEQ ID NO: 18 is the amino acid sequence of CDR3 of 3C10 light chain.

SEQ ID NO: 19 is the amino acid sequence of CDR1 of 28C5 light chain.

SEQ ID NO: 20 is the amino acid sequence of CDR2 of 28C5 light chain.

SEQ ID NO: 21 is the amino acid sequence of CDR3 of 28C5 light chain.

SEQ ID NO: 22 is the amino acid sequence of CDR1 of 23G4 light chain.

SEQ ID NO: 23 is the amino acid sequence of CDR2 of 23G4 light chain.

SEQ ID NO: 24 is the amino acid sequence of CDR3 of 23G4 light chain.

SEQ ID NO: 25 is the amino acid sequence of the 23G4 light chain.

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
        ( A ) LENGTH: 639 base pairs
        ( B ) TYPE: nucleic acid
        ( C ) STRANDEDNESS: both
        ( D ) TOPOLOGY: linear ( i i ) MOLECULE TYPE: cDNA ( i x ) FEATURE:
        ( A ) NAME/KEY: CDS
        ( B ) LOCATION: 1..639
        ( D ) OTHER INFORMATION: /note= "CDR1=NUCLEIC ACIDS 94
            THROUGH 111;CDR2=NUCLEIC ACIDS 154 THROUGH
            201;CDR3=NUCLEIC ACIDS 298 THROUGH 315"

( x i ) SEQUENCE DESCRIPTION: SEQ ID NO:1:

```
CCC  CCC  CTC  GAG  CTT  CAG  CAG  TCA  GGA  CCT  GGC  CTG  GTG  AAA  CCT  TCT        48
Pro  Pro  Leu  Glu  Leu  Gln  Gln  Ser  Gly  Pro  Gly  Leu  Val  Lys  Pro  Ser
 1             5                        10                       15

CAG  TCT  CTG  TCC  CTC  ACC  TGC  ACT  GTC  ACT  GGC  TAC  TCA  ATC  ACC  AGT        96
Gln  Ser  Leu  Ser  Leu  Thr  Cys  Thr  Val  Thr  Gly  Tyr  Ser  Ile  Thr  Ser
              20                        25                       30

GAT  TCT  GCC  TGG  AAC  TGG  ATC  CGG  CAG  TTT  CCA  GGA  AAC  AGA  CTG  GAG       144
Asp  Ser  Ala  Trp  Asn  Trp  Ile  Arg  Gln  Phe  Pro  Gly  Asn  Arg  Leu  Glu
         35                        40                       45

TGG  ATG  GGC  TAC  ATA  AGC  TAC  AGT  GGT  AGC  ACT  AGC  TAC  AAC  CCA  TCT       192
Trp  Met  Gly  Tyr  Ile  Ser  Tyr  Ser  Gly  Ser  Thr  Ser  Tyr  Asn  Pro  Ser
     50                        55                       60

CTC  AAA  AGT  CGA  ATC  TCT  ATC  ACT  CGA  GAC  ACA  TCC  AAG  AAC  CAG  TTC       240
Leu  Lys  Ser  Arg  Ile  Ser  Ile  Thr  Arg  Asp  Thr  Ser  Lys  Asn  Gln  Phe
 65                        70                       75                       80

TTC  CTG  CAG  TTG  AAT  TCG  GTG  ACT  ACT  GAG  GAC  ACA  GCC  ACA  TAT  TAC       288
Phe  Leu  Gln  Leu  Asn  Ser  Val  Thr  Thr  Glu  Asp  Thr  Ala  Thr  Tyr  Tyr
                    85                       90                       95

TGT  GTA  AGA  GGG  CTC  CGG  TTT  GCT  TAC  TGG  GGG  AAG  GGG  ACT  CTG  GTC       336
Cys  Val  Arg  Gly  Leu  Arg  Phe  Ala  Tyr  Trp  Gly  Lys  Gly  Thr  Leu  Val
              100                       105                      110

ACT  GTC  TCT  GCA  GCA  AAA  ACA  ACC  CCC  CCT  TCT  GTC  TAT  CCA  CTG  CCC       384
Thr  Val  Ser  Ala  Ala  Lys  Thr  Thr  Pro  Pro  Ser  Val  Tyr  Pro  Leu  Pro
              115                       120                      125

CCT  GGA  TCT  GCT  GCC  CAA  ACT  AAC  TCC  ATG  GTG  ACC  CTG  GGA  TGC  CTG       432
Pro  Gly  Ser  Ala  Ala  Gln  Thr  Asn  Ser  Met  Val  Thr  Leu  Gly  Cys  Leu
     130                       135                      140

GTC  AAG  GCC  TAT  TTC  CCT  GAG  CCA  GTG  ACA  GTG  ACC  TGG  AAC  TCT  GGA       480
Val  Lys  Ala  Tyr  Phe  Pro  Glu  Pro  Val  Thr  Val  Thr  Trp  Asn  Ser  Gly
 145                       150                      155                      160

TCC  CTG  TCC  AGC  GGT  TGG  CAC  ACC  TTC  CCA  GCT  GTC  CTG  CAG  TCT  GAC       528
Ser  Leu  Ser  Ser  Gly  Trp  His  Thr  Phe  Pro  Ala  Val  Leu  Gln  Ser  Asp
                    165                      170                      175

CTC  TAC  ACT  CTG  AGC  AGC  TCA  GTG  ACT  GTC  CCC  TCC  AGC  ACC  TGG  CCC       576
Leu  Tyr  Thr  Leu  Ser  Ser  Ser  Val  Thr  Val  Pro  Ser  Ser  Thr  Trp  Pro
               180                       185                      190

AGC  GAG  ACC  GTC  ACC  TGC  AAC  GTT  GCC  CAC  CCG  GCC  AGC  AGC  ACC  AAG       624
Ser  Glu  Thr  Val  Thr  Cys  Asn  Val  Ala  His  Pro  Ala  Ser  Ser  Thr  Lys
               195                       200                      205

GTG  GAC  AAG  AAA  ATT                                                              639
```

Val Asp Lys Lys Ile
210

( 2 ) INFORMATION FOR SEQ ID NO:2:

( i ) SEQUENCE CHARACTERISTICS:
        ( A ) LENGTH: 213 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Pro Pro Leu Glu Leu Gln Gln Ser Gly Pro Gly Leu Val Lys Pro Ser
 1           5                  10                  15

Gln Ser Leu Ser Leu Thr Cys Thr Val Thr Gly Tyr Ser Ile Thr Ser
            20                  25                  30

Asp Ser Ala Trp Asn Trp Ile Arg Gln Phe Pro Gly Asn Arg Leu Glu
            35                  40                  45

Trp Met Gly Tyr Ile Ser Tyr Ser Gly Ser Thr Ser Tyr Asn Pro Ser
        50                  55                  60

Leu Lys Ser Arg Ile Ser Ile Thr Arg Asp Thr Ser Lys Asn Gln Phe
65                   70                  75                  80

Phe Leu Gln Leu Asn Ser Val Thr Thr Glu Asp Thr Ala Thr Tyr Tyr
                85                  90                  95

Cys Val Arg Gly Leu Arg Phe Ala Tyr Trp Gly Lys Gly Thr Leu Val
            100                 105                 110

Thr Val Ser Ala Ala Lys Thr Thr Pro Pro Ser Val Tyr Pro Leu Pro
            115                 120                 125

Pro Gly Ser Ala Ala Gln Thr Asn Ser Met Val Thr Leu Gly Cys Leu
        130                 135                 140

Val Lys Ala Tyr Phe Pro Glu Pro Val Thr Val Thr Trp Asn Ser Gly
145                 150                 155                 160

Ser Leu Ser Ser Gly Trp His Thr Phe Pro Ala Val Leu Gln Ser Asp
                165                 170                 175

Leu Tyr Thr Leu Ser Ser Ser Val Thr Val Pro Ser Ser Thr Trp Pro
            180                 185                 190

Ser Glu Thr Val Thr Cys Asn Val Ala His Pro Ala Ser Ser Thr Lys
            195                 200                 205

Val Asp Lys Lys Ile
    210
```

( 2 ) INFORMATION FOR SEQ ID NO:3:

( i ) SEQUENCE CHARACTERISTICS:
        ( A ) LENGTH: 645 base pairs
        ( B ) TYPE: nucleic acid
        ( C ) STRANDEDNESS: both
        ( D ) TOPOLOGY: linear ( i i ) MOLECULE TYPE: cDNA ( i x ) FEATURE:
        ( A ) NAME/KEY: CDS
        ( B ) LOCATION: 1..645
        ( D ) OTHER INFORMATION: /note= "CDR1=NUCLEIC ACIDS 61
            THROUGH 105;CDR2=NUCLEIC ACIDS 151 THROUGH
            171;CDR3=NUCLEIC ACIDS 268 THROUGH 294"

( x i ) SEQUENCE DESCRIPTION: SEQ ID NO:3:

```
ATG ACA CAG TCT CCA GCT TCT TTG GCT GTG TCT CTA GGG CAG AGG GCC      48
Met Thr Gln Ser Pro Ala Ser Leu Ala Val Ser Leu Gly Gln Arg Ala
 1           5                  10                  15
```

| | | | | | | | | | | | | | | | | |
|---|---|---|---|---|---|---|---|---|---|---|---|---|---|---|---|---|
| CCA | TAT | CCT | TGC | AGA | GCC | AGT | GAA | AGT | GTT | GAT | AGT | TAT | GTC | AAT | AGT | 96 |
| Pro | Tyr | Pro | Cys | Arg | Ala | Ser | Glu | Ser | Val | Asp | Ser | Tyr | Val | Asn | Ser | |
| | | | 20 | | | | | 25 | | | | | 30 | | | |
| TTT | CTC | CAC | TGG | TAC | CAG | CAG | AAA | CCA | GGA | CAG | CCA | CCC | AAA | CTC | CTC | 144 |
| Phe | Leu | His | Trp | Tyr | Gln | Gln | Lys | Pro | Gly | Gln | Pro | Pro | Lys | Leu | Leu | |
| | | 35 | | | | | 40 | | | | | 45 | | | | |
| ATC | TAT | CGT | GCA | TCC | AAC | CTA | CAA | TCT | GGG | ATC | CCT | GCC | AGG | TTC | AGT | 192 |
| Ile | Tyr | Arg | Ala | Ser | Asn | Leu | Gln | Ser | Gly | Ile | Pro | Ala | Arg | Phe | Ser | |
| | 50 | | | | | 55 | | | | | 60 | | | | | |
| GGC | AGT | GGG | TCT | AGG | ACA | GAC | TTC | ACC | CTC | ACC | ATT | AAT | CCT | GTG | GAG | 240 |
| Gly | Ser | Gly | Ser | Arg | Thr | Asp | Phe | Thr | Leu | Thr | Ile | Asn | Pro | Val | Glu | |
| 65 | | | | 70 | | | | | 75 | | | | | | 80 | |
| GCT | GAT | GAT | GTT | GCA | ACC | TAT | TAC | TGT | CAG | CAA | AGT | AAT | GAG | GAT | CCG | 288 |
| Ala | Asp | Asp | Val | Ala | Thr | Tyr | Tyr | Cys | Gln | Gln | Ser | Asn | Glu | Asp | Pro | |
| | | | | 85 | | | | | 90 | | | | | 95 | | |
| ACG | ACG | TCG | GGA | GGG | GGC | ACC | AAG | CTG | GAA | ATA | AAA | CGG | GCT | GAT | GCT | 336 |
| Thr | Thr | Ser | Gly | Gly | Gly | Thr | Lys | Leu | Glu | Ile | Lys | Arg | Ala | Asp | Ala | |
| | | | 100 | | | | | 105 | | | | | 110 | | | |
| GCA | CCC | CTT | GTA | TCC | ATC | TTC | CCC | CCA | TCC | AGT | GAG | CAG | TTA | ACA | TCT | 384 |
| Ala | Pro | Leu | Val | Ser | Ile | Phe | Pro | Pro | Ser | Ser | Glu | Gln | Leu | Thr | Ser | |
| | | 115 | | | | | 120 | | | | | 125 | | | | |
| GGA | GGT | GCC | TCA | GTT | GTG | TGC | TTC | TTG | AAC | AAC | TTC | TAC | CCC | AAA | GAC | 432 |
| Gly | Gly | Ala | Ser | Val | Val | Cys | Phe | Leu | Asn | Asn | Phe | Tyr | Pro | Lys | Asp | |
| | 130 | | | | | 135 | | | | | 140 | | | | | |
| ATC | AAT | GTC | AAG | TGG | AAG | ATT | GAT | GTC | AGT | GAA | CGA | CAA | AAT | GGC | GTC | 480 |
| Ile | Asn | Val | Lys | Trp | Lys | Ile | Asp | Val | Ser | Glu | Arg | Gln | Asn | Gly | Val | |
| 145 | | | | | 150 | | | | | 155 | | | | | 160 | |
| CTG | AAC | AGT | TGG | ACT | GAT | CAG | GAC | AGC | AAA | GAC | AGC | ACC | TAC | AGC | ATG | 528 |
| Leu | Asn | Ser | Trp | Thr | Asp | Gln | Asp | Ser | Lys | Asp | Ser | Thr | Tyr | Ser | Met | |
| | | | | 165 | | | | | 170 | | | | | 175 | | |
| AGC | AGC | ACC | CTC | ACG | TTG | ACC | AAG | GAC | GAG | TAT | GAA | CGA | CAT | AAC | AGC | 576 |
| Ser | Ser | Thr | Leu | Thr | Leu | Thr | Lys | Asp | Glu | Tyr | Glu | Arg | His | Asn | Ser | |
| | | | 180 | | | | | 185 | | | | | 190 | | | |
| TAT | ACC | TGT | GAG | GCC | ACT | CAC | AAG | ACA | TCA | ACT | TCA | CCC | ATT | GTC | AAG | 624 |
| Tyr | Thr | Cys | Glu | Ala | Thr | His | Lys | Thr | Ser | Thr | Ser | Pro | Ile | Val | Lys | |
| | | 195 | | | | | 200 | | | | | 205 | | | | |
| AGC | TTC | AAC | AGG | AAT | GAG | TGT | | | | | | | | | | 645 |
| Ser | Phe | Asn | Arg | Asn | Glu | Cys | | | | | | | | | | |
| 210 | | | | | 215 | | | | | | | | | | | |

( 2 ) INFORMATION FOR SEQ ID NO:4:

( i ) SEQUENCE CHARACTERISTICS:
        ( A ) LENGTH: 215 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | | |
|---|---|---|---|---|---|---|---|---|---|---|---|---|---|---|---|
| Met | Thr | Gln | Ser | Pro | Ala | Ser | Leu | Ala | Val | Ser | Leu | Gly | Gln | Arg | Ala |
| 1 | | | | 5 | | | | | 10 | | | | | 15 | |
| Pro | Tyr | Pro | Cys | Arg | Ala | Ser | Glu | Ser | Val | Asp | Ser | Tyr | Val | Asn | Ser |
| | | | 20 | | | | | 25 | | | | | 30 | | |
| Phe | Leu | His | Trp | Tyr | Gln | Gln | Lys | Pro | Gly | Gln | Pro | Pro | Lys | Leu | Leu |
| | | 35 | | | | | 40 | | | | | 45 | | | |
| Ile | Tyr | Arg | Ala | Ser | Asn | Leu | Gln | Ser | Gly | Ile | Pro | Ala | Arg | Phe | Ser |
| | 50 | | | | | 55 | | | | | 60 | | | | |
| Gly | Ser | Gly | Ser | Arg | Thr | Asp | Phe | Thr | Leu | Thr | Ile | Asn | Pro | Val | Glu |
| 65 | | | | 70 | | | | | 75 | | | | | | 80 |

| | | | | | | | | | | | | | | |
|---|---|---|---|---|---|---|---|---|---|---|---|---|---|---|
| Ala | Asp | Asp | Val | Ala<br>85 | Thr | Tyr | Tyr | Cys | Gln<br>90 | Gln | Ser | Asn | Glu<br>95 | Pro |
| Thr | Thr | Ser | Gly<br>100 | Gly | Gly | Thr | Lys | Leu<br>105 | Glu | Ile | Lys | Arg<br>110 | Ala | Asp | Ala |
| Ala | Pro | Leu<br>115 | Val | Ser | Ile | Phe | Pro<br>120 | Pro | Ser | Ser | Glu<br>125 | Gln | Leu | Thr | Ser |
| Gly | Gly<br>130 | Ala | Ser | Val | Val | Cys<br>135 | Phe | Leu | Asn | Asn | Phe<br>140 | Tyr | Pro | Lys | Asp |
| Ile<br>145 | Asn | Val | Lys | Trp | Lys<br>150 | Ile | Asp | Val | Ser | Glu<br>155 | Arg | Gln | Asn | Gly | Val<br>160 |
| Leu | Asn | Ser | Trp | Thr<br>165 | Asp | Gln | Asp | Ser | Lys<br>170 | Asp | Ser | Thr | Tyr | Ser<br>175 | Met |
| Ser | Ser | Thr | Leu<br>180 | Thr | Leu | Thr | Lys | Asp<br>185 | Glu | Tyr | Glu | Arg | His<br>190 | Asn | Ser |
| Tyr | Thr | Cys<br>195 | Glu | Ala | Thr | His | Lys<br>200 | Thr | Ser | Thr | Ser | Pro<br>205 | Ile | Val | Lys |
| Ser | Phe<br>210 | Asn | Arg | Asn | Glu | Cys<br>215 | | | | | | | | | |

( 2 ) INFORMATION FOR SEQ ID NO:5:

( i ) SEQUENCE CHARACTERISTICS:
        ( A ) LENGTH: 645 base pairs
        ( B ) TYPE: nucleic acid
        ( C ) STRANDEDNESS: both
        ( D ) TOPOLOGY: linear ( i i ) MOLECULE TYPE: cDNA ( i x ) FEATURE:
        ( A ) NAME/KEY: CDS
        ( B ) LOCATION: 1..645
        ( D ) OTHER INFORMATION: /note= "CDR1=NUCLEIC ACIDS 85
            THROUGH 99; CDR2=NUCLEIC ACIDS 142 THROUGH 189;
            CDR3=NUCLEIC ACIDS 286-321"

( x i ) SEQUENCE DESCRIPTION: SEQ ID NO:5:

| | | | | | | | | | | | | | | | |
|---|---|---|---|---|---|---|---|---|---|---|---|---|---|---|---|
| CCC<br>Pro<br>1 | CCC<br>Pro | CTC<br>Leu | GAG<br>Glu | TCA<br>Ser<br>5 | GGA<br>Gly | CCT<br>Pro | GGC<br>Gly | CTG<br>Leu | GTG<br>Val<br>10 | GCG<br>Ala | CCC<br>Pro | TCA<br>Ser | CAG<br>Gln | AGC<br>Ser<br>15 | CTG<br>Leu | 48 |
| TCC<br>Ser | ATT<br>Ile | ACC<br>Thr | TGC<br>Cys<br>20 | ACT<br>Thr | GTC<br>Val | TCT<br>Ser | GGG<br>Gly | TTC<br>Phe<br>25 | TCA<br>Ser | TTA<br>Leu | ACC<br>Thr | AAC<br>Asn | TAT<br>Tyr<br>30 | GAT<br>Asp | ATA<br>Ile | 96 |
| AGC<br>Ser | TGG<br>Trp | ATT<br>Ile<br>35 | CGC<br>Arg | CAG<br>Gln | CCA<br>Pro | CCA<br>Pro | GGA<br>Gly<br>40 | AAA<br>Lys | GGT<br>Gly | CTG<br>Leu | GAG<br>Glu | TGG<br>Trp<br>45 | CTT<br>Leu | GGA<br>Gly | GTA<br>Val | 144 |
| ATA<br>Ile | TGG<br>Trp<br>50 | ACT<br>Thr | AGT<br>Ser | GGA<br>Gly | GGC<br>Gly | ACA<br>Thr<br>55 | AAT<br>Asn | TAT<br>Tyr | AAT<br>Asn | TCA<br>Ser | GCT<br>Ala<br>60 | TTC<br>Phe | ATG<br>Met | TCC<br>Ser | CGA<br>Arg | 192 |
| CTG<br>Leu<br>65 | AGC<br>Ser | ATC<br>Ile | ACC<br>Thr | AAG<br>Lys | GAC<br>Asp<br>70 | AAC<br>Asn | TCC<br>Ser | AAG<br>Lys | AGC<br>Ser | CAA<br>Gln<br>75 | GTT<br>Val | TTC<br>Phe | TTA<br>Leu | AAA<br>Lys | ATG<br>Met<br>80 | 240 |
| AAC<br>Asn | GGT<br>Gly | CTG<br>Leu | CAA<br>Gln | ACT<br>Thr<br>85 | GAT<br>Asp | GAC<br>Asp | ACA<br>Thr | GGC<br>Gly | ATA<br>Ile<br>90 | TCT<br>Ser | TAC<br>Tyr | TGT<br>Cys | GTA<br>Val | AGA<br>Arg<br>95 | GGT<br>Gly | 288 |
| GAT<br>Asp | GGT<br>Gly | AAC<br>Asn | TTC<br>Phe<br>100 | TAC<br>Tyr | TTG<br>Leu | TAC<br>Tyr | AAC<br>Asn | TTT<br>Phe<br>105 | GAC<br>Asp | TAT<br>Tyr | TGG<br>Trp | GGC<br>Gly | CAA<br>Gln<br>110 | GGC<br>Gly | ACC<br>Thr | 336 |
| ACT<br>Thr | CTC<br>Leu | ACA<br>Thr<br>115 | GTC<br>Val | TCC<br>Ser | TCA<br>Ser | GCC<br>Ala | AAA<br>Lys<br>120 | ACG<br>Thr | ACA<br>Thr | CCC<br>Pro | CCA<br>Pro | TCT<br>Ser<br>125 | GTC<br>Val | TAT<br>Tyr | CCA<br>Pro | 384 |
| CTG<br>Leu | GCC<br>Ala | CCT<br>Pro | GGA<br>Gly | TCT<br>Ser | GCT<br>Ala | GCC<br>Ala | CAA<br>Gln | ACT<br>Thr | AAC<br>Asn | TCC<br>Ser | ATG<br>Met | GTG<br>Val | ACC<br>Thr | CTG<br>Leu | GGA<br>Gly | 432 |

|     |     |     |     |     |     |     |     |     |     |     |     |     |     |     |     |
| --- | --- | --- | --- | --- | --- | --- | --- | --- | --- | --- | --- | --- | --- | --- | --- |
| Leu | Ala | Pro | Gly | Ser | Ala | Ala | Gln | Thr | Asn | Ser | Met | Val | Thr | Leu | Gly |
|     | 130 |     |     |     |     | 135 |     |     |     |     | 140 |     |     |     |     |
| TGC | CTG | GTC | AAG | GGC | TAT | TTC | CCT | GAG | CCA | GTG | ACA | GTG | ACC | TGG | AAC | 480 |
| Cys | Leu | Val | Lys | Gly | Tyr | Phe | Pro | Glu | Pro | Val | Thr | Val | Thr | Trp | Asn |
| 145 |     |     |     |     | 150 |     |     |     |     | 155 |     |     |     |     | 160 |
| TCT | GGA | TCC | CTG | TCC | AGC | GGT | GTG | CAC | ACC | TTC | CCA | GCT | GTC | CTG | CAG | 528 |
| Ser | Gly | Ser | Leu | Ser | Ser | Gly | Val | His | Thr | Phe | Pro | Ala | Val | Leu | Gln |
|     |     |     |     | 165 |     |     |     |     | 170 |     |     |     |     | 175 |     |
| TCT | GAC | CTC | TAC | ACT | CTG | AGC | AGC | TCA | GTG | ACT | GTC | CCC | TCC | AGC | ACC | 576 |
| Ser | Asp | Leu | Tyr | Thr | Leu | Ser | Ser | Ser | Val | Thr | Val | Pro | Ser | Ser | Thr |
|     |     |     | 180 |     |     |     |     | 185 |     |     |     |     | 190 |     |     |
| TGG | CCC | AGC | GAG | ACC | GTC | ACC | TGC | AAC | GTT | GCC | CAC | CCG | GCC | AGC | AGC | 624 |
| Trp | Pro | Ser | Glu | Thr | Val | Thr | Cys | Asn | Val | Ala | His | Pro | Ala | Ser | Ser |
|     |     | 195 |     |     |     |     | 200 |     |     |     |     | 205 |     |     |     |
| ACC | AAG | GTG | GAC | AAG | AAA | ATT |     |     |     |     |     |     |     |     |     | 645 |
| Thr | Lys | Val | Asp | Lys | Lys | Ile |     |     |     |     |     |     |     |     |     |
|     | 210 |     |     |     |     | 215 |     |     |     |     |     |     |     |     |     |

( 2 ) INFORMATION FOR SEQ ID NO:6:

( i ) SEQUENCE CHARACTERISTICS:
        ( A ) LENGTH: 215 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

|     |     |     |     |     |     |     |     |     |     |     |     |     |     |     |     |
| --- | --- | --- | --- | --- | --- | --- | --- | --- | --- | --- | --- | --- | --- | --- | --- |
| Pro | Pro | Leu | Glu | Ser | Gly | Pro | Gly | Leu | Val | Ala | Pro | Ser | Gln | Ser | Leu |
| 1   |     |     |     | 5   |     |     |     |     | 10  |     |     |     |     | 15  |     |
| Ser | Ile | Thr | Cys | Thr | Val | Ser | Gly | Phe | Ser | Leu | Thr | Asn | Tyr | Asp | Ile |
|     |     |     | 20  |     |     |     |     | 25  |     |     |     |     | 30  |     |     |
| Ser | Trp | Ile | Arg | Gln | Pro | Pro | Gly | Lys | Gly | Leu | Glu | Trp | Leu | Gly | Val |
|     |     |     | 35  |     |     |     |     | 40  |     |     |     |     | 45  |     |     |
| Ile | Trp | Thr | Ser | Gly | Gly | Thr | Asn | Tyr | Asn | Ser | Ala | Phe | Met | Ser | Arg |
|     |     | 50  |     |     |     |     | 55  |     |     |     |     | 60  |     |     |     |
| Leu | Ser | Ile | Thr | Lys | Asp | Asn | Ser | Lys | Ser | Gln | Val | Phe | Leu | Lys | Met |
| 65  |     |     |     |     | 70  |     |     |     |     | 75  |     |     |     |     | 80  |
| Asn | Gly | Leu | Gln | Thr | Asp | Asp | Thr | Gly | Ile | Ser | Tyr | Cys | Val | Arg | Gly |
|     |     |     |     | 85  |     |     |     |     | 90  |     |     |     |     | 95  |     |
| Asp | Gly | Asn | Phe | Tyr | Leu | Tyr | Asn | Phe | Asp | Tyr | Trp | Gly | Gln | Gly | Thr |
|     |     |     | 100 |     |     |     |     | 105 |     |     |     |     | 110 |     |     |
| Thr | Leu | Thr | Val | Ser | Ser | Ala | Lys | Thr | Thr | Pro | Pro | Ser | Val | Tyr | Pro |
|     |     | 115 |     |     |     |     | 120 |     |     |     |     | 125 |     |     |     |
| Leu | Ala | Pro | Gly | Ser | Ala | Ala | Gln | Thr | Asn | Ser | Met | Val | Thr | Leu | Gly |
|     | 130 |     |     |     |     | 135 |     |     |     |     | 140 |     |     |     |     |
| Cys | Leu | Val | Lys | Gly | Tyr | Phe | Pro | Glu | Pro | Val | Thr | Val | Thr | Trp | Asn |
| 145 |     |     |     |     | 150 |     |     |     |     | 155 |     |     |     |     | 160 |
| Ser | Gly | Ser | Leu | Ser | Ser | Gly | Val | His | Thr | Phe | Pro | Ala | Val | Leu | Gln |
|     |     |     |     | 165 |     |     |     |     | 170 |     |     |     |     | 175 |     |
| Ser | Asp | Leu | Tyr | Thr | Leu | Ser | Ser | Ser | Val | Thr | Val | Pro | Ser | Ser | Thr |
|     |     |     | 180 |     |     |     |     | 185 |     |     |     |     | 190 |     |     |
| Trp | Pro | Ser | Glu | Thr | Val | Thr | Cys | Asn | Val | Ala | His | Pro | Ala | Ser | Ser |
|     |     | 195 |     |     |     |     | 200 |     |     |     |     | 205 |     |     |     |
| Thr | Lys | Val | Asp | Lys | Lys | Ile |     |     |     |     |     |     |     |     |     |
|     | 210 |     |     |     |     | 215 |     |     |     |     |     |     |     |     |     |

( 2 ) INFORMATION FOR SEQ ID NO:7:

( i ) SEQUENCE CHARACTERISTICS:
    ( A ) LENGTH: 633 base pairs
    ( B ) TYPE: nucleic acid
    ( C ) STRANDEDNESS: both
    ( D ) TOPOLOGY: linear ( i i ) MOLECULE TYPE: cDNA ( i x ) FEATURE:
    ( A ) NAME/KEY: CDS
    ( B ) LOCATION: 1..633
    ( D ) OTHER INFORMATION: /note= "CDR1=NUCLEIC ACIDS 61 THROUGH 93;CDR2=NUCLEIC ACIDS 139 THROUGH 159;CDR3=NUCLEIC ACIDS 256 THROUGH 282"

( x i ) SEQUENCE DESCRIPTION: SEQ ID NO:7:

| ATG | ACC | CAG | ACT | CCA | TCC | TCC | CTG | TCT | GCC | TCT | CTG | GGA | GAC | AGA | GTC | 48 |
| Met | Thr | Gln | Thr | Pro | Ser | Ser | Leu | Ser | Ala | Ser | Leu | Gly | Asp | Arg | Val | |
| 1 | | | | 5 | | | | | 10 | | | | | 15 | | |

| ACC | ATC | AGT | TGC | AGG | GCA | AGT | CAG | GAC | ATT | AAG | AAT | TAT | TTA | AAC | TGG | 96 |
| Thr | Ile | Ser | Cys | Arg | Ala | Ser | Gln | Asp | Ile | Lys | Asn | Tyr | Leu | Asn | Trp | |
| | | | 20 | | | | | 25 | | | | | 30 | | | |

| TAT | CAG | CAG | GGA | CCA | GGT | GGA | ACT | GTT | AAA | GTC | CTA | ATC | TAC | TAC | ACA | 144 |
| Tyr | Gln | Gln | Gly | Pro | Gly | Gly | Thr | Val | Lys | Val | Leu | Ile | Tyr | Tyr | Thr | |
| | | 35 | | | | | 40 | | | | | 45 | | | | |

| TCA | AGA | TTA | CAC | TCA | GGA | GTC | CCA | TCA | AGG | TTC | AGT | GGC | AGT | GGG | TCT | 192 |
| Ser | Arg | Leu | His | Ser | Gly | Val | Pro | Ser | Arg | Phe | Ser | Gly | Ser | Gly | Ser | |
| | 50 | | | | | 55 | | | | | 60 | | | | | |

| GGA | ACA | GAT | TAT | TCT | CTC | ACC | ATT | AGC | AAC | CTG | GAG | CAA | GAA | GAT | TTT | 240 |
| Gly | Thr | Asp | Tyr | Ser | Leu | Thr | Ile | Ser | Asn | Leu | Glu | Gln | Glu | Asp | Phe | |
| 65 | | | | | 70 | | | | | 75 | | | | | 80 | |

| GCC | ACT | TAC | TTT | TGC | CAA | CGG | GGT | GAT | ACG | CTT | CCG | TGG | ACG | TTC | GGT | 288 |
| Ala | Thr | Tyr | Phe | Cys | Gln | Arg | Gly | Asp | Thr | Leu | Pro | Trp | Thr | Phe | Gly | |
| | | | | 85 | | | | | 90 | | | | | 95 | | |

| GGA | GGC | ACC | AAG | CTG | GAA | ATC | AAA | ACG | GCT | GAT | GCT | GCA | CCA | ACT | GTA | 336 |
| Gly | Gly | Thr | Lys | Leu | Glu | Ile | Lys | Thr | Ala | Asp | Ala | Ala | Pro | Thr | Val | |
| | | | 100 | | | | | 105 | | | | | 110 | | | |

| TCC | ATC | TTC | CCC | CCA | TCC | AGT | GAG | CAG | TTA | ACA | TCT | GGG | GGT | GCC | TCA | 384 |
| Ser | Ile | Phe | Pro | Pro | Ser | Ser | Glu | Gln | Leu | Thr | Ser | Gly | Gly | Ala | Ser | |
| | | 115 | | | | | 120 | | | | | 125 | | | | |

| GTC | GTG | TGC | TTC | TTG | AAC | AAC | TTC | TAC | CCC | AAA | GAC | ATC | AAT | GTC | AAG | 432 |
| Val | Val | Cys | Phe | Leu | Asn | Asn | Phe | Tyr | Pro | Lys | Asp | Ile | Asn | Val | Lys | |
| | 130 | | | | | 135 | | | | | 140 | | | | | |

| TGG | AAG | ATT | GAT | GGC | AGT | GAA | CGA | CAA | AAT | GGC | GTC | CTG | AAC | AGT | TGG | 480 |
| Trp | Lys | Ile | Asp | Gly | Ser | Glu | Arg | Gln | Asn | Gly | Val | Leu | Asn | Ser | Trp | |
| 145 | | | | | 150 | | | | | 155 | | | | | 160 | |

| ACT | GAT | CAG | GAC | AGC | AAA | GAC | AGC | ACC | TAC | AGC | ATG | AGC | AGC | ACC | CTC | 528 |
| Thr | Asp | Gln | Asp | Ser | Lys | Asp | Ser | Thr | Tyr | Ser | Met | Ser | Ser | Thr | Leu | |
| | | | | 165 | | | | | 170 | | | | | 175 | | |

| ACG | TTG | ACC | AAG | GAC | GAG | TAT | GAA | CGA | CAT | AAC | AGC | TAT | ACC | TGT | GAG | 576 |
| Thr | Leu | Thr | Lys | Asp | Glu | Tyr | Glu | Arg | His | Asn | Ser | Tyr | Thr | Cys | Glu | |
| | | | 180 | | | | | 185 | | | | | 190 | | | |

| GCC | ACT | CAC | AAG | ACA | TCA | ACT | TCA | CCC | ATT | GTC | AAG | AGC | TTC | AAC | AGG | 624 |
| Ala | Thr | His | Lys | Thr | Ser | Thr | Ser | Pro | Ile | Val | Lys | Ser | Phe | Asn | Arg | |
| | | 195 | | | | | 200 | | | | | 205 | | | | |

| AAT | GAG | TGT | | | | | | | | | | | | | | 633 |
| Asn | Glu | Cys | | | | | | | | | | | | | | |
| | 210 | | | | | | | | | | | | | | | |

( 2 ) INFORMATION FOR SEQ ID NO:8:

( i ) SEQUENCE CHARACTERISTICS:
        ( A ) LENGTH: 211 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met Thr Gln Thr Pro Ser Ser Leu Ser Ala Ser Leu Gly Asp Arg Val
 1               5                  10                  15

Thr Ile Ser Cys Arg Ala Ser Gln Asp Ile Lys Asn Tyr Leu Asn Trp
            20                  25                  30

Tyr Gln Gln Gly Pro Gly Gly Thr Val Lys Val Leu Ile Tyr Tyr Thr
                35                  40                  45

Ser Arg Leu His Ser Gly Val Pro Ser Arg Phe Ser Gly Ser Gly Ser
        50                  55                  60

Gly Thr Asp Tyr Ser Leu Thr Ile Ser Asn Leu Glu Gln Glu Asp Phe
 65                  70                  75                  80

Ala Thr Tyr Phe Cys Gln Arg Gly Asp Thr Leu Pro Trp Thr Phe Gly
                85                  90                  95

Gly Gly Thr Lys Leu Glu Ile Lys Thr Ala Asp Ala Ala Pro Thr Val
            100                 105                 110

Ser Ile Phe Pro Pro Ser Ser Glu Gln Leu Thr Ser Gly Gly Ala Ser
        115                 120                 125

Val Val Cys Phe Leu Asn Asn Phe Tyr Pro Lys Asp Ile Asn Val Lys
    130                 135                 140

Trp Lys Ile Asp Gly Ser Glu Arg Gln Asn Gly Val Leu Asn Ser Trp
145                 150                 155                 160

Thr Asp Gln Asp Ser Lys Asp Ser Thr Tyr Ser Met Ser Ser Thr Leu
                165                 170                 175

Thr Leu Thr Lys Asp Glu Tyr Glu Arg His Asn Ser Tyr Thr Cys Glu
            180                 185                 190

Ala Thr His Lys Thr Ser Thr Ser Pro Ile Val Lys Ser Phe Asn Arg
        195                 200                 205

Asn Glu Cys
210
```

( 2 ) INFORMATION FOR SEQ ID NO:9:

( i ) SEQUENCE CHARACTERISTICS:
        ( A ) LENGTH: 1128 base pairs
        ( B ) TYPE: nucleic acid
        ( C ) STRANDEDNESS: both
        ( D ) TOPOLOGY: linear ( i i ) MOLECULE TYPE: cDNA ( x i ) SEQUENCE DESCRIPTION: SEQ ID NO:9:

```
ATGGAGCGCG CGTCCTGCTT GTTGCTGCTG CTGCTGCCGC TGGTGCACGT CTCTGCGACC    60
ACGCCAGAAC CTTGTGAGCT GGACGATGAA GATTTCCGCT GCGTCTGCAA CTTCTCCGAA   120
CCTCAGCCCG ACTGGTCCGA AGCCTTCCAG TGTGTGTCTG CAGTAGAGGT GGAGATCCAT   180
GCCGGCGGTC TCAACCTAGA GCCGTTTCTA AAGCGCGTCG ATGCGGACCG CGACCCGCGG   240
CAGTATGCTG ACACGGTCAA GGCTCTCCGC GTGCGGCGGC TCACAGTGGG AGCCGCACAG   300
GTTCCTGCTC AGCTACTGGT AGGCGCCCTG CGTGTGCTAG CGTACTCCCG CCTCAAGGAA   360
CTGACGCTCG AGGACCTAAA GATAACCGGC ACCATGCCTC CGCTGCCTCT GGAAGCCACA   420
GGACTTGCAC TTTCCAGCTT GCGCCTACGC AACGTGTCGT GGGCGACAGG GCGTTCTTGG   480
CTCGCCGAGC TGCAGCAGTG GCTCAAGCCA GGCCTCAAGG TACTGAGCAT TGCCCAAGCA   540
CACTCGCCTG CCTTTTCCTG CGAACAGGTT CGCGCCTTCC CGGCCCTTAC CAGCCTAGAC   600
```

| | | | | | |
|---|---|---|---|---|---|
| CTGTCTGACA | ATCCTGGACT | GGGCGAACGC | GGACTGATGG | CGGCTCTCTG | TCCCCACAAG  660 |
| TTCCCGGCCA | TCCAGAATCT | AGCGCTGCGC | AACACAGGAA | TGGAGACGCC | CACAGGCGTG  720 |
| TGCGCCGCAC | TGGCGGCGGC | AGGTGTGCAG | CCCCACAGCC | TAGACCTCAG | CCACAACTCG  780 |
| CTGCGCGCCA | CCGTAAACCC | TAGCGCTCCG | AGATGCATGT | GGTCCAGCGC | CCTGAACTCC  840 |
| CTCAATCTGT | CGTTCGCTGG | GCTGGAACAG | GTGCCTAAAG | GACTGCCAGC | CAAGCTCAGA  900 |
| GTGCTCGATC | TCAGCTGCAA | CAGACTGAAC | AGGGCGCCGC | AGCCTGACGA | GCTGCCCGAG  960 |
| GTGGATAACC | TGACACTGGA | CGGGAATCCC | TTCCTGGTCC | CTGGAACTGC | CCTCCCCCAC 1020 |
| GAGGGCTCAA | TGAACTCCGG | CGTGGTCCCA | GCCTGTGCAC | GTTCGACCCT | GTCGGTGGGG 1080 |
| GTGTCGGGAA | CCCTGGTGCT | GCTCCAAGGG | GCCCGGGGCT | TTGCCTAA | 1128 |

(2) INFORMATION FOR SEQ ID NO:10:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:10:

Ser Tyr Ala Met Ser
    1                5

(2) INFORMATION FOR SEQ ID NO:11:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:11:

Ser Ile Ser Ser Gly Gly Thr Thr Tyr Tyr Pro Asp Asn Val Lys Gly
    1                5                    10                      15

(2) INFORMATION FOR SEQ ID NO:12:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:12:

Gly Tyr Tyr Asp Tyr His Tyr
    1                   5

(2) INFORMATION FOR SEQ ID NO:13:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal ( x i ) SEQUENCE DESCRIPTION: SEQ ID NO:13:

Ser Asp Ser Ala Trp Asn
1               5

( 2 ) INFORMATION FOR SEQ ID NO:14:

( i ) SEQUENCE CHARACTERISTICS:
    ( A ) LENGTH: 16 amino acids
    ( B ) TYPE: amino acid
    ( D ) TOPOLOGY: linear ( i i ) MOLECULE TYPE: peptide ( v ) FRAGMENT TYPE: internal ( x i ) SEQUENCE DESCRIPTION: SEQ ID NO:14:

Tyr Ile Ser Tyr Ser Gly Ser Thr Ser Tyr Asn Pro Ser Leu Lys Ser
1               5                   10                  15

( 2 ) INFORMATION FOR SEQ ID NO:15:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( v ) FRAGMENT TYPE: internal ( x i ) SEQUENCE DESCRIPTION: SEQ ID NO:15:

Gly Leu Arg Phe Ala Tyr
1               5

( 2 ) INFORMATION FOR SEQ ID NO:16:

( i ) SEQUENCE CHARACTERISTICS:
    ( A ) LENGTH: 15 amino acids
    ( B ) TYPE: amino acid
    ( D ) TOPOLOGY: linear ( i i ) MOLECULE TYPE: peptide ( v ) FRAGMENT TYPE: internal ( x i ) SEQUENCE DESCRIPTION: SEQ ID NO:16:

Arg Ala Ser Glu Ser Val Asp Ser Phe Gly Asn Ser Phe Met His
1               5                   10                  15

( 2 ) INFORMATION FOR SEQ ID NO:17:

( i ) SEQUENCE CHARACTERISTICS:
    ( A ) LENGTH: 7 amino acids
    ( B ) TYPE: amino acid
    ( D ) TOPOLOGY: linear ( i i ) MOLECULE TYPE: peptide ( v ) FRAGMENT TYPE: internal ( x i ) SEQUENCE DESCRIPTION: SEQ ID NO:17:

Arg Ala Ala Asn Leu Glu Ser
1               5

( 2 ) INFORMATION FOR SEQ ID NO:18:

( i ) SEQUENCE CHARACTERISTICS:
    ( A ) LENGTH: 9 amino acids
    ( B ) TYPE: amino acid (D) TOPOLOGY: linear (ii) MOLECULE TYPE: peptide (v) FRAGMENT TYPE: internal (xi) SEQUENCE DESCRIPTION: SEQ ID NO:18:

Gln Gln Ser Tyr Glu Asp Pro Trp Thr
1               5

(2) INFORMATION FOR SEQ ID NO:19:

(i) SEQUENCE CHARACTERISTICS:
      (A) LENGTH: 15 amino acids
      (B) TYPE: amino acid
      (D) TOPOLOGY: linear (ii) MOLECULE TYPE: peptide (v) FRAGMENT TYPE: internal (xi) SEQUENCE DESCRIPTION: SEQ ID NO:19:

Arg Ala Ser Glu Ser Val Asp Ser Tyr Val Asn Ser Phe Leu His
1               5                   10                  15

(2) INFORMATION FOR SEQ ID NO:20:

(i) SEQUENCE CHARACTERISTICS:
      (A) LENGTH: 7 amino acids
      (B) TYPE: amino acid
      (D) TOPOLOGY: linear (ii) MOLECULE TYPE: peptide (v) FRAGMENT TYPE: internal (xi) SEQUENCE DESCRIPTION: SEQ ID NO:20:

Arg Ala Ser Asn Leu Gln Ser
1               5

(2) INFORMATION FOR SEQ ID NO:21:

(i) SEQUENCE CHARACTERISTICS:
      (A) LENGTH: 9 amino acids
      (B) TYPE: amino acid
      (D) TOPOLOGY: linear (ii) MOLECULE TYPE: peptide (v) FRAGMENT TYPE: internal (xi) SEQUENCE DESCRIPTION: SEQ ID NO:21:

Gln Gln Ser Asn Glu Asp Pro Thr Thr
1               5

(2) INFORMATION FOR SEQ ID NO:22:

(i) SEQUENCE CHARACTERISTICS:
      (A) LENGTH: 15 amino acids
      (B) TYPE: amino acid
      (D) TOPOLOGY: linear (ii) MOLECULE TYPE: peptide (v) FRAGMENT TYPE: internal (xi) SEQUENCE DESCRIPTION: SEQ ID NO:22:

Arg Ala Ser Glu Ser Val Asp Ser Tyr Gly Lys Ser Phe Met His
1               5                   10                  15

-continued ( 2 ) INFORMATION FOR SEQ ID NO:23:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:23:

Val Ala Ser Lys Leu Glu Ser
    1              5

( 2 ) INFORMATION FOR SEQ ID NO:24:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:24:

Gln Gln Met Asn Glu Asp Pro Tyr Thr
    1              5

( 2 ) INFORMATION FOR SEQ ID NO:25:

( i ) SEQUENCE CHARACTERISTICS:
        ( A ) LENGTH: 112 amino acids
        ( B ) TYPE: amino acid
        ( D ) TOPOLOGY: linear ( i i ) MOLECULE TYPE: protein ( x i ) SEQUENCE DESCRIPTION: SEQ ID NO:25:

```
Gln Ser Pro Ala Ser Leu Ala Val Ser Leu Gly Gln Arg Ala Thr Ile Ser Cys
  1           5                    10                    15
Arg Ala Ser Glu Ser Val Asp Ser Tyr Gly Lys Ser Phe Met His Trp Tyr
 20                  25                  30                      35
Gln Gln Glu Pro Gly Gln Ser Pro Lys Leu Leu Ile Tyr Val Ala Ser Lys Leu
            40                  45                  50
Glu Ser Gly Val Pro Ala Arg Phe Ser Gly Ser Gly Ser Arg Thr Asp Phe Thr
 55                     60                  65                      70
Leu Thr Ile Asp Pro Val Glu Ala Asp Ala Ala Thr Tyr Tyr Cys Gln Gln
            75              80                  85
Ala Asp Asp Val Ala Thr Tyr Tyr Cys Gln Gln Ser Asn Glu Asp Pro
 90              95              100                 105
Met Asn Glu Asp Pro Tyr Thr
              110
```

We claim:

1. A monoclonal antibody ATCC HB11364 or ATCC HB11637.

2. A fragment of the monoclonal antibody of claim 1, wherein said fragment selectively binds to cell surface CD14.

3. The fragment of claim 2, wherein the biologically active fragment is Fab, Fab' or (Fab')$_2$.

4. A chimeric antibody comprising a variable region of the monoclonal antibody of claim 1.

5. An antibody comprising grafted complementarity determining regions (CDR) of the monoclonal antibody of claim 1.

6. An isolated nucleic acid molecule encoding the monoclonal antibody of claim 1.

7. An isolated nucleic acid molecule encoding the chimeric antibody of claim 4.

8. An isolated nucleic acid molecule encoding the CDR grafted antibody of claim 5.

9. The nucleic acid molecules as in any of claims 6, 7, or 8, wherein the nucleic acid molecules are single stranded DNA, double stranded DNA, cDNA, or RNA.

10. The nucleic acid molecule as in any of claims 6, 7, or 8 operatively linked to a promoter of RNA transcription.

11. An expression vector comprising the nucleic acid molecule of claims 6, 7, or 8.

12. The expression vector of claim 11, wherein the expression vector is a virus, plasmid, or cosmid.

13. A host cell containing the expression vector of claim 11.

14. The host cell of claim 13, wherein the host cell is a procaryotic cell.

15. The host cell of claim 14, wherein the cell is an *Escherichia coli*.

16. The host cell of claim 13, wherein the host cell is a eucaryotic cell.

17. The host cell of claim 16, wherein the eucaryotic cell is a mammalian cell or an insect cell.

18. A monoclonal antibody which is designated ATCC HB11363.

19. A fragment of the monoclonal antibody of claim 18, wherein said fragment selectively binds CD14.

20. The fragment of claim 19, wherein said fragment is Fab, Fab' or (Fab')$_2$.

21. A chimeric antibody comprising a variable region of the monoclonal antibody of claim 18.

22. A CDR grafted antibody comprising a complementarity determining region (CDR) of the monoclonal antibody of claim 18.

23. An isolated nucleic acid molecule encoding the monoclonal antibody of claim 18.

24. An isolated nucleic acid molecule encoding the monoclonal antibody of claim 20.

25. An isolated nucleic acid molecule encoding the fragment of claim 19.

26. An isolated nucleic acid molecule encoding the chimeric antibody of claim 21.

27. An isolated nucleic acid molecule encoding the CDR grafted antibody of claim 22.

28. The nucleic acid molecule of claims 23, 24, 25, 26, or 27, wherein the nucleic acid is single stranded DNA, double stranded DNA, cDNA or RNA.

29. The nucleic acid molecule of claims 23, 24, 25, 26, or 27 operatively linked to a promoter of RNA transcription.

30. An expression vector containing the nucleic acid molecule of claims 23, 24, 25, 26, or 27.

31. The expression vector of claim 30, wherein the expression vector is a virus, plasmid, or cosmid.

32. A host cell containing the expression vector of claim 30.

33. The host cell of claim 32, wherein the host cell is a procaryotic cell.

34. The host cell of claim 33, wherein the cell is an *Escherichia coli*.

35. The host cell of claim 32, wherein the host cell is a eucaryotic cell.

36. The host cell of claim 33, wherein the cell is a mammalian cell or an insect cell.

37. A pharmaceutical composition comprising an antibody selected from the group consisting of ATCC HB11364, ATCC HB11637, or ATCC HB11363 in a pharmaceutically acceptable carrier.

38. A method of detecting CD14 in a sample which comprises contacting the sample with ATCC HB11364, ATCC HB11637, or ATCC HB11363, or fragment thereof which binds to cell surface CD14 and soluble CD14 and determining whether there is binding to the sample.

39. The method of claim 38, wherein the antibody is detectably labeled.

40. The method of claim 39, wherein the detectable label is selected from the group consisting of a radioisotope, a fluorescent compound, a colloidal metal, a chemiluminescent compound, a bioluminescent compound and an enzyme.

41. The method of claim 38, wherein the method of detecting is by a competitive immunoassay method.

42. The method of claim 38, wherein the sample comprises a body fluid.

43. A method of inhibiting the binding of lipopolysaccharide (LPS) to CD14 which comprises contacting the CD14 with the monoclonal antibody of claim 1.

44. A method of inhibiting the binding of a lipopolysaccharide LPS/CD14 complex to a cell, which comprises contacting the complex with the monoclonal antibody of claim 1.

45. A method of inhibiting CD14 mediated activation of a cell expressing CD14 receptor, which comprises contacting the cell with an effective amount of an antibody selected from the group consisting of ATCC HB11364, ATCC HB11637, and ATCC HB11363.

46. The method of claim 45, wherein the antibody allows binding of a ligand to CD14.

47. The method of claim 46, wherein the antibody allows at least about 50% binding of the ligand to CD14.

48. The method of claim 46, wherein the antibody allows at least about 80% binding of the ligand to CD14.

49. The method of claim 45, wherein the CD14 mediated activation is associated with nuclear factor-κB (NF-κB) activation.

50. The method of claim 49, wherein the nuclear factor-κB (NF-κB) activation is associated with sepsis.

51. The method of claim 45, wherein the ligand is LPS.

52. The method of claim 45, wherein the cell is an animal or a human patient cell.

53. The method of claim 45, wherein an effective amount is from about 0.25 mg/kg/body weight to about 50 mg/kg/body weight.

54. A method of inhibiting CD14-mediated activation of a cell expressing a CD14 receptor in a subject displaying symptoms of sepsis or at risk for developing sepsis, comprising:
    administering to said subject a therapeutically effective amount of an antibody selected from the group consisting of ATCC HB11364, ATCC HB11637, and ATCC HB11363.

55. The method of claim 54, wherein said subject is treated with a bactericidal amount of an antibiotic in addition to said therapeutically effective amount of said antibody.

56. The method of claim 54, wherein said subject is treated with an inhibitor of tumor necrosis factor (TNF) in addition to said therapeutically effective amount of said antibody.

57. The method of claim 54, wherein an effective amount is from about 0.25 mg/kg/body weight to about 50 mg/kg/body weight.

58. The method of claim 54, wherein the subject is human.

59. The method of claim 58, wherein an effective amount is from about 0.5 mg/kg/body weight to about 8 mg/kg/body weight.

* * * * *